(12) United States Patent
Rusconi

(10) Patent No.: US 7,531,524 B2
(45) Date of Patent: May 12, 2009

(54) MODULATORS OF COAGULATION FACTORS WITH ENHANCED STABILITY

(75) Inventor: Christopher P. Rusconi, Durham, NC (US)

(73) Assignee: Regado Biosciences, Inc., Durham, NC (US)

( * ) Notice: Subject to any disclaimer, the term of this patent is extended or adjusted under 35 U.S.C. 154(b) by 230 days.

(21) Appl. No.: 11/546,190

(22) Filed: Oct. 11, 2006

(65) Prior Publication Data

US 2008/0125383 A1 May 29, 2008

Related U.S. Application Data

(63) Continuation-in-part of application No. 11/113,378, filed on Apr. 22, 2005, now Pat. No. 7,304,041.

(60) Provisional application No. 60/725,509, filed on Oct. 11, 2005.

(51) Int. Cl.
*C12Q 1/68* (2006.01)
*C12N 5/00* (2006.01)
*A01N 43/04* (2006.01)
*C07H 21/02* (2006.01)
*C07H 21/04* (2006.01)

(52) U.S. Cl. .............. 514/44; 424/1.73; 435/6; 435/91.1; 435/375; 435/455; 536/23.1; 536/24.5

(58) Field of Classification Search ............ 435/6, 435/91.1, 91.31, 455, 375; 514/1, 2, 44; 536/23.1, 24.5; 424/1.73
See application file for complete search history.

(56) References Cited

U.S. PATENT DOCUMENTS

| | | | |
|---|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,973,679 A | 11/1990 | Caruthers et al. |
| 5,153,319 A | 10/1992 | Caruthers et al. |
| 5,180,818 A | 1/1993 | Cech et al. |
| 5,245,022 A | 9/1993 | Weis et al. |
| 5,270,163 A | 12/1993 | Gold et al. |
| 5,278,302 A | 1/1994 | Caruthers et al. |
| 5,453,496 A | 9/1995 | Caruthers et al. |
| 5,475,096 A | 12/1995 | Gold et al. |
| 5,476,766 A | 12/1995 | Gold et al. |
| 5,532,130 A | 7/1996 | Alul |
| 5,534,408 A | 7/1996 | Green et al. |
| 5,543,293 A | 8/1996 | Gold et al. |
| 5,552,391 A | 9/1996 | Coutts et al. |
| 5,582,981 A | 12/1996 | Toole et al. |
| 5,594,121 A | 1/1997 | Froehler et al. |
| 5,595,877 A | 1/1997 | Gold et al. |
| 5,602,244 A | 2/1997 | Carruthers et al. |
| 5,606,047 A | 2/1997 | Coutts et al. |
| 5,645,985 A | 7/1997 | Froehler et al. |
| 5,648,214 A | 7/1997 | Nieuwlandt et al. |
| 5,660,985 A | 8/1997 | Pieken et al. |
| 5,670,633 A | 9/1997 | Cook et al. |
| 5,670,637 A | 9/1997 | Gold et al. |
| 5,681,702 A | 10/1997 | Collins et al. |
| 5,686,242 A | 11/1997 | Bruice et al. |
| 5,696,249 A | 12/1997 | Gold et al. |
| 5,723,323 A | 3/1998 | Kauffman et al. |
| 5,750,729 A | 5/1998 | Alexander et al. |
| 5,756,291 A | 5/1998 | Griffin et al. |
| 5,760,202 A | 6/1998 | Cook et al. |
| 5,780,221 A | 7/1998 | Schumacher et al. |
| 5,780,449 A | 7/1998 | Bracht et al. |
| 5,780,610 A | 7/1998 | Collins et al. |
| 5,792,608 A | 8/1998 | Swaminathan et al. |
| 5,792,613 A | 8/1998 | Schmidt et al. |
| 5,807,718 A | 9/1998 | Joyce et al. |
| 5,814,476 A | 9/1998 | Kauffman et al. |
| 5,817,781 A | 10/1998 | Swaminathan et al. |
| 5,817,785 A | 10/1998 | Gold et al. |
| 5,830,653 A | 11/1998 | Froehler et al. |
| 5,839,443 A | 11/1998 | Rose |
| 5,840,867 A | 11/1998 | Toole et al. |
| 5,843,653 A | 12/1998 | Gold et al. |
| 5,859,221 A | 1/1999 | Cook et al. |
| 5,861,254 A | 1/1999 | Schneider |
| 5,861,501 A | 1/1999 | Benseler |
| 5,872,232 A | 2/1999 | Cook et al. |
| 5,879,917 A | 3/1999 | Essigmann et al. |
| 5,882,870 A | 3/1999 | Nadeau |
| 5,882,941 A | 3/1999 | Essigmann et al. |
| 5,891,689 A | 4/1999 | Takle et al. |
| 5,935,776 A | 8/1999 | Green et al. |
| 5,958,691 A | 9/1999 | Pieken et al. |
| 5,989,823 A | 11/1999 | Jayasena et al. |
| 6,001,820 A | 12/1999 | Hirsh et al. |
| 6,004,746 A | 12/1999 | Brent |
| 6,005,087 A | 12/1999 | Cook et al. |

(Continued)

FOREIGN PATENT DOCUMENTS

EP 0593901 A2 4/1994

(Continued)

OTHER PUBLICATIONS

Agrawal, S., and Kandimalla, E.R., "Antisense therapeutics: is it as simple as complementary base recognition?" *Mol. Med. Today*, 6(2):72-81 (Feb. 2000).

(Continued)

*Primary Examiner*—Jane Zara

(57) ABSTRACT

The invention provides improved nucleic acid ligands with enhanced stability that inhibit coagulation and improved modulators of the nucleic acids to provide ideal modulators of coagulation. These improved nucleic acids and modulators are particularly useful for inhibiting coagulation in a host undergoing a therapeutic regime such as surgery or coronary artery bypass.

46 Claims, 21 Drawing Sheets

U.S. PATENT DOCUMENTS

| | | | |
|---|---|---|---|
| 6,011,020 | A | 1/2000 | Gold et al. |
| 6,051,388 | A | 4/2000 | Bodenhamer |
| 6,054,274 | A | 4/2000 | Sampson et al. |
| 6,060,056 | A | 5/2000 | Coutts et al. |
| 6,083,696 | A | 7/2000 | Biesecker et al. |
| 6,093,555 | A | 7/2000 | Dudycz |
| 6,110,462 | A | 8/2000 | Barbas et al. |
| 6,110,721 | A | 8/2000 | Gibbs et al. |
| 6,110,900 | A | 8/2000 | Gold et al. |
| 6,111,095 | A | 8/2000 | Benseler et al. |
| 6,114,038 | A | 9/2000 | Castro et al. |
| 6,117,557 | A | 9/2000 | Massie, II et al. |
| 6,120,997 | A | 9/2000 | Wong et al. |
| 6,127,119 | A | 10/2000 | Stephens et al. |
| 6,127,173 | A | 10/2000 | Eckstein et al. |
| 6,136,545 | A | 10/2000 | Hosel et al. |
| 6,147,204 | A | 11/2000 | Gold et al. |
| 6,150,461 | A | 11/2000 | Takei et al. |
| 6,153,410 | A | 11/2000 | Arnold et al. |
| 6,153,737 | A | 11/2000 | Manoharan et al. |
| 6,163,714 | A | 12/2000 | Stanley et al. |
| 6,171,795 | B1 | 1/2001 | Korman et al. |
| 6,177,263 | B1 | 1/2001 | Arnold et al. |
| 6,177,555 | B1 | 1/2001 | Jayasena et al. |
| 6,177,557 | B1 | 1/2001 | Janjic et al. |
| 6,180,348 | B1 | 1/2001 | Li |
| 6,183,967 | B1 | 2/2001 | Jayasena et al. |
| 6,222,025 | B1 | 4/2001 | Cook et al. |
| 6,258,601 | B1 | 7/2001 | Monia et al. |
| 6,315,995 | B1 | 11/2001 | Pinsky |
| 6,316,198 | B1 | 11/2001 | Skouv et al. |
| 6,316,403 | B1 | 11/2001 | Pinsky |
| 6,331,398 | B1 | 12/2001 | Gold et al. |
| 6,391,300 | B1 | 5/2002 | Rose |
| 6,531,584 | B1 | 3/2003 | Cook et al. |
| 2003/0083294 | A1 | 5/2003 | Sullenger et al. |
| 2003/0175703 | A1 | 9/2003 | Sullenger |
| 2006/0004088 | A1 | 1/2006 | Kim et al. |

FOREIGN PATENT DOCUMENTS

| | | |
|---|---|---|
| EP | 1026243 A1 | 8/2000 |
| JP | 11127864 A2 | 5/1999 |
| WO | WO 91/19813 A1 | 12/1991 |
| WO | WO 92/14842 A1 | 9/1992 |
| WO | WO 94/06811 A1 | 3/1994 |
| WO | WO 94/08050 A1 | 4/1994 |
| WO | WO 97/42317 A1 | 11/1997 |
| WO | WO 99/33971 A1 | 7/1999 |
| WO | WO 99/50462 A1 | 10/1999 |
| WO | WO 00/20040 A1 | 4/2000 |
| WO | WO 00/22114 A1 | 4/2000 |
| WO | WO 00/24912 A1 | 5/2000 |
| WO | WO 00/42063 A2 | 7/2000 |
| WO | WO 00/42064 A1 | 7/2000 |
| WO | WO 00/47774 A1 | 8/2000 |
| WO | WO 02/26932 A2 | 4/2002 |
| WO | WO 02/096926 A1 | 12/2002 |
| WO | WO 03/093422 A2 | 11/2003 |
| WO | WO 2004/011680 A1 | 2/2004 |
| WO | WO 2004/014844 A3 | 2/2004 |
| WO | WO 2004/047742 A2 | 6/2004 |
| WO | WO 2004/050899 A2 | 6/2004 |
| WO | WO 2005/010150 A2 | 2/2005 |
| WO | WO 2005/014533 A2 | 2/2005 |
| WO | WO 2005/052121 A2 | 6/2005 |
| WO | WO 2005/084412 A2 | 9/2005 |
| WO | WO 2005/111238 A2 | 11/2005 |
| WO | WO 2006/029258 A2 | 3/2006 |
| WO | WO 2006/033854 A2 | 3/2006 |

OTHER PUBLICATIONS

Aldaz-Carroll, et al., "Apical loop-internal loop interactions: a new RNA-RNA recognition motif identified through in vitro selection against RNA hairpins of the hepatitis C virus mRNA," *Biochemistry*, 41(18):5883-5893 (May 7, 2002) (abst).

Ananyeva, N.M., et al., "Intrinsic pathway of blood coagulation contributes to thrombogenicity of atherosclerotic plaque," *Blood*, 99(12):4475-4485 (Jun. 15, 2002) (Epublication Apr. 17, 2002).

Beigelman, L., et al., "Chemical modification of hammerhead ribozymes. Catalytic activity and nuclease resistance," *J. Biol. Chem.*, 270(43):25702-25708 (Oct. 25, 1995).

Biedenkapp, H., et al., "Viral myb oncogene encodes a sequence-specific DNA-binding activity," *Nature*, 335(6193):835-837 (Oct. 27, 1988).

Biesecker, G., et al., "Derivation of RNA aptamer inhibitors of human complement C5'," *Immunopharmacology*, 42(1-3):219-230 (May 1999) (abst).

Bilora, F., et al., "Do hemophilia A and von Willebrand disease protect against carotid atherosclerosis? A comparative study between coagulopathics and normal subjects by means of carotid echo-color Doppler scan" *Clin. Appl. Thromb. Hemost.*, 5(4):232-235 (Oct. 1999).

Black, A.R., and Azizkhan-Clifford, J., "Regulation of E2F: a family of transcription factors involved in proliferation control," *Gene*, 237(2);281-302 (Sep. 17, 1999).

Boiziau, C., et al., "DNA aptamers selected against the HIV-1 trans-activation responsive RNA element form RNA-DNA kissing complexes," *J. Biol. Chem.*, 274(18):12730-12737 (Apr. 30, 1999).

Burke, D.H., and Hoffman, D.C., "A novel axidophilic RNA motif that recognizes Coenzyme A," *Biochemistry*, 37(13):4653-4663 (Mar. 31, 1998) (abst.).

Callas, D., and Fareed, J., "Comparative pharmacology of site directed antithrombin agents Implication in drug development," *Thromb. Haemost.*, 74(1):473-481 (Jul. 1995) (abst).

Charlton, J., et al., "In vivo imaging of inflammation using an aptamer inhibitor of human neutrophil elastase," *Chem. Biol.*, 4(11):809-816 (Nov. 1997) (abst).

Chase, J.W., and Williams, K.R., "Single-stranded DNA binding proteins required for DNA replication," *Annu. Rev. Biochem.*, 55:103-136 (1986).

Collin, D., et al., "NMR characterization of a kissing complex formed between the TAR RNA element of HIV-1 and a DNA aptamer," *Nucleic Acids Res.*, 28(17):3386-3391 (Sep. 1, 2000).

Cooper, J.A., et al., "Comparison of novel hemostatic factors and conventional risk factors for prediction of coronary heart disease," *Circulation*, 102(23):2816-2822 (Dec. 5, 2000).

Dale, R.M., et al., "Direct covalent mercuration of nucleotides and polynucleotides," *Biochemistry*, 14(11):2447-2457 (Jun. 3, 1975).

Darfeuille, F., et al., "RNA and N3'->P5' kissing aptamers targeted to the trans-activation responsive (TAR) RNA of the human immunodeficiency virus-1," *Nucleosides Nucleotides Nucleic Acids*, 20(4-7):441-449 (Apr.-Jul. 2001) (abst.).

Davis, et al., Chap. 8, p. 185, in *RNA World* (Cold Spring Harbor Laboratory Press; eds. Gestlaad and Atkins; 1993).

DeAnda, A. Jr., et al., "Pilot study of the efficacy of a thrombin inhibitor for use during cardiopulmonary bypass," *Ann. Thorac. Surg.*, 58(2):344-350 (Aug. 1994).

Duconge, F., et al., "Is closing "GA PAI" a rule for stable loop-loop RNA complexes?" *J. Biol. Chem.*, 275(28):21287-21294 (Jul. 14, 2000).

Eichhorn, G.L., and Shin, Y.A., "Interaction of metal ions with polynucleotides and related compounds. XII. The relative effect of various metal ions on DNA helicity," *J. Am. Chem. Soc.*, 90(26):7323-7328 (Dec. 18, 1968).

Ellington, A.D., and Szostak, J.W., "Selection of RNAs with ligand-specific binding activity from pools of random sequence molecules," Abstract; Cold Spring Harbor "RNA Processing" Conference (May 16-20, 1990).

Feuerstein, G.Z., et al., "Antithrombotic efficacy of a novel murine antihuman factor IX antibody in rats," *Arterioscler. Thromb. Vasc. Biol.*, 19(10):2554-2562 (Oct. 1999).

Gal, S.W., et al., "Selection of a RNA aptamer that binds to human activated protein C and inhibits its protease function," *Eur. J. Biochem.*, 252(3):553-562 (Mar. 15, 1998) (abst.).

Gitel, S.N., et al., "In vitro and in vivo correlation of clotting protease activity: effect of heparin," *Proc. Natl. Acad. Sci. U.S.A.*, 74(7):3028-3032 (Jul. 1977).

Good, P.D., et al., "Expression of small, therapeutic RNAs in human cell nuclei," *Gene Ther.*, 4(1):45-54 (Jan. 1997).

Griffin, L.C., et al., "In vivo anticoagulant properties of a novel nucleotide-based thrombin inhibitor and demonstration of regional anticoagulation in extracorporeal circuits," *Blood*, 81(12):3271-3276 (Jun. 15, 1993).

Gurewich, V., et al., "Activation of intrinsic or extrinsic blood coagulation in experimental venous thrombosis and disseminated intravascular coagulation: pathogenetic differences," *Thromb. Res.*, 14(6):931-940 (1979).

Harbour, J.W., and Dean, D.C., "The Rb/E2F pathway: expanding roles and emerging paradigms," *Genes Dev.*, 14(19):2393-2409 (Oct. 1, 2000).

Helin, K., and Ed, H., "The retinoblastoma protein as a transcriptional repressor," *Trends Cell Biol.*, 3(2):43-46 (Feb. 1993).

Hunter, T., "Braking the cycle," *Cell*, 75(5):839-841 (Dec. 3, 1993).

Hwang, S., et al., "Inhibition of gene expression in human cells through small molecule-RNA interactions," *Proc. Natl. Acad. Sci. U.S.A.*, 96(23):12977-13002 (1999).

Ishizaki, J., et al., "Inhibition of cell proliferation by an RNA ligand that selectively blocks E2F function," *Nature Med.*, 2(12):1386-1389 (Dec. 1996).

Jen, K.Y., and Gewirtz, A.M., "Suppression of gene expression by targeted disruption of messenger RNA: available options and current strategies," *Stem Cells*, 18(5):307-319 (2000).

Kinzler, K.W., and Vogelstein, B., "Whole genome PCR: application to the identification of sequences bound by gene regulatory proteins," *Nucleic Acids Res.*, 17(10):3645-3653 (May 25, 1989).

Koshkin, A.A., et al., "LNA (Locked Nucleic Acids): Synthesis of adenin, cytosine, guanine, 5-methylcytosine, thymine and uracil bicyclonucleoside monomers, oligomerisation, and unprecedented nucleic acid recognition," *Tetrahedron*, 54:3607-3630 (1998).

La Thangue, N.B., "DRTF1/E2F: an expanding family of heterodimeric transcription factors implicated in cell-cycle control," *Trends Biochem. Sci.*, 19(3):108-114 (Mar. 1994).

Le Tinevez, R., et al., "Selective inhibition of cell-free translation by oligonucleotides targeted to a mRNA hairpin structure," *Nucleic Acids Res.*, 26(10):2273-2278 (May 15, 1998).

LeClerc, F., et al., "A three dimensional model of the Rev-binding element of HIV—a derived from analyses of apramers," *Nat. Struct. Biol.*, 1(5):293-300 (May 1994) (abst).

Lee, S.W., et al., "Isolation of a nuclease-resistant decoy RNA that can protect human acetylcholine receptors from myasthenic antibodies," *Nature Biotechnol.*, 15(1):41-45 (Jan. 1997).

Leva, S., et al., "GnRH binding RNA and DNA Spiegelmers A novel approach toward GnRH antagonism," *Chemistry & Biology*, 8(3):351-359 (Mar. 2002).

Li, W.X., et al., "A novel nucleotide based thrombin inhibitor inhibits clot bound thrombin and reduces arterial platelet thrombus formation," *Blood*, 83(3):677-682 (Feb. 1, 1994) (abst).

Lippard, et al., "Platinum complexes: probes of polynucleotide structure and antitumor drugs," *Acc. Chem. Res.*, 11:211-217 (1978).

Lowe, G.D., et al., "Factor IX and thrombosis," *Br. J. Haematol.*, 115(3):507-513 (Dec. 2001).

Mann, K.G., et al., "Surface-dependent reactions of the vitamin K-dependent enzyme complexes," *Blood*, 76(1):1-16 (Jul. 1, 1990).

Monfardini, C., et al., "A branched monomethoxypoly(ethylene glycol) for protein modification," *Bioconj. Chem.*, 6(1):62-69 (Jan.-Feb. 1995).

Nevins, J.R., "E2F: a link between the Rb tumor suppressor protein and viral oncoproteins," *Science*, 258(5081):424-429 (Oct. 16, 1992).

Oliphant, A.R., et al., "Defining the sequence specificity of DNA-binding proteins by selecting binding sites from random-sequence oligonucleotides: analysis of yeast GCN4 protein," *Mol. Cell. Biol.*, 9(7):2944-2949 (Jul. 1989).

Opalinska, J.B., and Gewirtz, A.M., "Nucleic-acid therapeutics: basic principles and recent applications," *Nat. Rev. Drug Discovery*, 1(7):503-514 (Jul. 2002).

Padmanabhan, K., et al., "The structure of alpha thrombin inhibited by a 15-mer single stranded DNA aptamer," *J. Biol. Chem.*, 268(24):17651-17654 (Aug. 25, 1993) (abst).

Pieken, W.A., et al., "Kinetic characterization of ribonuclease-resistant 2'-modified hammerhead ribozymes," *Science*, 253(5017):314-317 (Jul. 19, 1991).

Refino, C.J., et al., "A human antibody that binds to the gamma-carboxyglutamic acid domain of factor IX is a potent antithrombotic in vivo.," *Thromb. Haemost.*, 82(3):1188-1195 (Sep. 1999).

Robertson, D.L., and Joyce, G.F., "Selection in vitro of an RNA enzyme that specifically cleaves single-stranded DNA," *Nature*, 344(6265):467-468 (Mar. 29, 1990).

Rosenberg, R.D., "Vascular-bed-specific hemostasis and hypercoagulable states: clinical utility of activation peptide assays in predicting thrombotic events in different clinical populations," *Thromb. Haemost.*, 86(1):41-50 (Jul. 2001).

Rusconi, C.P., et al., "Blocking the initiation of coagulation by RNA aptamers to factor VIIa," *Thrombosis and Haemostasis*, 84(5):841-848 (Nov. 2000).

Rusconi, C.P., et al., "RNA aptamers as reversible antagonists of coagulation Factor IXa," *Nature*, 419(6902):90-94 (Sep. 5, 2002).

Scarabeo, V., et al., "Dissection of the ascending aorta mimicking an acute coronary syndrome: usefulness of transthoracic echocardiography for the differential diagnosis," *Ital. Heart J.*, 3(8):490-494 (Aug. 2002).

Shaw, J.P., et al., "A novel oligodeoxynucleotide inhibitor of thrombin 1. In vitro metabolic stability in plasma and seum," *Pharm. Res.*, 12(12):1937-1942 (Dec. 1995) (abst.).

Sheehan, J.P., and Lan, H.C., "Phosphorothioate oligonucleotides inhibit the intrinsic tenase complex," *Blood*, 92(5):1617-1625 (Sep. 1, 1998).

Sherr, C.J., "Mammalian G1 cyclins," *Cell*, 73(6):1059-1065 (Jun. 18, 1993).

Sherr, C.J., and Roberts, J.M., "Inhibitors of mammalian G1 cyclin-dependent kinases," *Genes Dev.*, 9(10):1149-1163 (May 15, 1995).

Smirnov, I., and Shafer, R.H., "Effect of loop sequence and size on DNA aptamer stability," *Biochemistry*, 39(6):1462-1468 (Feb. 15, 2000).

Šrámek, A., et al., "Decreased mortality of ischaemic heart disease among carriers of haemophilia," *Lancet*, 362(9381):351-354 (Aug. 2, 2003).

Sullenger, B.A., et al., "Overexpression of TAR sequences renders cells resistant to human immunodeficiency virus replication," *Cell*, 63(3):601-608 (Nov. 2, 1990).

Sullenger, B.A., et al., "Therapeutic aptamers and antidotes: a novel approach to safer drug design," Chap. 13 in *Human gene therapy: current opportunities and future trends*, G. M. Rubanyi ; S. Ylä-Herttuala Eds. (Ernst Schering Foundation Workshop on Human Gene Therapy, Berkeley, Calif., Oct. 2-4, 2002; Springer, Berlin, 2003), ISBN 3-540-00413-0, pp. 217-223.

Szostak, J.W., "Structure and activity of ribozymes; redesigning the molecules of life," Conference of the International Symposium on Bioorganic Chemistry, Interlaken (May 4-6, 1988).

Tasset, D.M., et al., "Oligonucleotide inhibitors of human thrombin that bind distinct epitopes," *J. Mol. Biol.*, 272(5):688-698 (Oct. 10, 1997) (abst).

Toomey, J.R., et al., "Comparing the antithrombotic efficacy of a humanized anti-factor IX(a) monoclonal antibody (SB 249417) to the low molecular weight heparin enoxaparin in a rat model of arterial thrombosis," *Thromb. Res.*, 100(1):73-79 (Oct. 1, 2000).

Tucker, C.E. et al., "Detection and plasma pharmacokinetics of an anti-vascular endothelial growth factor oligonucleotide aptamer in (NX1838) rhesus monkeys," *J. Chromatogr. B Biomed. Sci. Appl.*, 732(1):203-212 (Sep. 10, 1999).

Tucker, C.E., et al., "Detection and plasma pharmacokinetics of an anti-vascular endothelial growth factor oligonucleotide-aptamer (NX1838) in rhesus monkey," *J. Chromatog. B, Biomed. Sci. Appl.*, 732(1):203-212 (Sep. 10, 1999).

Tuerk, C., and Gold, L., "Systematic evolution of ligands by exponential enrichment: RNA ligands to bacteriophage T4 DNA polymerase," *Science*, 249(4968):505-510 (Aug. 3, 1990).

Wahlestedt, C., et al., "Potent and nontoxic antisense oligonucleotides containing locked nucleic acids," *Proc. Natl. Acad. Sci. U.S.A.*, 97(10):5633-5638 (May 9, 2000).

Weinberg, R.A., "The retinoblastoma protein and cell cycle control," *Cell*, 81(3):323-330 (May 5, 1995).

Werstuck, G., and Green, M.R., "Controlling gene expression in living cells through small molecule-RNA interactions," *Science*, 282(5387):296-298 (Oct. 9, 1998).

White, R.R., et al., "Developing aptamers into therapeutics," *J. Clin. Invest.*, 106(8):929-934 (Oct. 2000).

William, K.P., et al., "Bioactive and nuclease resistant L-DNA ligand of vasopressin PNAS," 94(21):11285-11290 (Oct. 14, 1997).

Willis, M.C., et al., "Liposome-anchored vascular endothelial growth factor aptamers," *Bioconjug. Chem.*, 9(5):573-582, (Sep.-Oct. 1998).

Willis, M.C., et al., "Liposome-anchored vascular endothelial growth factor aptamers," *Bioconjug. Chem.*, 9(5):633 (Sep.-Oct. 1998) [Erratum, Collins, B., corrected to Collins, B.D.].

A. AptA, 1-5

B. Apt. 6-11

C. Apt 12-17.

D. Apt 18-20.

E. Apt 21

Apt A, 1-5

Apt A, 1-5 antidote neutralization

SEQUENCE LISTING

<160> NUMBER OF SEQ ID NOS: 59

<210> SEQ ID NO 1
<211> LENGTH: 17
<212> TYPE: RNA
<213> ORGANISM: Artificial Sequence
<220> FEATURE:

<223> OTHER INFORMATION: Synthetic aptamer

<400> SEQUENCE: 1
cgcgguauag uccccau                                                  17

<210> SEQ ID NO 2
<211> LENGTH: 14
<212> TYPE: RNA
<213> ORGANISM: Artificial Sequence
<220> FEATURE:
<223> OTHER INFORMATION: Synthetic aptamer

<400> SEQUENCE: 2
cgcgguauag uccc                                                     14

<210> SEQ ID NO 3
<211> LENGTH: 15
<212> TYPE: RNA
<213> ORGANISM: Artificial Sequence
<220> FEATURE:
<223> OTHER INFORMATION: Synthetic aptamer

<400> SEQUENCE: 3
cgcgguauag uccac                                                    15

<210> SEQ ID NO 4
<211> LENGTH: 16
<212> TYPE: RNA
<213> ORGANISM: Artificial Sequence
<220> FEATURE:
<223> OTHER INFORMATION: Synthetic aptamer

<400> SEQUENCE: 4
cgcgguauag uccauc                                                   16

<210> SEQ ID NO 5
<211> LENGTH: 14
<212> TYPE: RNA
<213> ORGANISM: Artificial Sequence
<220> FEATURE:
<223> OTHER INFORMATION: Synthetic aptamer

<400> SEQUENCE: 5
cgcgguauag ucag                                                     14

<210> SEQ ID NO 6
<211> LENGTH: 15
<212> TYPE: RNA
<213> ORGANISM: Artificial Sequence
<220> FEATURE:
<223> OTHER INFORMATION: Synthetic aptamer

<400> SEQUENCE: 6
cgcgguauag ucagg                                                    15

<210> SEQ ID NO 7
<211> LENGTH: 16
<212> TYPE: RNA
<213> ORGANISM: Artificial Sequence
<220> FEATURE:
<223> OTHER INFORMATION: Synthetic aptamer

<400> SEQUENCE: 7
cgcgguauag ucagag                                                   16

```
<210> SEQ ID NO 8
<211> LENGTH: 17
<212> TYPE: RNA
<213> ORGANISM: Artificial Sequence
<220> FEATURE:
<223> OTHER INFORMATION: Synthetic aptamer

<400> SEQUENCE: 8
cgcgguauag uccucac                                                         17

<210> SEQ ID NO 9
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 9
auggggacua uaccgcguaa ugcugccucc ccaut                                     35

<210> SEQ ID NO 10
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 10
auggggacua uaccgcguaa ugcugccucc ccaut                                     35

<210> SEQ ID NO 11
<211> LENGTH: 29
<212> TYPE: DNA
<213> ORGANISM: Artificial Sequence
<220> FEATURE:
<223> OTHER INFORMATION: Synthetic aptamer

<400> SEQUENCE: 11
gggacuauac cgcguaaugc ugccuccct                                            29

<210> SEQ ID NO 12
<211> LENGTH: 31
<212> TYPE: DNA
<213> ORGANISM: Artificial Sequence
<220> FEATURE:
<223> OTHER INFORMATION: Synthetic aptamer

<400> SEQUENCE: 12
guggacuaua ccgcguaaug cugccuccac t                                         31

<210> SEQ ID NO 13
<211> LENGTH: 33
<212> TYPE: DNA
<213> ORGANISM: Artificial Sequence
<220> FEATURE:
<223> OTHER INFORMATION: Synthetic aptamer

<400> SEQUENCE: 13
gauggacuau accgcguaau gcugccucca uct                                       33

<210> SEQ ID NO 14
<211> LENGTH: 29
<212> TYPE: DNA
<213> ORGANISM: Artificial Sequence
<220> FEATURE:
<223> OTHER INFORMATION: Synthetic aptamer
```

```
<400> SEQUENCE: 14
cugacuauac cgcguaaugc ugccucagt                                    29

<210> SEQ ID NO 15
<211> LENGTH: 31
<212> TYPE: DNA
<213> ORGANISM: Artificial Sequence
<220> FEATURE:
<223> OTHER INFORMATION: Synthetic aptamer

<400> SEQUENCE: 15
ccugacuaua ccgcguaaug cugccucagg t                                 31

<210> SEQ ID NO 16
<211> LENGTH: 33
<212> TYPE: DNA
<213> ORGANISM: Artificial Sequence
<220> FEATURE:
<223> OTHER INFORMATION: Synthetic aptamer

<400> SEQUENCE: 16
cucugacuau accgcguaau gcugccucag agt                               33

<210> SEQ ID NO 17
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 17
gugaggacua uaccgcguaa ugcugccucc ucact                             35

<210> SEQ ID NO 18
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 18
gugaggacua uaccgcguaa ugcugccucc ucact                             35

<210> SEQ ID NO 19
<211> LENGTH: 31
<212> TYPE: DNA
<213> ORGANISM: Artificial Sequence
<220> FEATURE:
<223> OTHER INFORMATION: Synthetic aptamer

<400> SEQUENCE: 19
guggacuaua ccgcguaaug cugccuccac t                                 31

<210> SEQ ID NO 20
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'-Fluoro uridine
```

-continued

```
<220> FEATURE:
<221> NAME/KEY: misc_feature
<222> LOCATION: (3)..(6)
<223> OTHER INFORMATION: RNA 2'OH
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro cytidine
<220> FEATURE:
<221> NAME/KEY: modified_base
<222> LOCATION: (9)..(9)
<223> OTHER INFORMATION: 2'-Fluoro uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'-Fluoro uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'-Fluoro cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro cytidine
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro cytidine
<220> FEATURE:
<221> NAME/KEY: modified_base
<222> LOCATION: (24)..(24)
<223> OTHER INFORMATION: 2'-Fluoro uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro cytidine
<220> FEATURE:
<221> NAME/KEY: modified_base
<222> LOCATION: (28)..(28)
```

```
<223> OTHER INFORMATION: 2'-Fluoro uridine
<220> FEATURE:
<221> NAME/KEY: modified_base
<222> LOCATION: (29)..(32)
<223> OTHER INFORMATION: 2'-Fluoro cytidine
<220> FEATURE:
<221> NAME/KEY: misc_feature
<222> LOCATION: (30)..(33)
<223> OTHER INFORMATION: RNA 2'OH
<220> FEATURE:
<221> NAME/KEY: modified_base
<222> LOCATION: (34)..(34)
<223> OTHER INFORMATION: 2'-Fluoro uridine
<220> FEATURE:
<221> NAME/KEY: modified_base
<222> LOCATION: (35)..(35)
<223> OTHER INFORMATION: inverted 2'H Thymidine

<400> SEQUENCE: 20
auggggacua uaccgcguaa ugcugccucc ccaut                              35

<210> SEQ ID NO 21
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl Adenine
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: modified_base
<222> LOCATION: (3)..(6)
<223> OTHER INFORMATION: 2'-O-methyl Guanine
<220> FEATURE:
<221> NAME/KEY: modified_base
<222> LOCATION: (7)..(7)
<223> OTHER INFORMATION: 2'-O-methyl Adenine
<220> FEATURE:
<221> NAME/KEY: modified_base
<222> LOCATION: (8)..(8)
<223> OTHER INFORMATION: 2'-Fluoro Cytidine
<220> FEATURE:
<221> NAME/KEY: modified_base
<222> LOCATION: (9)..(9)
<223> OTHER INFORMATION: 2'-Fluoro Uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'-Fluoro Uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'-Fluoro cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro cytidine
<220> FEATURE:
<221> NAME/KEY: misc_feature
```

```
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(32)
<223> OTHER INFORMATION: 2'Fluoro Cytidine
<220> FEATURE:
<221> NAME/KEY: modified_base
<222> LOCATION: (33)..(33)
<223> OTHER INFORMATION: 2'-O-methyl Adenine
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymine

<400> SEQUENCE: 21
auggggacua uaccgcguaa ugcugccucc ccaut           35

<210> SEQ ID NO 22
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: misc_feature
<222> LOCATION: (3)..(6)
<223> OTHER INFORMATION: RNA 2'OH
<220> FEATURE:
```

```
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'Fluoro Cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: modified_base
<222> LOCATION: (10)..(10)
<223> OTHER INFORMATION: 2'-O-methyl Adenine
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: modified_base
<222> LOCATION: (12)..(12)
<223> OTHER INFORMATION: 2'-O-methyl Adenine
<220> FEATURE:
<221> NAME/KEY: modified_base
<222> LOCATION: (13)..(14)
<223> OTHER INFORMATION: 2'Fluoro Cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro Cytidine
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro Cytidine
```

```
<220> FEATURE:
<221> NAME/KEY: modified_base
<222> LOCATION: (31)..(32)
<223> OTHER INFORMATION: 2'Fluoro Cytidine
<220> FEATURE:
<221> NAME/KEY: misc_feature
<222> LOCATION: (33)..(33)
<223> OTHER INFORMATION: RNA 2'OH
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 22 augggacua uaccgcguaa ugcugccucc ccaut          35

<210> SEQ ID NO 23
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: misc_feature
<222> LOCATION: (3)..(7)
<223> OTHER INFORMATION: RNA 2'OH
<220> FEATURE:
<221> NAME/KEY: modified_base
<222> LOCATION: (8)..(8)
<223> OTHER INFORMATION: 2'Fluoro cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'Fluoro cytidine
<220> FEATURE:
<221> NAME/KEY: modified_base
<222> LOCATION: (15)..(15)
<223> OTHER INFORMATION: 2'-O-methyl Guanine
<220> FEATURE:
<221> NAME/KEY: modified_base
<222> LOCATION: (16)..(16)
<223> OTHER INFORMATION: 2'Fluoro cytidine
<220> FEATURE:
<221> NAME/KEY: modified_base
<222> LOCATION: (17)..(17)
<223> OTHER INFORMATION: 2'-O-methyl Guanine
<220> FEATURE:
<221> NAME/KEY: modified_base
<222> LOCATION: (18)..(18)
```

```
<223> OTHER INFORMATION: 2'Fluoro Uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'Fluoro cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: modified_base
<222> LOCATION: (25)..(25)
<223> OTHER INFORMATION: 2'-O-methyl Guanine
<220> FEATURE:
<221> NAME/KEY: modified_base
<222> LOCATION: (26)..(27)
<223> OTHER INFORMATION: 2'Fluoro cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro cytidine
<220> FEATURE:
<221> NAME/KEY: modified_base
<222> LOCATION: (31)..(32)
<223> OTHER INFORMATION: 2'Fluoro cytidine
<220> FEATURE:
<221> NAME/KEY: misc_feature
<222> LOCATION: (33)..(33)
<223> OTHER INFORMATION: RNA 2'OH
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 23 augggacua uaccgcguaa ugcugccucc ccaut                             35

<210> SEQ ID NO 24
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: misc_feature
<222> LOCATION: (3)..(7)
<223> OTHER INFORMATION: RNA 2'OH
<220> FEATURE:
<221> NAME/KEY: modified_base
```

-continued

```
<222> LOCATION: (8)..(8)
<223> OTHER INFORMATION: 2'Fluoro Cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'Fluoro Cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro Cytidine
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: modified_base
<222> LOCATION: (19)..(20)
<223> OTHER INFORMATION: 2'-O-methyl Adenine
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: modified_base
<222> LOCATION: (22)..(22)
<223> OTHER INFORMATION: 2'-O-methyl Guanine
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro Cytidine
<220> FEATURE:
<221> NAME/KEY: modified_base
<222> LOCATION: (31)..(32)
<223> OTHER INFORMATION: 2'Fluoro Cytidine
<220> FEATURE:
```

```
<221> NAME/KEY: misc_feature
<222> LOCATION: (33)..(33)
<223> OTHER INFORMATION: RNA 2'OH
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 24
auggggacua uaccgcguaa ugcugccucc ccaut                            35

<210> SEQ ID NO 25
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl Adenine
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: modified_base
<222> LOCATION: (3)..(6)
<223> OTHER INFORMATION: 2'-O-methyl Guanine
<220> FEATURE:
<221> NAME/KEY: modified_base
<222> LOCATION: (7)..(7)
<223> OTHER INFORMATION: 2'-O-methyl Adenine
<220> FEATURE:
<221> NAME/KEY: modified_base
<222> LOCATION: (8)..(8)
<223> OTHER INFORMATION: 2'Fluoro Cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: modified_base
<222> LOCATION: (10)..(10)
<223> OTHER INFORMATION: 2'-O-methyl Adenine
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: modified_base
<222> LOCATION: (12)..(12)
<223> OTHER INFORMATION: 2'-O-methyl Adenine
<220> FEATURE:
<221> NAME/KEY: modified_base
<222> LOCATION: (13)..(14)
<223> OTHER INFORMATION: 2'Fluoro Cytidine
<220> FEATURE:
<221> NAME/KEY: modified_base
<222> LOCATION: (15)..(15)
<223> OTHER INFORMATION: 2'-O-methyl Guanine
<220> FEATURE:
<221> NAME/KEY: modified_base
<222> LOCATION: (16)..(16)
<223> OTHER INFORMATION: 2'Fluoro Cytidine
<220> FEATURE:
<221> NAME/KEY: modified_base
<222> LOCATION: (17)..(17)
<223> OTHER INFORMATION: 2'-O-methyl Guanine
<220> FEATURE:
<221> NAME/KEY: modified_base
<222> LOCATION: (18)..(18)
<223> OTHER INFORMATION: 2'Fluoro Uridine
```

```
<220> FEATURE:
<221> NAME/KEY: modified_base
<222> LOCATION: (19)..(20)
<223> OTHER INFORMATION: 2'-O-methyl Adenine
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: modified_base
<222> LOCATION: (22)..(22)
<223> OTHER INFORMATION: 2'-O-methyl Guanine
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: modified_base
<222> LOCATION: (25)..(25)
<223> OTHER INFORMATION: 2'-O-methyl Guanine
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro Cytidine
<220> FEATURE:
<221> NAME/KEY: modified_base
<222> LOCATION: (31)..(32)
<223> OTHER INFORMATION: 2'Fluoro Cytidine
<220> FEATURE:
<221> NAME/KEY: modified_base
<222> LOCATION: (33)..(33)
<223> OTHER INFORMATION: 2'-O-methyl Adenine
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 25
auggggacua uaccgcguaa ugcugccucc ccaut                              35

<210> SEQ ID NO 26
<211> LENGTH: 29
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-O-methyl Guanine
<220> FEATURE:
<221> NAME/KEY: modified_base
<222> LOCATION: (4)..(4)
<223> OTHER INFORMATION: 2'-O-methyl Adenine
<220> FEATURE:
<221> NAME/KEY: modified_base
<222> LOCATION: (5)..(5)
<223> OTHER INFORMATION: 2'-Fluoro Cytidine
<220> FEATURE:
<221> NAME/KEY: modified_base
<222> LOCATION: (6)..(6)
```

```
<223> OTHER INFORMATION: 2'-Fluoro Uracil
<220> FEATURE:
<221> NAME/KEY: modified_base
<222> LOCATION: (7)..(7)
<223> OTHER INFORMATION: 2'-O-methyl Adenine
<220> FEATURE:
<221> NAME/KEY: modified_base
<222> LOCATION: (8)..(8)
<223> OTHER INFORMATION: 2'-Fluoro Uracil
<220> FEATURE:
<221> NAME/KEY: modified_base
<222> LOCATION: (9)..(9)
<223> OTHER INFORMATION: 2'-O-methyl Adenine
<220> FEATURE:
<221> NAME/KEY: modified_base
<222> LOCATION: (10)..(10)
<223> OTHER INFORMATION: 2'-Fluoro Cytidine
<220> FEATURE:
<221> NAME/KEY: modified_base
<222> LOCATION: (11)..(11)
<223> OTHER INFORMATION: 2'-Fluoro Cytidine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(13)
<223> OTHER INFORMATION: 2'-Fluoro Cytidine
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro Uracil
<220> FEATURE:
<221> NAME/KEY: misc_feature
<222> LOCATION: (16)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro Uracil
<220> FEATURE:
<221> NAME/KEY: misc_feature
<222> LOCATION: (19)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro Cytidine
<220> FEATURE:
<221> NAME/KEY: modified_base
<222> LOCATION: (21)..(21)
<223> OTHER INFORMATION: 2'-Fluoro Uracil
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(24)
<223> OTHER INFORMATION: 2'-Fluoro Cytidine
<220> FEATURE:
<221> NAME/KEY: modified_base
<222> LOCATION: (25)..(25)
<223> OTHER INFORMATION: 2'-O-methyl Uracil
<220> FEATURE:
<221> NAME/KEY: modified_base
<222> LOCATION: (26)..(28)
<223> OTHER INFORMATION: 2'-O-methyl Cytosine
<220> FEATURE:
<221> NAME/KEY: modified_base
<222> LOCATION: (29)..(29)
<223> OTHER INFORMATION: inverted 2'H T

<400> SEQUENCE: 26
```
gggacuauac cgcguaaugc ugccuccct                                                29

<210> SEQ ID NO 27
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'-Fluoro C
<220> FEATURE:
<221> NAME/KEY: modified_base
<222> LOCATION: (7)..(7)
<223> OTHER INFORMATION: 2'-Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'-Fluoro C
<220> FEATURE:
<221> NAME/KEY: misc_feature
<222> LOCATION: (13)..(13)
<223> OTHER INFORMATION: RNA 2'OH
<220> FEATURE:
<221> NAME/KEY: modified_base
<222> LOCATION: (14)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro U
<220> FEATURE:
<221> NAME/KEY: misc_feature
<222> LOCATION: (17)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: misc_feature
<222> LOCATION: (20)..(20)
<223> OTHER INFORMATION: RNA 2'OH
<220> FEATURE:

```
<221> NAME/KEY: modified_base
<222> LOCATION: (21)..(21)
<223> OTHER INFORMATION: 2'-Fluoro C
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-O-methyl U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 27
guggacuaua ccgcguaaug cugccuccac t                                    31

<210> SEQ ID NO 28
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl A
<220> FEATURE:
<221> NAME/KEY: modified_base
<222> LOCATION: (3)..(3)
<223> OTHER INFORMATION: 2'-O-methyl U
<220> FEATURE:
<221> NAME/KEY: modified_base
<222> LOCATION: (4)..(5)
<223> OTHER INFORMATION: 2'-O-methyl G
<220> FEATURE:
<221> NAME/KEY: modified_base
<222> LOCATION: (6)..(6)
<223> OTHER INFORMATION: 2'-O-methyl A
<220> FEATURE:
<221> NAME/KEY: modified_base
<222> LOCATION: (7)..(7)
<223> OTHER INFORMATION: 2'-Fluoro C
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
```

```
<220> FEATURE:
<221> NAME/KEY: modified_base
<222> LOCATION: (10)..(10)
<223> OTHER INFORMATION: 2'-Fluoro U
<220> FEATURE:
<221> NAME/KEY: modified_base
<222> LOCATION: (11)..(11)
<223> OTHER INFORMATION: 2'-O-methyl A
<220> FEATURE:
<221> NAME/KEY: modified_base
<222> LOCATION: (12)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro C
<220> FEATURE:
<221> NAME/KEY: misc_feature
<222> LOCATION: (16)..(16)
<223> OTHER INFORMATION: RNA 2'OH
<220> FEATURE:
<221> NAME/KEY: modified_base
<222> LOCATION: (17)..(17)
<223> OTHER INFORMATION: 2'-Fluoro U
<220> FEATURE:
<221> NAME/KEY: misc_feature
<222> LOCATION: (18)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro U
<220> FEATURE:
<221> NAME/KEY: misc_feature
<222> LOCATION: (21)..(21)
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro C
<220> FEATURE:
<221> NAME/KEY: modified_base
<222> LOCATION: (23)..(23)
<223> OTHER INFORMATION: 2'-Fluoro U
<220> FEATURE:
<221> NAME/KEY: misc_feature
<222> LOCATION: (24)..(24)
<223> OTHER INFORMATION: RNA 2'OH
<220> FEATURE:
<221> NAME/KEY: modified_base
<222> LOCATION: (25)..(26)
<223> OTHER INFORMATION: 2'-Fluoro C
<220> FEATURE:
<221> NAME/KEY: modified_base
<222> LOCATION: (27)..(27)
<223> OTHER INFORMATION: 2'-O-methyl U
<220> FEATURE:
<221> NAME/KEY: modified_base
<222> LOCATION: (28)..(29)
<223> OTHER INFORMATION: 2'-O-methyl C
<220> FEATURE:
<221> NAME/KEY: modified_base
<222> LOCATION: (30)..(30)
<223> OTHER INFORMATION: 2'-O-methyl A
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
```

-continued

<223> OTHER INFORMATION: inverted 2'H T

<400> SEQUENCE: 28
gauggacuau accgcguaau gcugccucca uct          33

<210> SEQ ID NO 29
<211> LENGTH: 29
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl C
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(5)
<223> OTHER INFORMATION: 2'-Fluoro C
<220> FEATURE:
<221> NAME/KEY: modified_base
<222> LOCATION: (6)..(6)
<223> OTHER INFORMATION: 2'-Fluoro U
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro C
<220> FEATURE:
<221> NAME/KEY: modified_base
<222> LOCATION: (11)..(11)
<223> OTHER INFORMATION: 2'-Fluoro C
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro U
<220> FEATURE:
<221> NAME/KEY: misc_feature
<222> LOCATION: (16)..(17)
<223> OTHER INFORMATION: RNA 2'OH
<220> FEATURE:
<221> NAME/KEY: modified_base

```
<222> LOCATION: (18)..(18)
<223> OTHER INFORMATION: 2'-Fluoro U
<220> FEATURE:
<221> NAME/KEY: misc_feature
<222> LOCATION: (19)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(24)
<223> OTHER INFORMATION: 2'-Fluoro C
<220> FEATURE:
<221> NAME/KEY: modified_base
<222> LOCATION: (25)..(25)
<223> OTHER INFORMATION: 2'-O-methyl U
<220> FEATURE:
<221> NAME/KEY: modified_base
<222> LOCATION: (26)..(26)
<223> OTHER INFORMATION: 2'-O-methyl C
<220> FEATURE:
<221> NAME/KEY: modified_base
<222> LOCATION: (27)..(27)
<223> OTHER INFORMATION: 2'-O-methyl A
<220> FEATURE:
<221> NAME/KEY: modified_base
<222> LOCATION: (28)..(28)
<223> OTHER INFORMATION: 2'-O-methyl G
<220> FEATURE:
<221> NAME/KEY: modified_base
<222> LOCATION: (29)..(29)
<223> OTHER INFORMATION: inverted 2'H T

<400> SEQUENCE: 29
cugacuauac cgcguaaugc ugccucagt                                      29

<210> SEQ ID NO 30
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(2)
<223> OTHER INFORMATION: 2'-O-methyl C
<220> FEATURE:
<221> NAME/KEY: modified_base
<222> LOCATION: (3)..(3)
<223> OTHER INFORMATION: 2'-O-methyl U
<220> FEATURE:
<221> NAME/KEY: modified_base
<222> LOCATION: (4)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'-Fluoro C
<220> FEATURE:
<221> NAME/KEY: modified_base
<222> LOCATION: (7)..(7)
<223> OTHER INFORMATION: 2'-Fluoro U
<220> FEATURE:
```

```
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'-Fluoro C
<220> FEATURE:
<221> NAME/KEY: misc_feature
<222> LOCATION: (13)..(13)
<223> OTHER INFORMATION: RNA 2'OH
<220> FEATURE:
<221> NAME/KEY: modified_base
<222> LOCATION: (14)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro U
<220> FEATURE:
<221> NAME/KEY: misc_feature
<222> LOCATION: (17)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: misc_feature
<222> LOCATION: (20)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro C
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-O-methyl U
<220> FEATURE:
<221> NAME/KEY: modified_base
<222> LOCATION: (27)..(27)
<223> OTHER INFORMATION: 2'-O-methyl C
<220> FEATURE:
<221> NAME/KEY: modified_base
<222> LOCATION: (28)..(28)
<223> OTHER INFORMATION: 2'-O-methyl A
<220> FEATURE:
<221> NAME/KEY: modified_base
<222> LOCATION: (29)..(30)
<223> OTHER INFORMATION: 2'-O-methyl G
<220> FEATURE:
<221> NAME/KEY: modified_base
<222> LOCATION: (31)..(31)
<223> OTHER INFORMATION: inverted 2'H T
```

<400> SEQUENCE: 30
ccugacuaua ccgcguaaug cugccucagg t                                    31

<210> SEQ ID NO 31
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl C
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl C
<220> FEATURE:
<221> NAME/KEY: modified_base
<222> LOCATION: (4)..(4)
<223> OTHER INFORMATION: 2'-O-methyl U
<220> FEATURE:
<221> NAME/KEY: modified_base
<222> LOCATION: (5)..(5)
<223> OTHER INFORMATION: 2'-O-methyl G
<220> FEATURE:
<221> NAME/KEY: modified_base
<222> LOCATION: (6)..(6)
<223> OTHER INFORMATION: 2'-O-methyl A
<220> FEATURE:
<221> NAME/KEY: modified_base
<222> LOCATION: (7)..(7)
<223> OTHER INFORMATION: 2'-Fluoro C
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro U
<220> FEATURE:
<221> NAME/KEY: modified_base
<222> LOCATION: (11)..(11)
<223> OTHER INFORMATION: 2'-O-methyl A
<220> FEATURE:
<221> NAME/KEY: modified_base
<222> LOCATION: (12)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro C
<220> FEATURE:
<221> NAME/KEY: misc_feature
<222> LOCATION: (16)..(16)
<223> OTHER INFORMATION: RNA 2'OH
<220> FEATURE:
<221> NAME/KEY: modified_base
<222> LOCATION: (17)..(17)
<223> OTHER INFORMATION: 2'-Fluoro U
<220> FEATURE:
<221> NAME/KEY: misc_feature
<222> LOCATION: (18)..(19)

```
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro U
<220> FEATURE:
<221> NAME/KEY: misc_feature
<222> LOCATION: (21)..(21)
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro C
<220> FEATURE:
<221> NAME/KEY: modified_base
<222> LOCATION: (23)..(23)
<223> OTHER INFORMATION: 2'-Fluoro U
<220> FEATURE:
<221> NAME/KEY: misc_feature
<222> LOCATION: (24)..(24)
<223> OTHER INFORMATION: RNA 2'OH
<220> FEATURE:
<221> NAME/KEY: modified_base
<222> LOCATION: (25)..(26)
<223> OTHER INFORMATION: 2'-Fluoro C
<220> FEATURE:
<221> NAME/KEY: modified_base
<222> LOCATION: (27)..(27)
<223> OTHER INFORMATION: 2'-O-methyl U
<220> FEATURE:
<221> NAME/KEY: modified_base
<222> LOCATION: (28)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl G
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl G
<220> FEATURE:
<221> NAME/KEY: modified_base
<222> LOCATION: (33)..(33)
<223> OTHER INFORMATION: inverted 2'H T

<400> SEQUENCE: 31
cucugacuau accgcguaau gcugccucag agt                           33

<210> SEQ ID NO 32
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl A
<220> FEATURE:
<221> NAME/KEY: modified_base
<222> LOCATION: (2)..(2)
<223> OTHER INFORMATION: 2'-Fluoro U
<220> FEATURE:
<221> NAME/KEY: modified_base
<222> LOCATION: (3)..(6)
<223> OTHER INFORMATION: 2'-O-methyl G
<220> FEATURE:
<221> NAME/KEY: modified_base
```

```
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(32)
<223> OTHER INFORMATION: 2'-Fluoro C
<220> FEATURE:
```

```
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-Fluoro U
<220> FEATURE:
<221> NAME/KEY: modified_base
<222> LOCATION: (35)..(35)
<223> OTHER INFORMATION: inverted 2'H T

<400> SEQUENCE: 32
auggggacua uaccgcguaa ugcugccucc ccaut                              35

<210> SEQ ID NO 33
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl A
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
```

```
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-O-methyl U
<220> FEATURE:
<221> NAME/KEY: modified_base
<222> LOCATION: (29)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl U
<220> FEATURE:
<221> NAME/KEY: modified_base
<222> LOCATION: (35)..(35)
<223> OTHER INFORMATION: inverted 2'H T

<400> SEQUENCE: 33
auggggacua uaccgcguaa ugcugccucc ccaut                              35

<210> SEQ ID NO 34
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-Fluoro U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
```

```
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
```

```
<222> LOCATION: (29)..(30)
<223> OTHER INFORMATION: 2'-Fluoro C
<220> FEATURE:
<221> NAME/KEY: modified_base
<222> LOCATION: (31)..(31)
<223> OTHER INFORMATION: 2'-Fluoro U
<220> FEATURE:
<221> NAME/KEY: modified_base
<222> LOCATION: (32)..(32)
<223> OTHER INFORMATION: 2'-Fluoro C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-Fluoro C
<220> FEATURE:
<221> NAME/KEY: modified_base
<222> LOCATION: (35)..(35)
<223> OTHER INFORMATION: inverted 2'H T

<400> SEQUENCE: 34
gugaggacua uaccgcguaa ugcugccucc ucact                                35

<210> SEQ ID NO 35
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-Fluoro U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
```

```
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-Fluoro C
<220> FEATURE:
<221> NAME/KEY: modified_base
<222> LOCATION: (31)..(31)
<223> OTHER INFORMATION: 2'-Fluoro U
<220> FEATURE:
<221> NAME/KEY: modified_base
<222> LOCATION: (32)..(32)
<223> OTHER INFORMATION: 2'-Fluoro C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-Fluoro C
<220> FEATURE:
<221> NAME/KEY: modified_base
<222> LOCATION: (35)..(35)
<223> OTHER INFORMATION: inverted 2'H T

<400> SEQUENCE: 35
gugaggacua uaccgcguaa ugcugccucc ucact                    35
```

```
<210> SEQ ID NO 36
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
```

```
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 36
gugaggacua uaccgcguaa ugcugccucc ucact                                35

<210> SEQ ID NO 37
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
```

```
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-O-methyl U
<220> FEATURE:
```

```
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 37
gugaggacua uaccgcguaa ugcugccucc ucact                           35

<210> SEQ ID NO 38
<211> LENGTH: 29
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-O-methyl G
<220> FEATURE:
<221> NAME/KEY: misc_feature
<222> LOCATION: (4)..(4)
<223> OTHER INFORMATION: RNA 2'OH
<220> FEATURE:
<221> NAME/KEY: modified_base
<222> LOCATION: (5)..(5)
<223> OTHER INFORMATION: 2'-Fluoro C
<220> FEATURE:
<221> NAME/KEY: modified_base
<222> LOCATION: (6)..(6)
<223> OTHER INFORMATION: 2'-Fluoro U
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(11)
<223> OTHER INFORMATION: 2'-Fluoro C
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
```

```
<220> FEATURE:
<221> NAME/KEY: modified_base
<222> LOCATION: (15)..(15)
<223> OTHER INFORMATION: 2'-Fluoro U
<220> FEATURE:
<221> NAME/KEY: misc_feature
<222> LOCATION: (16)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(24)
<223> OTHER INFORMATION: 2'-Fluoro C
<220> FEATURE:
<221> NAME/KEY: modified_base
<222> LOCATION: (25)..(25)
<223> OTHER INFORMATION: 2'-Fluoro U
<220> FEATURE:
<221> NAME/KEY: modified_base
<222> LOCATION: (26)..(28)
<223> OTHER INFORMATION: 2'-O-methyl C
<220> FEATURE:
<221> NAME/KEY: modified_base
<222> LOCATION: (29)..(29)
<223> OTHER INFORMATION: inverted 2'H

<400> SEQUENCE: 38
gggacuauac cgcguaaugc ugccuccct                                    29

<210> SEQ ID NO 39
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl g
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl g
<220> FEATURE:
<221> NAME/KEY: misc_feature
<222> LOCATION: (5)..(5)
<223> OTHER INFORMATION: RNA 2'OH
<220> FEATURE:
<221> NAME/KEY: modified_base
<222> LOCATION: (6)..(6)
<223> OTHER INFORMATION: 2'-Fluoro C
<220> FEATURE:
<221> NAME/KEY: modified_base
<222> LOCATION: (7)..(7)
```

```
<223> OTHER INFORMATION: 2'-Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'-Fluoro C
<220> FEATURE:
<221> NAME/KEY: misc_feature
<222> LOCATION: (13)..(13)
<223> OTHER INFORMATION: RNA 2'OH
<220> FEATURE:
<221> NAME/KEY: modified_base
<222> LOCATION: (14)..(14)
<223> OTHER INFORMATION: 2'-Fluoro C
<220> FEATURE:
<221> NAME/KEY: modified_base
<222> LOCATION: (16)..(16)
<223> OTHER INFORMATION: 2'-Fluoro U
<220> FEATURE:
<221> NAME/KEY: misc_feature
<222> LOCATION: (17)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: misc_feature
<222> LOCATION: (20)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro C
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H

<400> SEQUENCE: 39
```
guggacuaua ccgcguaaug cugccuccac t    31

<210> SEQ ID NO 40
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl A
<220> FEATURE:
<221> NAME/KEY: modified_base
<222> LOCATION: (3)..(3)
<223> OTHER INFORMATION: 2'-O-methyl U
<220> FEATURE:
<221> NAME/KEY: modified_base
<222> LOCATION: (4)..(5)
<223> OTHER INFORMATION: 2'-O-methyl G
<220> FEATURE:
<221> NAME/KEY: misc_feature
<222> LOCATION: (6)..(6)
<223> OTHER INFORMATION: RNA 2'OH
<220> FEATURE:
<221> NAME/KEY: modified_base
<222> LOCATION: (7)..(7)
<223> OTHER INFORMATION: 2'-Fluoro C
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro U
<220> FEATURE:
<221> NAME/KEY: modified_base
<222> LOCATION: (11)..(11)
<223> OTHER INFORMATION: 2'-O-methyl A
<220> FEATURE:
<221> NAME/KEY: modified_base
<222> LOCATION: (12)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro C
<220> FEATURE:
<221> NAME/KEY: misc_feature
<222> LOCATION: (16)..(16)
<223> OTHER INFORMATION: RNA 2'OH
<220> FEATURE:
<221> NAME/KEY: modified_base
<222> LOCATION: (17)..(17)
<223> OTHER INFORMATION: 2'-Fluoro U
<220> FEATURE:
<221> NAME/KEY: misc_feature
<222> LOCATION: (18)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro U
<220> FEATURE:

```
<221> NAME/KEY: misc_feature
<222> LOCATION: (21)..(21)
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro C
<220> FEATURE:
<221> NAME/KEY: modified_base
<222> LOCATION: (23)..(23)
<223> OTHER INFORMATION: 2'-Fluoro U
<220> FEATURE:
<221> NAME/KEY: misc_feature
<222> LOCATION: (24)..(24)
<223> OTHER INFORMATION: RNA 2'OH
<220> FEATURE:
<221> NAME/KEY: modified_base
<222> LOCATION: (25)..(26)
<223> OTHER INFORMATION: 2'-Fluoro C
<220> FEATURE:
<221> NAME/KEY: modified_base
<222> LOCATION: (27)..(27)
<223> OTHER INFORMATION: 2'-Fluoro U
<220> FEATURE:
<221> NAME/KEY: modified_base
<222> LOCATION: (28)..(29)
<223> OTHER INFORMATION: 2'-O-methyl C
<220> FEATURE:
<221> NAME/KEY: modified_base
<222> LOCATION: (30)..(30)
<223> OTHER INFORMATION: 2'-O-methyl A
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 40
gauggacuau accgcguaau gcugccucca uct                               33

<210> SEQ ID NO 41
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
```

```
-continued

<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
```

```
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 41
gugaggacua uaccgcguaa ugcugccucc ucact                                    35

<210> SEQ ID NO 42
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
```

```
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 42
gugaggacua uaccgcguaa ugcugccucc ucact                                    35

<210> SEQ ID NO 43
<211> LENGTH: 35
<212> TYPE: DNA
```

```
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
```

```
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 43
gugaggacua uaccgcguaa ugcugccucc ucact                    35

<210> SEQ ID NO 44
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
```

```
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
```

```
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 44
gugaggacua uaccgcguaa ugcugccucc ucact                              35

<210> SEQ ID NO 45
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
```

```
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 45
gugaggacua uaccgcguaa ugcugccucc ucact                          35

<210> SEQ ID NO 46
<211> LENGTH: 33
```

```
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl A
<220> FEATURE:
<221> NAME/KEY: misc_feature
<222> LOCATION: (18)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: misc_feature
<222> LOCATION: (21)..(21)
```

```
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 46
gugaggacua uaccgcaauc gugccuccuc act                                    33

<210> SEQ ID NO 47
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
```

```
<222> LOCATION: (8)..(8)
<223> OTHER INFORMATION: 2'Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'Fluoro C
<220> FEATURE:
<221> NAME/KEY: modified_base
<222> LOCATION: (21)..(21)
<223> OTHER INFORMATION: 2'-O-methyl G
<220> FEATURE:
<221> NAME/KEY: modified_base
<222> LOCATION: (22)..(22)
<223> OTHER INFORMATION: 2'Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
```

```
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 47
gugaggacua uaccgcaauc gugccuccuc act                                  33

<210> SEQ ID NO 48
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
```

```
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-O-methyl G
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 48
gugaggacua uaccgcaauc gugccuccuc act                          33

<210> SEQ ID NO 49
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
```

```
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-O-methyl G
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
```

```
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 49
gugaggacua uaccgcaauc gugccuccuc act                              33

<210> SEQ ID NO 50
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-Methyl-A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: misc_feature
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
```

```
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'Fluoro U
<220> FEATURE:
<221> NAME/KEY: misc_feature
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 50
gugaggacua uaccgcguaa ugcugccucc ucact                    35
```

<210> SEQ ID NO 51
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-O-methyl C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)

-continued

```
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-O-methyl U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(26)
<223> OTHER INFORMATION: 2'-O-methyl C
<220> FEATURE:
<221> NAME/KEY: modified_base
<222> LOCATION: (27)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 51
gugaggacua uaccgcguaa ugcugccucc ucact                                35

<210> SEQ ID NO 52
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
```

```
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-O-methyl C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'Fluoro C
<220> FEATURE:
<221> NAME/KEY: modified_base
<222> LOCATION: (24)..(24)
<223> OTHER INFORMATION: 2'Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
<223> OTHER INFORMATION: 2'Fluoro C
<220> FEATURE:
```

```
<221> NAME/KEY: modified_base
<222> LOCATION: (28)..(28)
<223> OTHER INFORMATION: 2'Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 52
gugaggacua uaccgcguaa ugcugccucc ucact                           35

<210> SEQ ID NO 53
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
```

```
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 5'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
```

<223> OTHER INFORMATION: inverted 2'H T

<400> SEQUENCE: 53
gugaggacua uaccgcguaa ugcugccucc ucact     35

<210> SEQ ID NO 54
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'Fluoro U
<220> FEATURE:
<221> NAME/KEY: modified_base

```
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'Fluoro C
<220> FEATURE:
<221> NAME/KEY: modified_base
<222> LOCATION: (24)..(24)
<223> OTHER INFORMATION: 2'-O-methyl U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(26)
<223> OTHER INFORMATION: 2'-O-methyl C
<220> FEATURE:
<221> NAME/KEY: modified_base
<222> LOCATION: (27)..(27)
<223> OTHER INFORMATION: 2'Fluoro C
<220> FEATURE:
<221> NAME/KEY: modified_base
<222> LOCATION: (28)..(28)
<223> OTHER INFORMATION: 2'Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 54
gugaggacua uaccgcguaa ugcugccucc ucact                        35

<210> SEQ ID NO 55
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
```

```
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
```

```
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 55
guggacuaua ccgcguaaug cugccuccac t                                    31

<210> SEQ ID NO 56
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: misc_feature
<222> LOCATION: (15)..(15)
```

```
<223> OTHER INFORMATION: RNA 2'OH
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'-O-methyl U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(24)
<223> OTHER INFORMATION: 2'-O-methyl C
<220> FEATURE:
<221> NAME/KEY: modified_base
<222> LOCATION: (25)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 56
guggacuaua ccgcguaaug cugccuccac t                                    31

<210> SEQ ID NO 57
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
```

```
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
```

```
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 57
guggacuaua ccgcguaaug cugccuccac t                              31

<210> SEQ ID NO 58
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
```

```
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 58
guggacuaua ccgcguaaug cugccuccac t                              31

<210> SEQ ID NO 59
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
```

```
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'-O-methyl U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(24)
<223> OTHER INFORMATION: 2'-O-methyl C
<220> FEATURE:
<221> NAME/KEY: modified_base
<222> LOCATION: (25)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
```

-continued

```
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 59
guggacuaua ccgcguaaug cugccuccac t                                   31
```

MODULATORS OF COAGULATION FACTORS WITH ENHANCED STABILITY

CROSS-REFERENCE TO RELATED APPLICATIONS

This application is a continuation-in-part of U.S. application Ser. No. 11/113,378, filed Apr. 22, 2005, now U.S. Pat. No. 7,304,041, and claims priority to U.S. Provisional Application No. 60/725,509, filed Oct. 11, 2005.

TECHNICAL FIELD

An improved agent, composition and method to regulate the pharmacological activity of a coagulation factor with nucleic acid ligands (e.g., aptamers) that have improved stability is disclosed.

BACKGROUND

Despite substantial efforts to treat and prevent thrombotic events, arterial thrombosis continues to be the major cause of death in adult populations of developed nations. Although numerous medical strategies exist for treating thrombosis, no available agent meets the therapeutic endpoints of both bioavailability and efficacy, while also having a reasonable safety profile (see Feuerstein et al. (1999) *Arterioscler. Thromb. Vasc. Biol.* 19:2554-2562).

Under normal circumstances, an injury to vascular endothelial cells lining a blood vessel triggers a hemostatic response through a sequence of events commonly referred to as the coagulation "cascade." The cascade culminates in the conversion of soluble fibrinogen to insoluble fibrin which, together with platelets, forms a localized clot or thrombus which prevents extravascular release of blood components. Wound healing can then occur followed by clot dissolution and restoration of blood vessel integrity and flow.

Initiation of blood coagulation arises from two distinct pathways: the intrinsic and extrinsic pathways. The intrinsic pathway can be triggered in vitro by contact of blood borne factors with artificial negatively charged surfaces such as glass. In contrast, the extrinsic pathway can be initiated in vivo or in vitro when tissue factor (TF), normally sequestered from the circulatory system, comes into contact with blood after injury. Blood exposed TF acts as a cofactor for the factor VIIa ("FVIIa") catalyzed activation of factor IX ("FIX") and factor X ("FX"). This leads to rapid formation of FXa and thrombin, which subsequently polymerizes to form the fibrin clot. Both the intrinsic and extrinsic pathways are characterized by the assembly of multiple protein complexes on procoagulant surfaces, which localizes the response to the site of injury (see Mann, K. G. et al. (1990) *Blood* 76:1).

Anticoagulant Therapy

Coumarin drugs, such as warfarin as well as the glycosaminoglycans, heparin and heparan sulfate, are commonly used as anticoagulants. Warfarin, a coumarin derivative, acts by competing with vitamin K dependent post-translational modification of prothrombin and other vitamin K-dependent clotting factors. Its action is somewhat slower and longer lasting effect than heparin. The coumarin drugs inhibit coagulation by inhibiting the vitamin K-dependent carboxylation reactions necessary to the function of thrombin, and factors VII, IX, and X as well as proteins C and S. These drugs act by inhibiting the reduction of the quinone derivatives of vitamin K to their active hydroquinone forms. Because of the mode of action of coumarin drugs, it takes several days for their maximum effect to be realized. Heparin binds to, and activates, antithrombin III which then inhibits the serine proteases of the coagulation cascade. In part due to their potency, heparin and LMW heparin suffer drawbacks. Uncontrolled bleeding is a major complication observed in up to 7% of patients receiving continuous infusion up to 14% of patients given intermittent bolus doses. The therapeutic range to achieve efficacy without placing the patient at risk for bleeding is narrow, approximately 1 to less than 3 ug heparin/ml plasma. At concentrations greater than 4 ug/ml of heparin, clotting activity is not detectable. Thus, great care must be taken to keep the patient's plasma concentrations within the therapeutic range.

Groups have used antibodies to coagulation factors to regulate the coagulation cascade. For example PCT Publication No. WO 03/093422 to Schering Aktiengesellschaft discloses antibodies that bind with greater affinity to the factor VIIa/tissue factor (FVIIa/TF) complex than to tissue factor (TF) alone. These antibodies allegedly do not compete for binding to tissue factor with Factor VII and Factor X, and inhibit FX activation.

U.S. Pat. No. 6,001,820 to Hamilton Civic Hospitals Research Development Inc. provides heparin cofactor II specific catalytic agents which are capable of (1) selectively inactivating thrombin which is bound either to fibrin in a clot or to some other surface, but which has only minimal inhibitory activity against free thrombin; (2) inhibiting the assembly of the intrinsic tenase complex and thereby the activation of Factor X by Factor IXa; and (3) inhibiting the activation of Factor IX by Factor XIa.

Aptamers

Nucleic acids have conventionally been thought of as primarily playing an informational role in biological processes. In the past decade it has become clear that the three dimensional structure of nucleic acids can give them the capacity to interact with and regulate proteins. Such nucleic acid ligands or "aptamers" are short DNA or RNA oligomers which can bind to a given ligand with high affinity and specificity. As a class, the three dimensional structures of aptamers are sufficiently variable to allow aptamers to bind to and act as ligands for virtually any chemical compound, whether monomeric or polymeric. Aptamers have emerged as promising new diagnostic and therapeutic compounds, particularly in cancer therapy and the regulation of blood coagulation.

Nucleic acid ligands can be identified through methods related to a method termed the Systematic Evolution of Ligands by EXponential enrichment (SELEX). SELEX involves selection of protein-binding nucleic acids from a mixture of candidate oligonucleotides and step-wise iterations of binding, partitioning and amplification to achieve the desired criterion of binding affinity and selectivity. The SELEX process was first described by Gold and Tuerk in U.S. Pat. No. 5,475,096, and thereafter in U.S. Pat. No. 5,270,163 (see also WO 91/19813; Tuerk et al. (1990) *Science* 249:505-10).

A number of third parties have applied for and secured patents covering the identification, manufacture and use of aptamers. As stated above, Gold and Tuerk are generally credited with first developing the SELEX method for isolating aptamers, and their method is described in a number of United States patents including U.S. Pat. Nos. 5,670,637, 5,696,249, 5,843,653, 6,110,900, and 5,270,163. Thomas Bruice et al. reported a process for producing aptamers in U.S. Pat. No. 5,686,242, which differs from the original SELEX process reported by Tuerk and Gold because it employs strictly random oligonucleotides during the screening sequence. The oligonucleotides screened in the '242 patent lack the oligonucleotide primers that are present in oligonucleotides screened in the SELEX process.

Several patents to Gold et al. contain claims covering aptamers to thrombin. For example, U.S. Pat. No. 5,670,637 contains claims covering aptamers that bind to proteins. U.S. Pat. No. 5,696,249 claims an aptamer produced by the SELEX process. U.S. Pat. Nos. 5,756,291 and 5,582,981 to O'Toole, disclose and claim a method for detecting thrombin using a labeled aptamer that comprises a defined six nucleotide sequence. U.S. Pat. Nos. 5,476,766 and 6,177,557 disclose compounds and methods to identify nuclei acid ligand solutions to thrombin using SELEX.

Sullenger, Rusconi, Kontos and White in WO 02/26932 describe RNA aptamers that bind to coagulation factors, E2F family transcription factors, Ang1, Ang2, and fragments or peptides thereof, transcription factors, autoimmune antibodies and cell surface receptors useful in the modulation of hemostasis and other biologic events. See also Rusconi et al, Thrombosis and Haemostasis 83:841-848 (2000), White et al, *J Clin Invest* 106:929-34 (2000), Ishizaki et al, *Nat Med* 2:1386-1389 (1996), and Lee et al, *Nat. Biotechnol.* 15:41-45 (1997)).

Modulation of Aptamers

PCT Publication No. WO 02/096926 to Duke University describes agents and methods to modulate the biological activity of nucleic acid ligands through the administration of a modulator. The publication describes aptamers controlled by modulators that can be nucleic acids. The modulatable aptamers are described as being useful in the treatment of diseases in which it is important to inhibit coagulation, elongation factor 2 activity or angiogenesis. The modulatable aptamers to control coagulation include the aptamers to coagulation factors VII or VIIa, VIII or VIIIa, IX or IXa, V or Va, X or Xa, complexes formed with these factors, as well as platelet receptors. The modulator can change the binding of the nucleic acid ligand for its target, degrade or otherwise cleave, metabolize or break down the nucleic acid ligand while the ligand is exerting its effect. Modulators can be administered in real time as needed based on various factors, including the progress of the patient, as well as the physician's discretion in how to achieve optimal therapy.

Maximizing Utility of Aptamers

In order for aptamers to be useful therapeutic reagents, they should bind tightly to proteins, inhibit a specified function of that protein if an antagonist is desired and have no harmful side-effects. Unmodified RNA is not realistically used as a therapeutic agent since blood is rich in ribonucleases. Some modification of single-stranded RNA and DNA can produce molecules which are stable in blood and certain known aptamers have 2'F or 2'NH$_2$ groups within each pyrimidine nucleotide.

However, there is no way to predict how a particular modification changes aptamers. In particular, when additional limitations are required, as is the case with modulatable aptamers, no techniques exist to predict how one or more modifications can affect the capacity of the aptamer to regulate its ligands and at the same time continue to be regulated by antidote binding.

Several methods have been developed that modify the base SELEX process to obtain modified aptamers. For example, patents disclose the use of modified nucleotides in the SELEX process to obtain aptamers that exhibit improved properties. U.S. Pat. No. 5,660,985 provides 2'-modified nucleotides that allegedly display enhanced in vivo stability. U.S. Pat. No. 6,083,696 discloses a "blended" SELEX process in which oligonucleotides covalently linked to non-nucleic acid functional units are screened for their capacity to bind a target molecule. Other patents describe post-SELEX modifications to aptamers to decrease their size, increase their stability, or increase target binding affinity (see, e.g., U.S. Pat. Nos. 5,817,785 and 5,648,214).

In U.S. Pat. No. 5,245,022 Weis et al. disclose an oligonucleotide of about 12-25 bases that is terminally substituted by a polyalkyleneglycol. These modified oligonucleotides are reported to be resistant to exonuclease activity.

U.S. Pat. Nos. 5,670,633 and 6,005,087 to Cook et al. describe thermally stable 2'-fluoro oligonucleotides that are complementary to an RNA or DNA base sequence. U.S. Pat. Nos. 6,222,025 and 5,760,202 to Cook et al. describe the synthesis of 2'-O substituted pyrimidines and oligomers containing the modified pyrimidines. EP 0 593 901 B1 discloses oligonucleotide and ribozyme analogues with terminal 3',3'- and 5',5'-nucleoside bonds. U.S. Pat. No. 6,011,020 to Gold et al. discloses and claims an aptamer modified by polyethylene glycol.

Currently, a strong need remains to provide methods and compositions to treat patients in need of anticoagulant therapy, and in particular, during surgery or other medical intervention.

Therefore, it is an object of the present invention to provide methods and compositions to treat patients in need of anticoagulant therapy, and in particular, during surgery or other medical intervention It is another object of the present invention to provide more control over the therapeutic effect, pharmacokinetics and duration of activity of anticoagulant therapies.

SUMMARY OF THE INVENTION

Improved nucleic acid ligands for anticoagulant therapy are disclosed as well as improved nucleic acid ligands in combination with an antidote that changes the binding of the nucleic acid ligand for its target or that degrades or otherwise cleaves, metabolizes or breaks down the nucleic acid ligand while the ligand is still exerting its effect. These improved aptamers provide favorable anticoagulant properties for in vivo applications, including during human or veterinary surgery. The anticoagulant function of the improved aptamer is conveniently neutralized on administration of its antidote when desired by the surgeon or other medical care specialist. In particular, the aptamers of the invention include additional agents to increase bioavailability and/or decrease degradation of the active agent.

In one aspect of the invention, improved nucleic acid ligands or aptamers to a factor in the blood coagulation cascade are provided that include at least one moiety that increases bioavailability of the agent. In some embodiments, the factors include Factor IX (FIX) or the cleavage product Factor IXa (FIXa). In some embodiments, the aptamers are ligands to the complex formed by FIXa with Factor VIIIa (FVIIIa), also known as the "intrinsic tenase complex." In some embodiments, the aptamers are ligands that inhibit the complex formation between FIXa and FVIIIa. In a subembodiment, the aptamers of the present invention bind to the complex of FIX and FVIIIa and inhibit activation of Factor X (FX). The aptamers can interact with FIX, FIXa or a complex formed with FVIIIa in the presence or absence of additional calcium. The aptamers can also interact with the factors of the complex at a cell membrane. In one embodiment, the aptamers bind to the intrinsic tenase complex at the membrane surface.

In particular, the aptamers, such as aptamers to FIXa, are linked to a stabilizing moiety on at least one terminus. In one embodiment, the aptamers are linked to a polymeric agent. In one embodiment, the aptamers are linked to one or more polyethylene glycol molecules. The aptamer and stabilizing agent can be linked at, for example, a 5' terminus of the nucleic acid sequence. In certain embodiments, the aptamers are linked to multiple polyethylene glycol molecules. In other embodiments, a single polyethylene glycol molecule can be linked to more than one aptamer to provide improved delivery of the agent.

The aptamers of the present invention can be comprised of ribonucleotides or deoxyribonucleotides, or a combination thereof. In general, the improved aptamers are at least 25 nucleotides long, and typically not longer than 35-40 nucleotides long. In one embodiment, aptamers are at least 25, 30, 35, or 40 nucleotides in length. In specific embodiments, the sequence of stem 1 includes 5 nucleotides in the 5'-3' direction. In a subembodiment, stem 1 includes three guanine (G) residues in the 5'-3' direction.

The aptamers can include a "suicide position." In one embodiment, this position becomes single stranded and labile upon binding of the antidote to the improved aptamer and allows for cleavage of the improved aptamer upon binding of the antidote by enzymes in the circulation, such as blood or liver endonucleases, thereby effectively eliminating the active aptamer from circulation. The suicide position can be at a guanine in stem 2 that is hydroxylated. In one embodiment, this nucleotide is in a double stranded configuration until bound with an antidote and becomes single stranded and available for cleavage upon binding of the antidote.

In an embodiment, the aptamers include the nucleotide sequence gugg and the complimentary sequence ccac. In one embodiment, the aptamer to Factor IX comprises the nucleotide sequence: gugga cuauacc gcg uaaugc ugc c uccac t (SeqID 19).

Another embodiment of the invention includes an antidote oligonucleotide paired with the aptamer of the invention. The antidote oligonucleotide can be complementary to at least a portion of the aptamer. The antidote can, for example, comprise the following sequences: (5'-3') sequence: cgcg-guauaguccccau (Apt/AD; SEQ ID NO:1); (5'-3') sequence: cgcgguauagaccc (Apt6/AD; SEQ ID NO:2); (5'-3') sequence: cgcgguauaguccac (Apt7/AD; SEQ ID NO:3); (5'-3') sequence: cgcgguauaguccauc (Apt8/AD; SEQ ID NO:4); (5'-3') sequence: cgcgguauagucag (Apt9/AD; SEQ ID NO:5); (5'-3') sequence: cgcgguauagucagg (Apt10/AD; SEQ ID NO:6); (5'-3') sequence: cgcgguauagucagag (Apt11/AD; SEQ ID NO:7); (5'-3') sequence: cgcgguauaguccucac (Apt14/AD; SEQ ID NO:8), or any modification or derivative thereof. In certain embodiments, the antidote consists essentially of one of the above sequences, or consists entirely of one of the above sequences.

In certain embodiments, the improved aptamer is provided in alternation with an antidote. The antidote sequence does not need to be completely complementary to the improved anticoagulant aptamer as long as the antidote sufficiently binds to or hybridizes to the aptamer to neutralize its activity.

The aptamer pairs of the present invention include the following sequences:

| Aptamer | Antidote |
|---|---|
| augggga cuauacc gcg uaaugc ugc c uccccau t (SEQ ID NO: 9) | cgcgguauaguccccau (SEQ ID NO: 1) |

| Aptamer | Antidote |
|---|---|
| augggga cuauaccgcguaaugcugcc uccccau t (SEQ ID NO: 10) | cgcgguauaguccccau (SEQ ID NO: 1) |
| ggga cuauaccgcguaaugcugcc uccc t (SEQ ID NO: 11) | cgcgguauagaccc (SEQ ID NO: 2) |
| gugga cuauaccgcguaaugcugcc uccac t (SEQ ID NO: 12) | cgcgguauaguccac (SEQ ID NO: 3) |
| gaugga cuauaccgcguaaugcugcc uccauc t (SEQ ID NO: 13) | cgcgguauaguccauc (SEQ ID NO: 4) |
| cuga cuauaccgcguaaugcugcc ucag t (SEQ ID NO: 14) | cgcgguauagucag (SEQ ID NO: 5) |
| ccuga cuauaccgcguaaugcugcc ucagg t (SEQ ID NO: 15) | cgcgguauagucagg (SEQ ID NO: 6) |
| cucuga cuauaccgcguaaugcugcc ucagag t (SEQ ID NO: 16) | cgcgguauagucagag (SEQ ID NO: 7) |
| gugagga cuauaccgcguaaugcugcc uccucac t (SEQ ID NO: 17) | cgcgguauaguccucac (SEQ ID NO: 8) |
| gugagga cuauacc gcg uaaugc ugc c uccucac t (SEQ ID NO: 18) | cgcgguauaguccucac (SEQ ID NO: 8) |
| gugga cuauacc gcg uaaugc ugc c uccac t (SEQ ID NO: 19) | cgcgguauaguccac (SEQ ID NO: 3) |

Improved aptamer-antidote pairs that are more stable and bioactive are developed by including secondary modifications on either the aptamer or antidote or both. In one embodiment, the improved aptamer to Factor IX includes one or more 2'-O-methyl modified nucleotides. In another embodiment, the improved aptamer contains one or more 2'-O-methyl and one or more 2'-fluoro modifications. In another embodiment, the aptamer and antidote contain no 2'-fluoro modifications. In yet another embodiment, the improved aptamer includes one or more 2'-O-methyl and one or more 2'-fluoro modifications on a stem. In one embodiment, at least one guanine in stem 2 of an improved aptamer includes a hydroxyl sugar (2'-OH). In another embodiment, at least one uridine in stem 1 or in stem 2 of the improved aptamer is modified with either a 2'-fluoro or 2'-O-methyl. In another embodiment, at least one cytidine in stem 2 of the improved aptamer is 2'-fluoro modified.

In one embodiment, the aptamer is linked to one or more polyethylene glycol (PEG) molecule. In a specific embodiment, the aptamer is linked to 40 KD PEG using a six carbon amino linker. In a more specific embodiment, the six carbon amino linker is attached to the PEG through an amino acid attachment. In a subembodiment, the PEG is two twenty KD PEG that are attached to one or more amino acid, such as lysine, which is attached to the six carbon amino linker.

In one specific embodiment, the aptamer to Factor IXa is the following structure: 5'-O-[5-[N$^2$-(monomethoxy 20K polyethylene glycol carbamoyl)-N$^6$-(monomethoxy 20K polyethylene glycol carbamoyl)]-lysylamido]hexyl]-2'-methoxy-2'-deoxguanylyl-(3'-5')-2'-methoxy-2'-deoxyuridylyl-(3'-5')-2'-methoxy-2'-deoxyguanylyl-(3'-5')-2'- methoxy-2'-deoxyguanylyl-(3'-5')-2'-methoxy-2'-deoxyadenylyl-(3'-5')-2'-fluoro-2'-deoxycytidylyl-(3'-5')-2'-fluoro-2'-deoxyuridylyl-(3'-5')-2'-methoxy-2'-deoxyadenylyl-(3'-5')-2'-fluoro-2'-deoxyuridylyl-(3'-5')-2'-methoxy-2'-deoxyadenylyl-(3'-5')-2'-fluoro-2'-deoxycytidylyl-(3'-5')-2'-fluoro-2'-deoxycytidylyl-(3'-5')-2'-methoxy-2'-deoxyguanylyl-(3'-5')-2'-fluoro-2'-deoxycytidylyl-(3'-5')-2'-methoxy-2'-deoxyguanylyl-(3'-5')-2'-fluoro-2'-deoxyuridylyl-(3'-5')-2'-methoxy-2'-deoxyadenylyl-(3'-5')-2'-methoxy-2'-deoxyadenylyl-(3'-5')-2'-fluoro-2'-deoxyuridylyl-(3'-5')-2'-methoxy-2'-deoxyguanylyl-(3'-5')-2'-fluoro-2'-deoxycytidylyl-(3'-5')-2'-methoxy-2'-deoxyuridylyl-(3'-5')-riboguanylyl-(3'-5')-2'-methoxy-2'-deoxycytidylyl-(3'-5')-2'-fluoro-2'-deoxycytidylyl-(3'-5')-2'-fluoro-2'-deoxyuridylyl-(3'-5')-2'-methoxy-2'-deoxcytidylyl-(3'-5')-2'-methoxy-2'-deoxytidylyl-(3'-5')-2'-methoxy-2'-deoxyadenylyl-(3'-5')-2'-methoxy-2'-deoxcytidylyl-(3'-3')-thymidine.

In another embodiment, the aptamer to Factor IXa is of the following structure:

In one embodiment, the aptamer to Factor IXa is 10,282.4 Daltons in its protonated form. In another embodiment, the aptamer is in its sodium salt form. In yet another embodiment, the aptamer is PEGylated RB006 and in its sodium salt.

The improved aptamers and antidotes can also include nucleotides that are modified with water-soluble polymers. Such polymers can include a polyethylene glycol, polyamine, polyether, polyanhydride, polyester, or other biodegradable pharmaceutically acceptable polymer.

The invention includes the use of the improved aptamers to bind to FIX, FIXa, or the intrinsic tenase complex. This binding can be in vitro or in vivo. The result of the binding to FIX, FIXa or the tenase complex can be to inhibit the biological activity of the proteins or complex.

In one embodiment, the improved aptamer inhibits blood coagulation by binding to FIXa, which is derived from the same gene product as FIX. The invention includes administering the improved aptamers of the invention to a mammal in need thereof to inhibit blood coagulation. Another embodi-

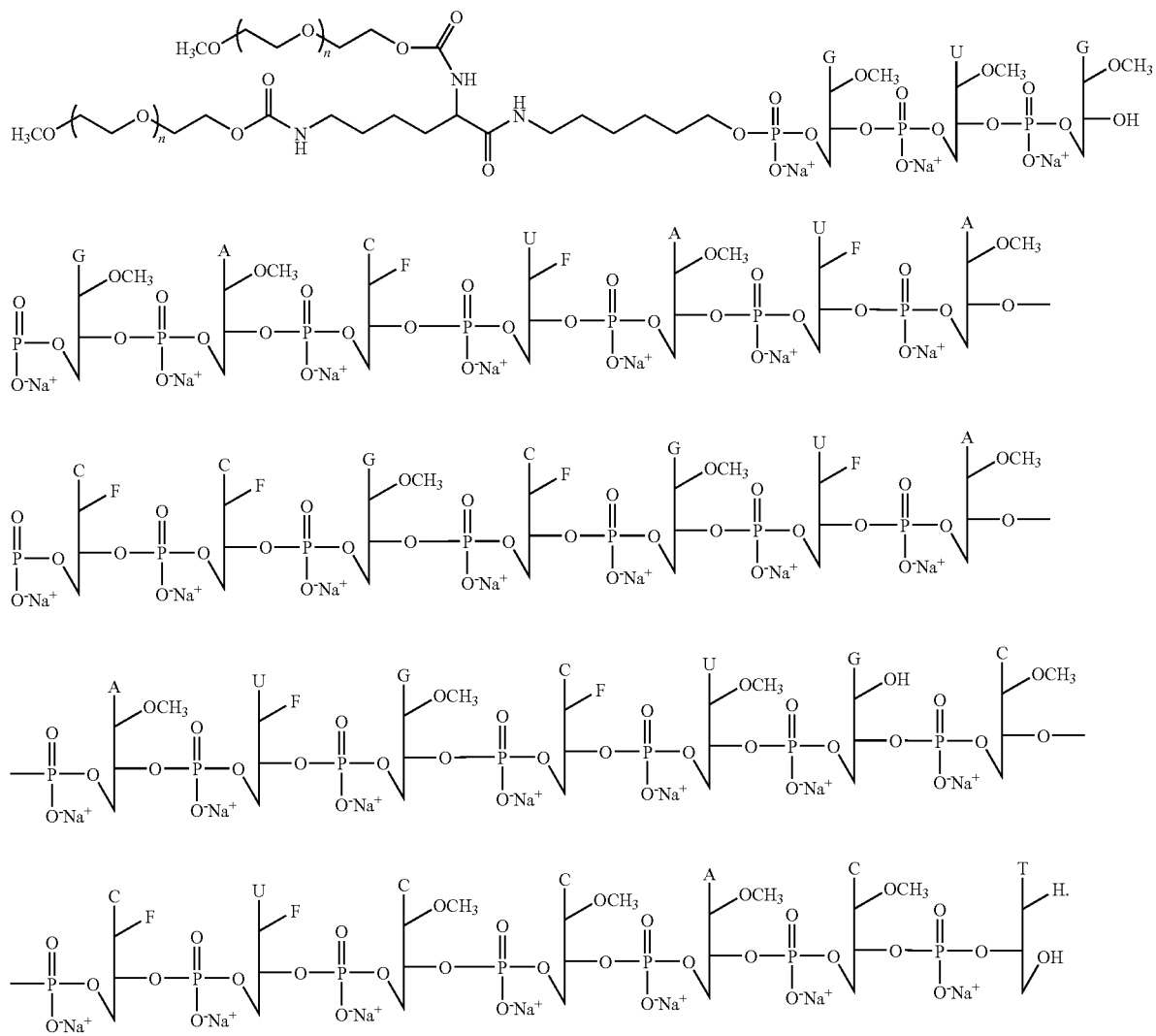

where n is approximately 450 ment of the invention provides methods of using the improved aptamers and antidotes during a therapeutic regime.

In one embodiment, antidotes to the improved aptamers of the invention are provided to a mammal in need thereof to reverse the anticoagulant effects of the improved aptamers. Improved aptamers and aptamer-antidote pairs can be administered in real time as needed based on various factors, including the progress of the patient, as well as the physician's discretion in how to achieve optimal therapy. Thus, this invention discloses an improved regulatable therapeutic regime in the course of nucleic acid ligand therapy for blood coagulation. In one example, an antidote is provide that neutralizes the effect of the improved aptamer to turn off anticoagulant activity when desired by the physician or other health care provider. In another embodiment, the improved aptamers and antidotes to blood coagulation factors are administered in sequential steps, in which the aptamers are administered, the antidotes are used to limit the activity of the improved aptamers, and subsequently the aptamers are re-administered to a patient in need thereof. In one embodiment, the antidote achieves this neutralization effect by binding to or hybridizing to the improved aptamer.

The improved aptamers can be administered to patients suffering from or at risk of suffering from a cardiovascular disease or intervention, including surgical intervention, that causes or results in a coagulation-inducing event. Examples include acute myocardial infarction (heart attack), cerebrovascular accidents (stroke), ischemia, angioplasty, CABG (coronary artery bypass grafts), cardiopulmonary bypass, thrombosis in the circuit of cardiac bypass apparatus and in patients undergoing renal dialysis, unstable angina, pulmonary embolism, deep vein thrombosis, arterial thrombosis, and disseminated intravascular coagulation.

The improved aptamers can also be administered to prevent coagulation-induced inflammation. It appears that early inflammation is induced by activation of the coagulation cascade. Therefore, the improved aptamers can be used to treat cardiovascular diseases that include a inflammatory component, for example, atherosclerosis, acute coronary syndrome (ACS), myocardial infarction which may result in reperfusion injury, or to treat adverse events associated with post-angioplasty restenosis.

BRIEF DESCRIPTION OF THE DRAWINGS

FIG. 1a is a schematic of aptamers Apt A and 1-5. 1b is a schematic of aptamers 6-11. 1c is a schematic of aptamers Apt 12-17. 1d is a schematic of aptamers Apt 18-20, 1e of Apt 21. 1f is a schematic of aptamers Apt 22-29, 1g of Apt 30-34 and 1h of Apt 35-39.

DETAILED DESCRIPTION OF THE INVENTION

1. Definitions

Figure 1:
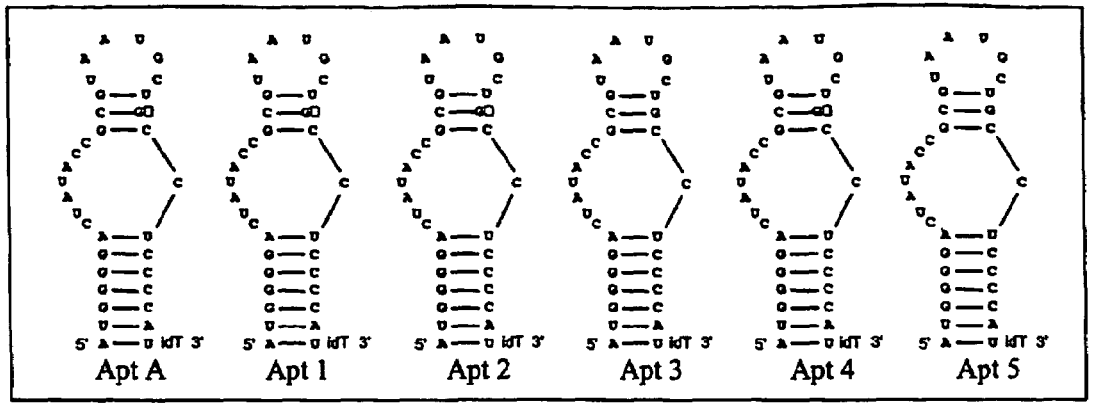
FIG. 1 is a schematic of proposed two dimensional configurations of Apt A, 1-39 described below.
Figure 1:
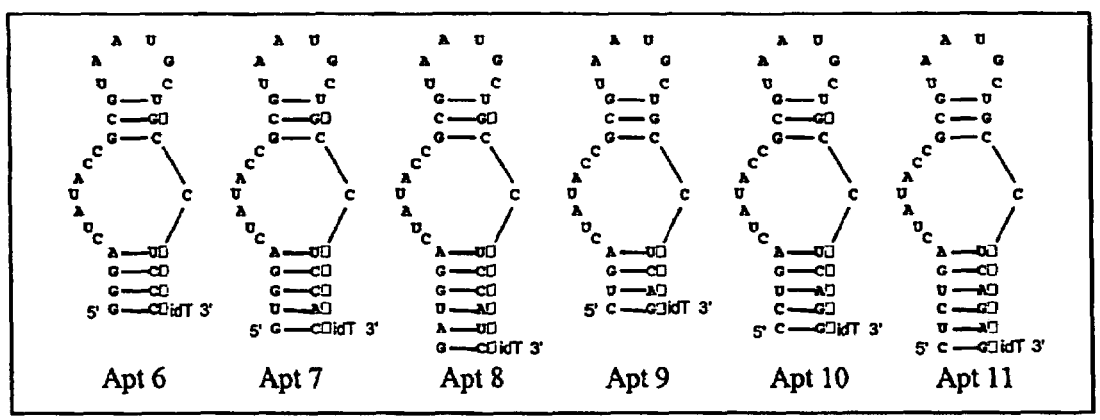
Figure 1:
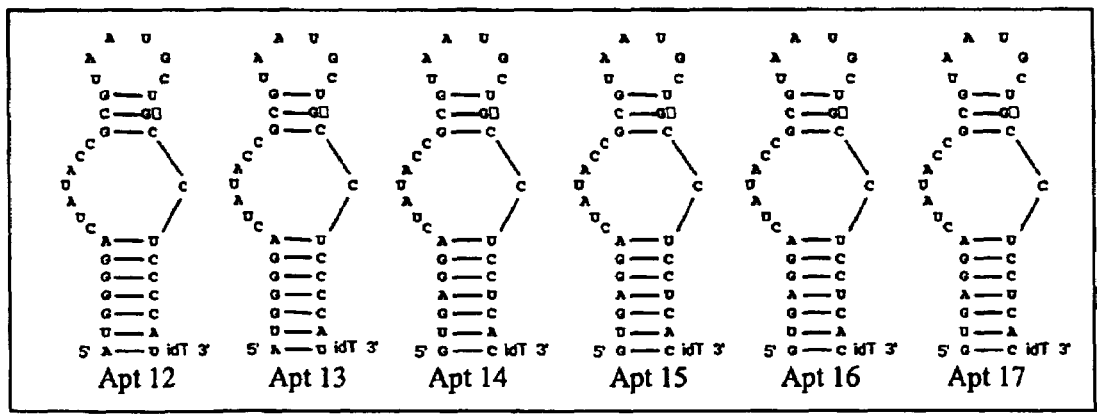
Figure 1:
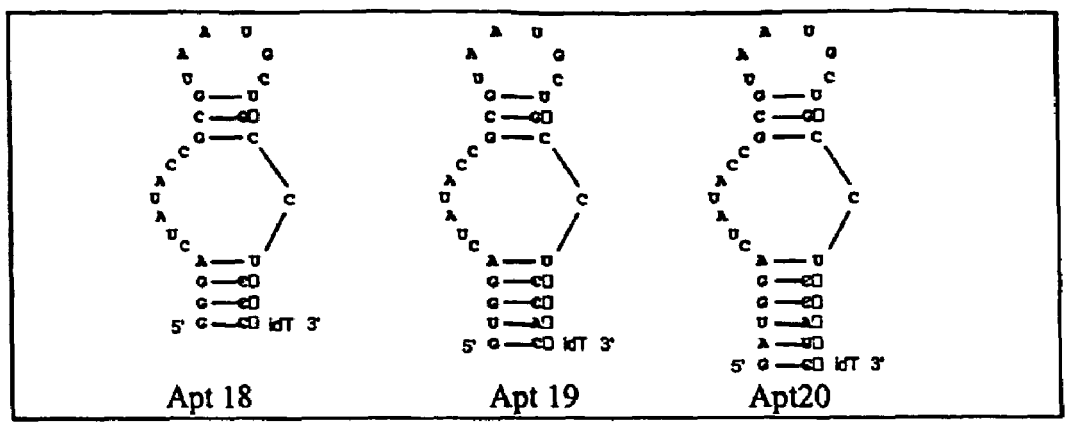
Figure 1:
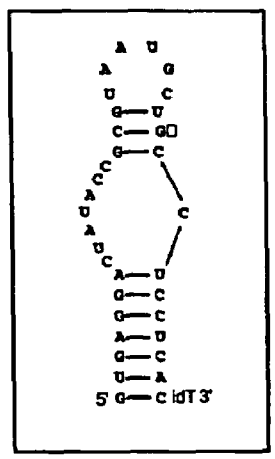
Figure 1:
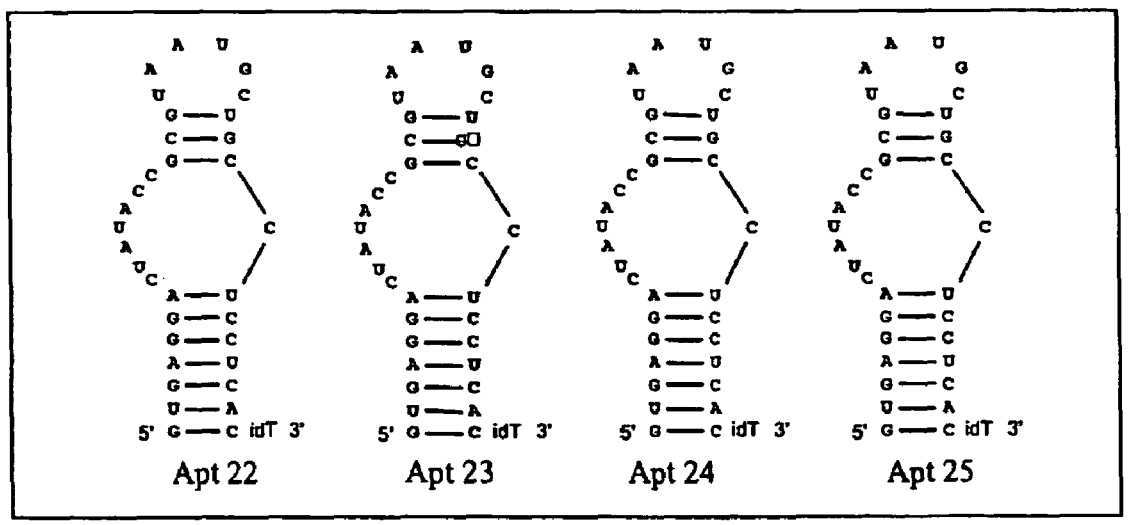
Figure 1:
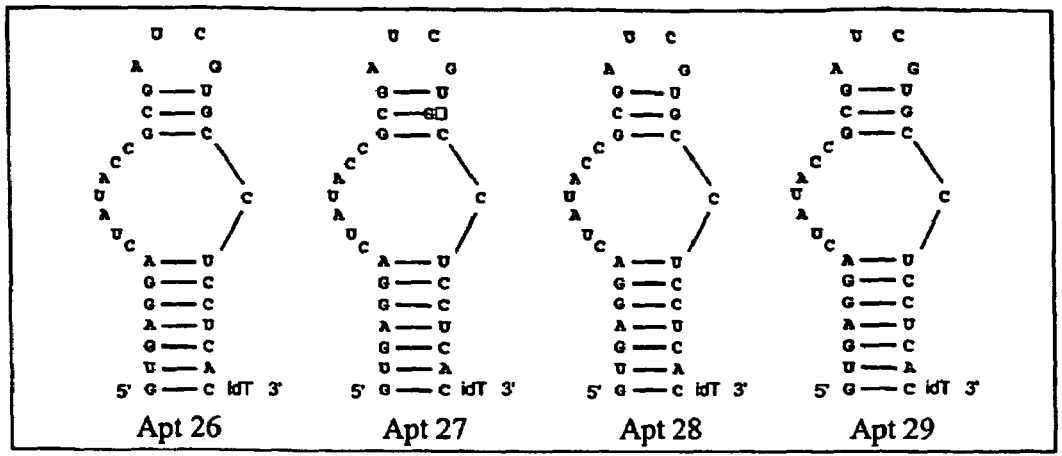
Figure 1:
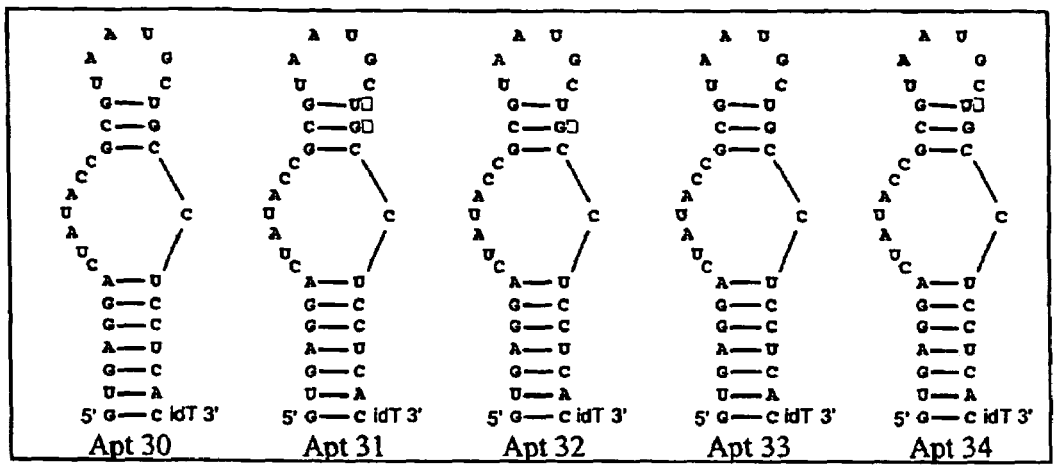
Figure 1:
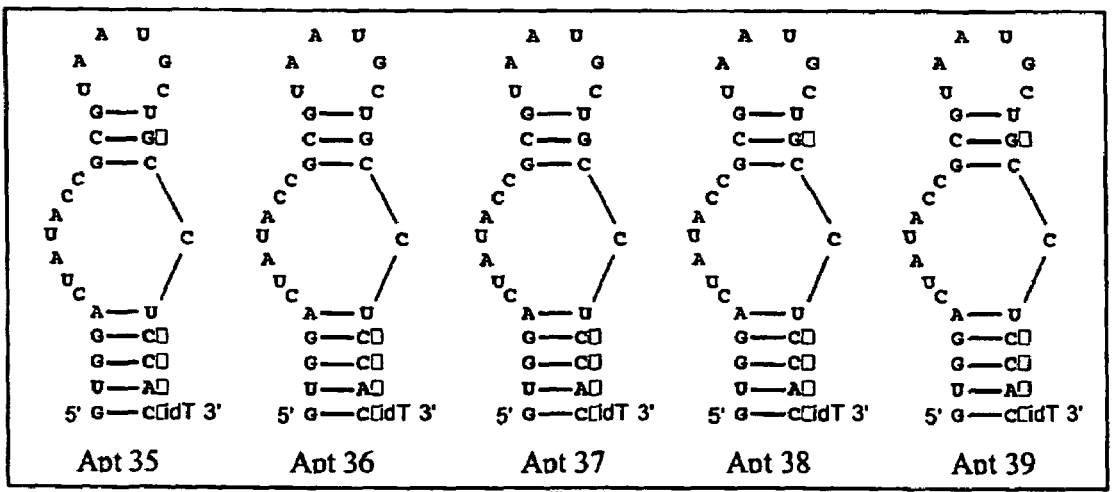

A "nucleic acid ligand" or "aptamer" is a nucleic acid that can form a three dimensional configuration, which allows it to interact as a ligand with a target molecule. The terms refer to oligonucleotides having specific binding regions that are capable of forming complexes with an intended target molecule in an environment wherein other substances in the same environment are not complexed to the oligonucleotide. The specificity of the binding is defined in terms of the comparative dissociation constants ($K_d$) of the aptamer for target as compared to the dissociation constant with respect to the aptamer and other materials in the environment or unrelated molecules in general. Typically, the $K_d$ for the aptamer with respect to the target will be 10-fold, 50-fold, 100-fold, or 200-fold less than the $K_d$ with respect to the unrelated material or accompanying material in the environment.

"Aptamer antidote pair" is meant to include a specified aptamer to a target molecule, and an oligonucleotide that changes the three dimensional configuration of the aptamer so that the aptamer can no longer interact with its target. The antidote can be an oligonucleotide complimentary to a portion of the aptamer. The antidote can change the conformation of the aptamer to reduce the target binding capacity of the aptamer by 10 to 100%, 20 to 100%, 25%, 40%, 50%, 60%, 70%, 80%, 90% or 100%, or any percentage in the range between 10 and 100% under physiological conditions. The antidote can also form a three dimensional structure with binding activity to a target molecule. This target can be the same or different from the target of the aptamer.

"Antidote," "Regulator" or "Modulator" refers to any pharmaceutically acceptable agent that can bind an aptamer and modify the interaction between that aptamer and modify the interaction between that aptamer and its target molecule (e.g., my modifying the structure of the aptamer) in a desired manner.

The terms "binding activity" and "binding affinity" are meant to refer to the tendency of a ligand molecule to bind or not to bind to a target. The energy of said interactions are significant in "binding activity" and "binding affinity" because they define the necessary concentrations of interacting partners, the rates at which these partners are capable of associating, and the relative concentrations of bound and free molecules in a solution. The specificity of the binding is defined in terms of the comparative dissociation constants ($K_d$) of an antidote of a nucleic acid ligand as compared to the dissociation constant with respect to other materials in the environment or unrelated molecules in general.

As used herein, "consensus sequence" refers to a nucleotide sequence or region (which might or might not be made up of contiguous nucleotides) that is found in one or more regions of at least two nucleic acid sequences. A consensus sequence can be as short as three nucleotides long. It also can be made up of one or more noncontiguous sequences, with nucleotide sequences or polymers of up to hundreds of bases long interspersed between the consensus sequences. Consensus sequences can be identified by sequence comparisons between individual nucleic acid species, which comparisons can be aided by computer programs and other, tools for modeling secondary and tertiary structure from sequence information. Generally, the consensus sequence will contain at least about 3 to 20 nucleotides, more commonly from 6 to 10 nucleotides.

The terms "cardiovascular disease" and "cardiovascular diseases" are meant to refer to any cardiovascular disease as would be understood by one of ordinary skill in the art. Nonlimiting examples of particularly contemplated cardiovascular diseases include, but are not limited to, atherosclerosis, thrombophilia, embolisms, cardiac infarction (e.g., myocardial infarction), thromboses, angina, stroke, septic shock, hypertension, hyper-cholesterolemia, restenosis and diabetes (and associated diabetic retinopathy). Cardiovascular disease can be treated at any stage of progression, such as treatment of early onset cardiovascular disease as well as treatment of advanced cardiovascular disease. A therapeutic method directed toward-inhibiting the aggravation of cardiovascular disease by modulating coagulation is also included in the invention.

2. Aptamers to Factor IX

The invention provides improved nucleic acid ligands or aptamers that regulate blood coagulation through interaction with specific factors in the blood coagulation cascade. The invention also provides improved aptamer-antidote pairs to regulate coagulation. The improved aptamers target Factor IX gene products (which include Factor IXa) and thus reduce the non-specific side effects associated with other blood coagulation factor targets. Most factors in the coagulation cascade are broad spectrum proteins with a variety of physiological roles (i.e. thrombin).

The events which occur between injury and blood clot formation are a carefully regulated and linked series of reactions. In a cell-based model of coagulation, initiation takes place on tissue factor-bearing cells (monocytes, macrophages, endothelial cells). In the presence of FVIIa (complexed with tissue factor), activation of FIX and FX generates a small amount of thrombin from prothrombin (which subsequently activates FV) In the amplification phase (also referred to as the priming phase), the small amount of thrombin generated activates platelets, causing release of FVa, FXIa and FVIIIa. During the final phase of coagulation, propagation, FIXa complexes with FVIIIa, activating FX. The FXa-FVa complex, in the presence of calcium and phospholipids substrate (prothrombinase complex), leads to a "burst" of thrombin generation.

The cell-based model of anticoagulation has been instrumental in defining coagulation protease targets. Most previous work has focused on blood coagulation through a variety of factors such as thrombin. Thrombin is a broad acting protein with effects throughout the body. Inhibitors of thrombin can therefore have unanticipated side effects in addition to the effects on coagulation. Thrombin not only activates endothelial cells and induces leukocyte infiltration and edema but also activates astrocytes and microglia to propagate the focal inflammation and produce potential neurotoxic effects.

The inventor has determined that Factor IXa in particular represents an attractive target because of its participation in both the initiation and propagation phases of coagulation. Interactive in vitro selection techniques have been used to identify oligonucleotides capable of binding FIXa with high affinity ($K_d$ 0.65±0.2 nM). Experimental studies suggest that FIXa may have a critical role in thrombosis, as well as hemostasis. Infusion of purified FIXa into rabbits induces thrombosis (Gitel et al. (1977) *PNAS* 74:3028-32; Gurewich et al. (1979) *Thromb. Rsch.* 14:931-940). In contrast, active site-blocked FIXa prevented clot formation and reduced intra-arterial coronary thrombosis (Lowe (2001) *Brit. J. Haem.* 115:507-513).

Antibodies to factor IX have also been shown to interfere with the function of the intrinsic tenase complex, the activation of zymogen factor IX by factor XIa and by the tissue factor:factor VIa complex and potently inhibit activated partial thromboplastin clotting times (APTT) in plasma of guinea pig and rat (Refino, C. J., et al, (1999) *Thromb and Haemost*, 82:1188-1195; Feuerstein G Z, et al. (1999) *Arterioscler Thromb Vasc Biol* 19(10):2554-62; Toomey J R, et al. (2000) *Thromb Res.* 100(1):73-9).

In one embodiment, the invention provides nucleic acid ligands or aptamers to a factor in the blood coagulation cascade. In some embodiments, the factors include Factor IX (FIX) or the cleavage product Factor IXa (FIXa). In some embodiments, the aptamers are ligands to the complex formed by FIXa with Factor VIIIa (FVIIIa), also known as the "intrinsic tenase complex." In some embodiments, the aptamers are ligands that inhibit the complex formation between FIXa and FVIIIa. In a subembodiment, the aptamers of the present invention bind to the complex of FIX and FVIIIa and inhibit activation of Factor X (FX). The aptamers can interact with FIX, FIXa or a complex formed with FVIIIa in the presence or absence of additional calcium. The aptamers can also interact with the factors of the complex at a cell membrane. In one embodiment, the aptamers bind to the intrinsic tenase complex at the membrane surface.

In one embodiment, the applicants have discovered improved aptamers to gene products of coagulation Factor IX (FIX), and to its cleavage product, Factor IXa (FIXa). In one embodiment, the nucleic acid ligand includes at least one region that binds to another region in the molecule via Watson-Crick base pairing (stem) and at least one region that does not bind to any other regions of the molecule under physiological conditions (loop). In a further embodiment, the nucleic acid ligand includes two stems (stem 1 and stem 2) and two loops (loop 1 and loop 2). In one embodiment, stem 1 is one to twenty nucleotides long. In a further embodiment, stem 1 is one to ten nucleotides long. In a further sub-embodiment, stem 1 is seven, six, five, four, three or two nucleotides long. In another embodiment, stem 2 one to twenty nucleotides long. In a further embodiment, stem 2 is one to ten nucleotides long. In a further sub-embodiment, stem 2 is seven, six, five, four, three or two nucleotides long.

The aptamers to a Factor IX gene product of the present invention can be comprised of ribonucleotides or deoxyribonucleotides, or a combination thereof. In general, the improved aptamers are at least 25 nucleotides long, and typically not longer than 35-40 nucleotides long. In one embodiment, aptamers are at least 25, 30, 35, or 40 nucleotides in length. In specific embodiments, the sequence of stem 1 includes 5 nucleotides in the 5'-3' direction. In a sub-embodiment, stem 1 includes three guanine (G) residues in the 5'-3' direction.

In an embodiment, the aptamers include the consensus nucleotide sequences gugg and the complimentary sequence ccac. When a number of individual, distinct aptamer sequences for a single target molecule have been obtained and sequenced, the sequences can be examined for "consensus sequences." As used herein, "consensus sequence" refers to a nucleotide sequence or region (which might or might not be made up of contiguous nucleotides) that is found in one or more regions of at least two aptamers, the presence of which can be correlated with aptamer-to-target-binding or with aptamer structure.

A consensus sequence can be as short as three nucleotides long. It also can be made up of one or more noncontiguous sequences. With nucleotide sequences or polymers of hundreds of bases long interspersed between the consensus sequences. Consensus sequences can be identified by sequence comparisons between individual aptamer species, which comparisons can be aided by computer programs and other, tools for modeling secondary and tertiary structure from sequence information. Generally, the consensus sequence will contain at least about 3 to 20 nucleotides, more commonly from 6 to 10 nucleotides. Not all oligonucleotides in a mixture can have the same nucleotide at such position; for example, the consensus sequence can contain a known ratio of particular nucleotides. For example, a consensus sequence might consist of a series of four positions wherein the first position in all members of the mixture is A, the second position is 25% A, 35% T and 40% C, the third position is T in all oligonucleotides, and the fourth position is G in 50% of the oligonucleotides and C in 50% of the oligonucleotides.

In specific embodiments, the aptamers include the nucleotide sequences of the following Seq ID Nos.:

| Seq ID Code | Size | Sequence |
|---|---|---|
| 9 AptA | 35mer | (5'-3') sequence: augggga cuauacc gcg uaaugc ugc c uccccau t |
| 10 Apt1 | 35mer | (5'-3') sequence: augggga cuauacc gcguaaugcugcc uccccau t |
| 9 Apt2 | 35mer | (5'-3') sequence: augggga cuauacc gcg uaaugc ugc c uccccau t |
| 9 Apt3 | 35mer | (5'-3') sequence: augggga cuauacc gcg uaaugc ugc c uccccau t |
| 9 Apt4 | 35mer | (5'-3') sequence: augggga cuauacc gcg uaaugc ugc c uccccau t |
| 9 Apt5 | 35mer | (5'-3') sequence: augggga cuauacc gcg uaaugc ugc c uccccau t |
| 11 Apt6 | 29mer | (5'-3') sequence: ggga cuauaccgcg uaaugcugcc uccc t |
| 12 Apt7 | 31mer | (5'-3') sequence: gugga cuauaccgc guaaugcugcc uccac t |
| 13 Apt8 | 33mer | (5'-3') sequence: gaugga cuauaccg cguaaugcugcc uccauc t |
| 14 Apt9 | 29mer | (5'-3') sequence: cuga cuauaccgcg uaaugcugcc ucag t |
| 15 Apt10 | 31mer | (5'-3') sequence: ccuga cuauaccgc guaaugcugcc ucagg t |
| 16 Apt11 | 33mer | (5'-3') sequence: cucuga cuauaccg cguaaugcugcc ucagag t |
| 10 Apt12 | 35mer | (5'-3') sequence: augggga cuauacc gcguaaugcugcc uccccau t |
| 10 Apt13 | 35mer | (5'-3') sequence: augggga cuauacc gcguaaugcugcc uccccau t |
| 17 Apt14 | 35mer | (5'-3') sequence: gugagga cuauacc gcguaaugcugcc uccucac t |
| 17 Apt15 | 35mer | (5'-3') sequence: gugagga cuauacc gcguaaugcugcc uccucac t |
| 17 Apt16 | 35mer | (5'-3') sequence: gugagga cuauacc gcguaaugcugcc uccucac t |
| 17 Apt17 | 35mer | (5'-3') sequence: gugagga cuauacc gcguaaugcugcc uccucac t |
| 11 Apt18 | 29mer | (5'-3') sequence: ggga cuauaccgcg uaaugcugcc uccc t |
| 12 Apt19 | 31mer | (5'-3') sequence: gugga cuauaccgc guaaugcugcc uccac t |
| 13 Apt20 | 33mer | (5'-3') sequence: gaugga cuauaccg cguaaugcugcc uccauc t |
| 18 Apt21 | 35mer | (5'-3') sequence: gugagga cuauacc gcg uaaugc ugc c uccucac t |

-continued

| Seq ID Code | Size | Sequence |
|---|---|---|
| 18 Apt22 | 35mer | (5'-3') sequence: gugagga cuauacc gcg uaaugc ugc c uccucac t |
| 18 Apt23 | 35mer | (5'-3') sequence: gugagga cuauacc gcg uaaugc ugc c uccucac t |
| 18 Apt24 | 35mer | (5'-3') sequence: gugagga cuauacc gcg uaaugc ugc c uccucac t |
| 18 Apt25 | 35mer | (5'-3') sequence: gugagga cuauacc gcg uaaugc ugc c uccucac t |
| 27 Apt26 | 33mer | (5'-3') sequence: gugagga cuauacc gca aucg ugc c uccucac t |
| 28 Apt27 | 33mer | (5'-3') sequence: gugagga cuauacc gca aucg ugc c uccucac t |
| 29 Apt28 | 33mer | (5'-3') sequence: gugagga cuauacc gca aucg ugc c uccucac t |
| 30 Apt29 | 33mer | (5'-3') sequence: gugagga cuauacc gca aucg ugc c uccucac t |
| 18 Apt30 | 35mer | (5'-3') sequence: gugagga cuauacc gcg uaaugc ugc c uccucac t |
| 18 Apt31 | 35mer | (5'-3') sequence: gugagga cuauacc gcg uaaugc ugc c uccucac t |
| 18 Apt32 | 35mer | (5'-3') sequence: gugagga cuauacc gcg uaaugc ugc c uccucac t |
| 18 Apt33 | 35mer | (5'-3') sequence: gugagga cuauacc gcg uaaugc ugc c uccucac t |
| 18 Apt34 | 35mer | (5'-3') sequence: gugagga cuauacc gcg uaaugc ugc c uccucac t |
| 19 Apt35 | 31mer | (5'-3') sequence: gugga cuauacc gcg uaaugc ugc c uccac t |
| 19 Apt36 | 31mer | (5'-3') sequence: gugga cuauacc gcg uaaugc ugc c uccac t |
| 19 Apt37 | 31mer | (5'-3') sequence: gugga cuauacc gcg uaaugc ugc c uccac t |
| 19 Apt38 | 31mer | (5'-3') sequence: gugga cuauacc gcg uaaugc ugc c uccac t |
| 19 Apt39 | 31mer | (5'-3') sequence: gugga cuauacc gcg uaaugc ugc c uccac t |

In one embodiment, the aptamer to Factor IX comprises, consists, or consists essentially of, the nucleotide sequence: gugga cuauacc gcg uaaugc ugc c uccac t (SeqID 19).

3. Modifications

The improved aptamers and aptamer-antidote combinations of the present invention are modified by substituting particular sugar residues, by changing the composition of the aptamer and the size of particular regions in the aptamer, and by designing aptamers that can be more effectively inhibited by antidotes. The design of aptamers includes an appreciation for the secondary structure of the aptamer (see FIG. 1) and the relationship between the secondary structure and the antidote control. Unlike conventional methods of modifying nucleic acids, the design of the improved aptamers to FIX gene products included in the invention must include a consideration of the antidote control. Controlled aptamers require that the aptamer be stable in circulation but not so stable that it is not antidote controlled. The aptamers can be modified by truncation, but antidotes need to be designed to control each aptamer when truncated. Further, certain modifications, particularly at the interface of the stems and loops cannot be modified from 2'-fluoro or the aptamer can lose activity.

In one embodiment, the design includes decreasing the 2'-hydroxyl content of the aptamer or the antidote, or both. In another embodiment, the design includes decreasing the fluoro content of the aptamer or the antidote, or both. In a further embodiment, the design includes increasing the O-methyl content of the aptamer or the antidote, or both. In a further embodiment, the design includes decreasing the size of the aptamer. In another embodiment, the size of the antidote is changed in relation to the size of the aptamer. In yet another embodiment, guanine strings are reduced to less than four guanine, or less than three guanine, or less than two guanine or no guanines. However, the joint effect of these changes must meet the challenge of creating an anticoagulant that provides adequate activity but is easily neutralized by the antidote.

Yet another embodiment includes a method of designing aptamers with a "suicide position" which allows more effective regulation by paired antidotes. In one embodiment, this position becomes single stranded and labile upon binding of the antidote to the improved aptamer and allows for cleavage of the improved aptamer upon binding of the antidote by enzymes in the circulation, such as blood or liver endonucleases, thereby effectively eliminating the active aptamer from circulation. The suicide position can be, in one embodiment, at a guanine in stem 2 that is hydroxylated. In one embodiment, the aptamer is in a double stranded configuration until bound with an antidote and becomes single stranded and available for cleavage upon binding of the antidote.

The applicants have discovered aptamer-antidote pairs that are stable and bioactive by including secondary modifications on either the aptamer or antidote or both. In specific embodiments, the aptamers to Factor IX include modified nucleotides. In one embodiment, the aptamer contains one or more 2'-O-methyl groups. In another embodiment, the aptamer and antidote contain one or more 2'-O-methyl and one or more 2'-fluoro modifications. In another embodiment, the aptamer and antidote contain no 2'-fluoro modifications. In yet another embodiment, the aptamer includes one or more 2'-O-methyl and one or more 2'-fluoro modifications on its stem. The aptamers can also include nucleotides that are modified with soluble polymers. Such polymers can include polyethylene glycol, polyamines, polyesters, polyanhydrides, polyethers or other water soluble pharmaceutically acceptable polymer.

Figure 2:
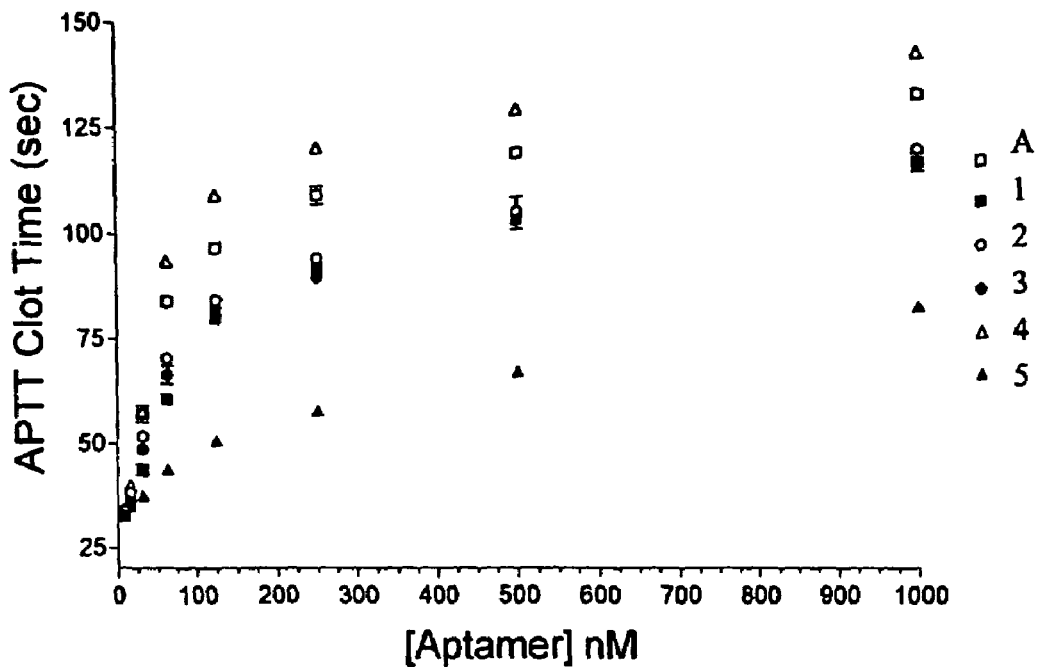
FIG. 2 is a graph of results of activated partial thromboplastin time (APTT) test assays of aptamers Apt A and Apt 1-5 (left panel) and neutralizability by antidote AptA-AD.
Figure 2:
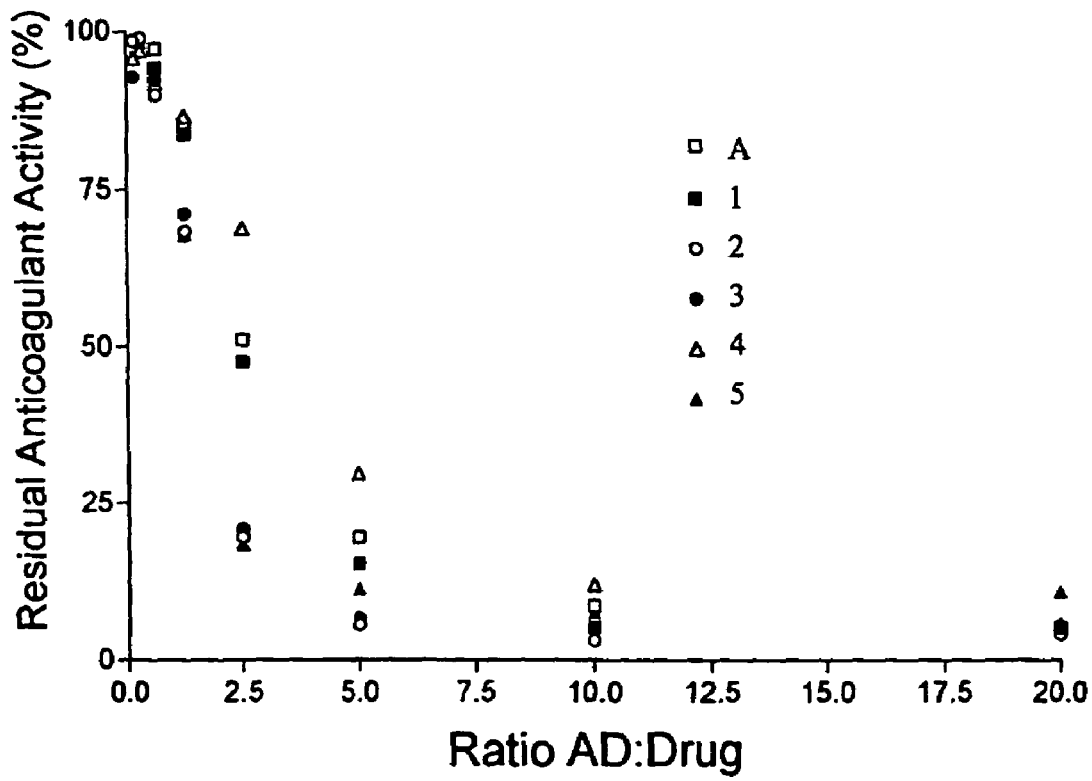

Purines within given aptamer sequence of FIX inhibitor can tolerate substitution of 2'-O-methyl sugars for current 2'hydroxyl sugars (Example 1, FIG. 1). Applicants found that the aptamers fall into three classes: (1) gain of anticoagulant activity (Apt4); (2) moderate loss of activity (Apt-1, 2, and 3); and (3) severe loss of activity (Apt 5) (FIG. 2). Data from Apt-5 indicates that the impact of wholly substituting 2'-O-methyl purines for 2'hydroxyl purines is significantly greater than any individual sector substitution alone (FIG. 2). In the case of this aptamer, it is possible that this suggests potential interaction between sectors, or that impairment caused by substitution within one of the sectors is exacerbated by additional modifications (i.e. one of the sectors is an Achilles heel). The enhanced antidote control exhibited by Apt-1, 2 and 3 suggests that introduction of 2'O-methyl residues within the antidote binding site improves the ability of the antidote oligonucleotide to bind to the aptamer. This is consistent with the increase in thermodynamic stability observed for duplexes containing 2'-O-methyl RNA residues in each strand, and suggests that duplexes of 2'-O-methyl-2'-O-methyl strands are more thermodynamically stable than duplexes composed of 2'O-methyl-2'fluoro strands. An alternative conclusion is that the reduction in activity of Apt-1, 2 and 3 leads to more "free" aptamer in the plasma at any given time, which is thus more readily bound by the antidote oligonucleotide In another embodiment, aptamers of the present invention can include modified pyrimidine nucleosides. Replacing 2'fluoropyrimidines with 2'-O-methyls within stem 1 improved activity and yielded a compound that tolerates a greater level of substitution. Comparison of the activity of Apt 30 and 33 to Apt 31 and 32 demonstrates that C 16 needs to contain a 2'fluoro sugar and G25 a 2'hydroxyl sugar (FIG. 16a). Activity observed between Apt 31 and 32 suggests that remaining positions within stem 2 can contain 2'-O-methyl sugars. In fact, Apt 31 appears to possess slightly greater potency than Apt 32, indicating that a compound with 2'fluoro at C16, 2'hydroxyl at G25, and the remaining residues 2'-O-methyl may exhibit greater potency than Apt 33. Apt 33 is more readily neutralizable than Apt 30, suggesting additional 2'-O-methyl residue within the antidote-binding site of the aptamer improves antidote binding. Apt 34 have C16 as a 2'fluoro rather than 2'-O-methyl nucleoside (FIG. 16b). Substitution increased anticoagulant activity (compare Apt 34 to Apt 33) but did result in a modest loss of "neutralizability", although 34 still requires a lower excess of antidote to achieve 90% neutralization (~5:1 vs 10:1) than the parental AptA compound (FIG. 16b). Both results are consistent with an increase in the stability of stem 2 due to 2'-O-methyl substitution. It is surprising that others have not obviously pursued 2'-O-methyl substitution of 2'-fluoropyrimidines, as such substitution reduces cost of synthesis and appears to enable increased aptamer modification due to increased stem stability.

In one embodiment, at least on guanine in stem 2 of an aptamer includes a hydroxyl sugar (2'-OH). In one embodiment, at least one uridine in stem 1 or stem 2 is a modified base. This can be either a 2'-fluoro (2'-F) or 2'-O-methyl (2'-OCH$_3$) modification. In one embodiment, at least one uridine in stem 1 or stem 2 is 2'-O-methyl modified. In one embodiment, at least one cytidine in stem 2 is modified. In one embodiment, at least on cytidine in stem 2 is 2'-Fluoro modified.

Figure 6:
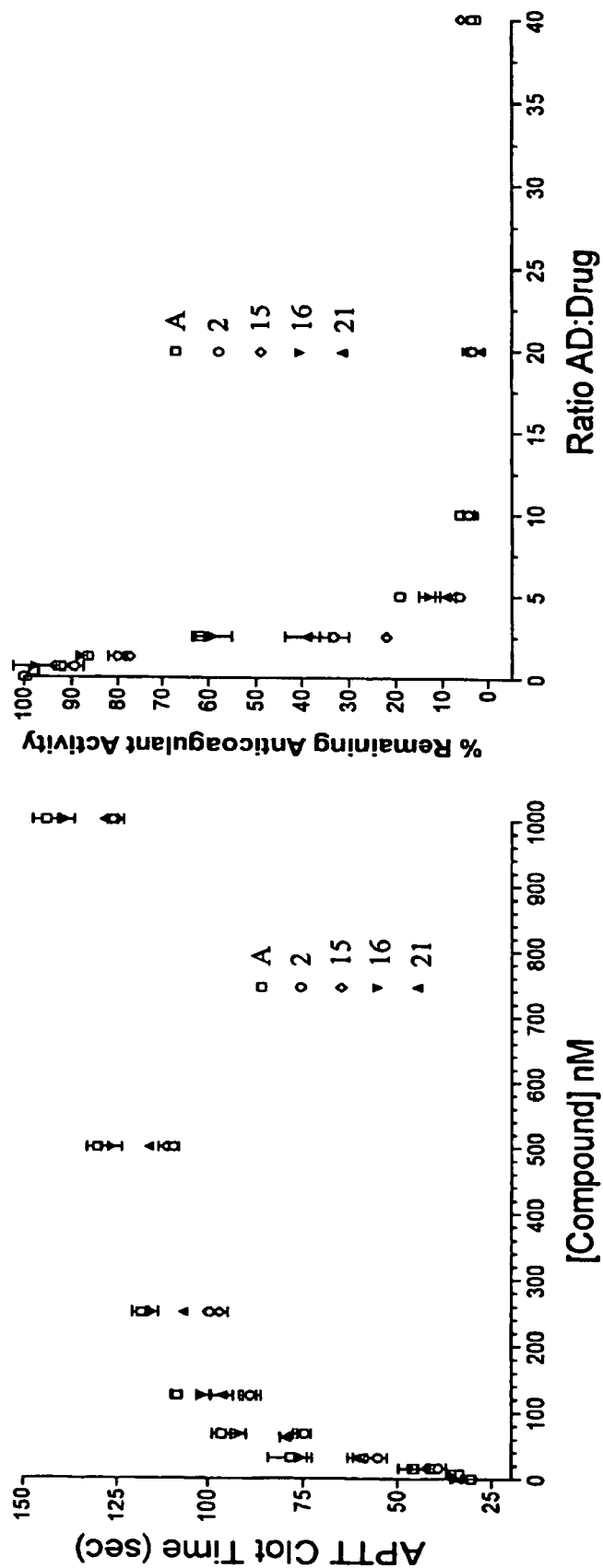
FIG. 6 is a graph of results of activated partial thromboplastin time (APTT) test assays of aptamers Apt 2, 15, 16 and 21 (left panel) and neutralizability by antidote (right panel).
Figure 7:
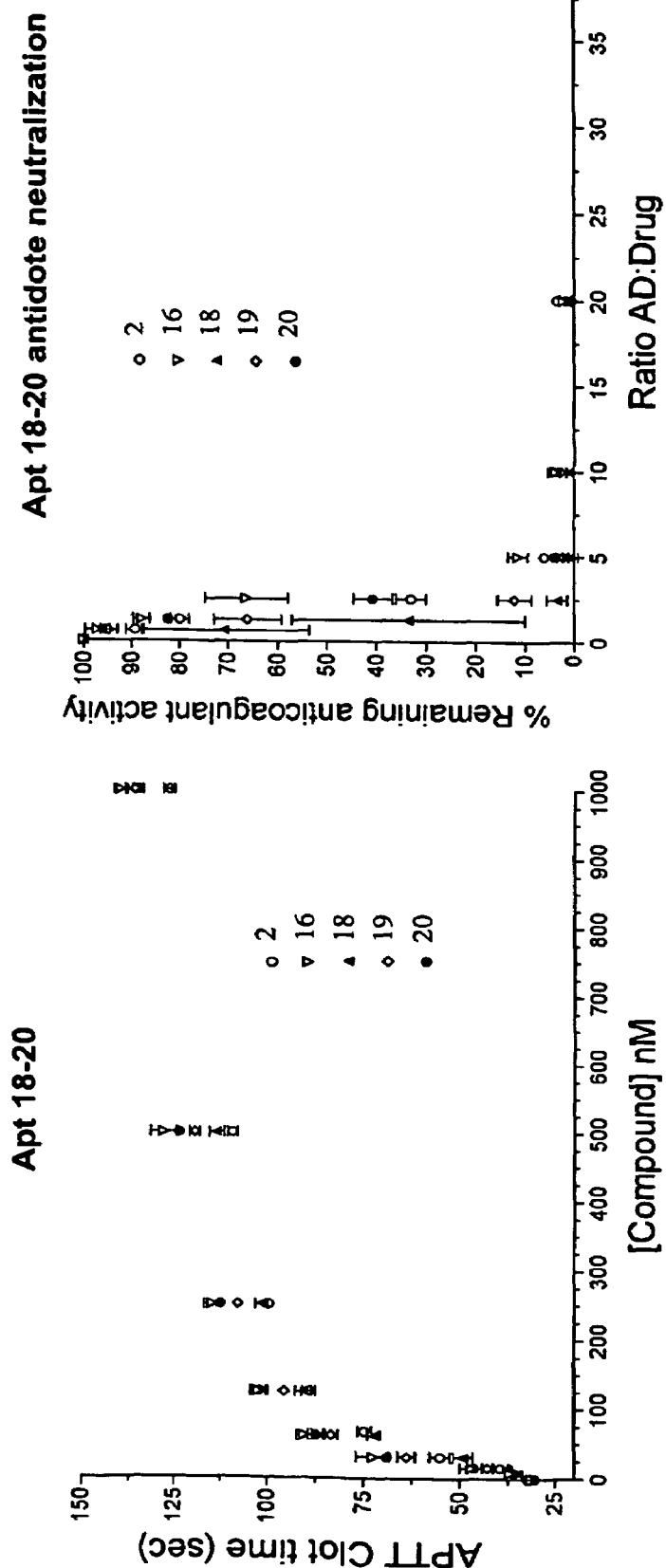
FIG. 7 is a graph of results of activated partial thromboplastin time (APTT) test assays of aptamers Apt 2 and 16-20 (left panel) and neutralizability by antidote (right panel).

However, comparison of the anticoagulant activity of Apt 12 with Apt 13 and 17 (FIG. 6) demonstrates that the loss of activity observed for Apt 6-11 is due to the presence of 2'-O-methyl substitutions at one or more critical residues (FIG. 7). Comparison of the anticoagulant activity of Apt 14 to Apt 12 indicates that the stretch of 4 consecutive guanosines within stem 1 can be altered without a significant impact on anticoagulant activity. Comparison of Apt 15 and 16 with Apt 2, 12 and 17 a) demonstrates that the presence of 2'-O-methyl sugars at each position within stem 1 except for the closing A-U pair at the top of stem 1 enhances activity; and b) demonstrates that the sugar of the U in this base pair must be 2'-fluoro for the aptamer to retain potency; and c) suggests that the sugar of the A in this base pair can be a 2'-O-methyl sugar without a significant impact on anticoagulant activity. In fact, Apt 16 retains essentially full potency.

Data suggests that the antidote can more readily bind the aptamer when stem 1 is a 2'-O-methyl-2'fluoro stem as opposed to when both strands of the duplex contain largely 2'-O-methyl residues. This is again consistent with the notion that duplexes composed of 2'-O-methyl residues in both strands are more stable than those composed of a largely 2'-O-methyl strand and a largely 2'fluoro strand. The enhanced anticoagulant activity of Apt 16 vs. Apt 15 is also consistent with this. Alternatively, the difference in neutralizability between 14, 15 and 16 could be due to the enhanced potency of Apt 16 compared to these two compounds. Regardless, all are neutralized at least as well as AptA. Based upon the observation that the anticoagulant activity of Apt 14 and 15 were similar, the sugar of the A at the stop of stem 1 was 2'-O-methyl substituted (Apt 21, FIG. 8).

Figure 9:
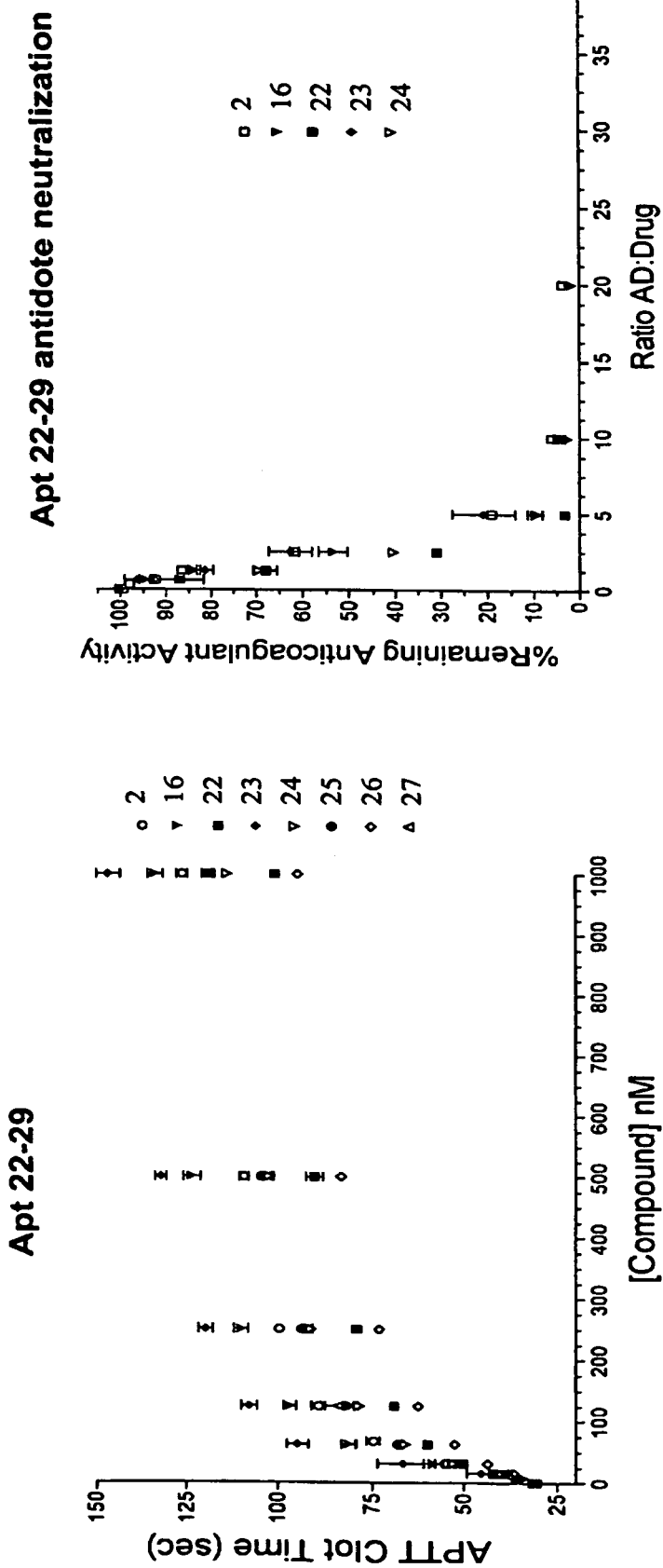
FIG. 9 is a graph of results of activated partial thromboplastin time (APTT) test assays of aptamers Apt 2, 16 and 22-27 (left panel) and neutralizability by antidote (right panel).

Substitution of a 2'-O-methyl sugar at this adenosine residue is well tolerated in the background of a largely 2'-O-methyl stem (FIG. 9). In fact, the potency of Apt 21 is intermediate between Apt 16 and 15. Antidote neutralization of Apt 21 is enhanced as compared to Apt 16 (see especially the 2.5:1 and 5:1 AD:Drug data points in FIG. 9).

Sugar modifications may ensure stability but they do not guarantee adequate pharmacokinetics for aptamers to be therapeutically active. In healthy individuals, aptamers are cleared from plasma within minutes of IV injection, probably through renal excretion. Keeping intact aptamers in the blood from hours to days after injection has been accomplished by conjugating them to larger macromolecules such as polyethyleneglycol (PEG). In another embodiment, aptamer plasma clearance has also been decreased by embedding them in liposomes.

Figure 3:
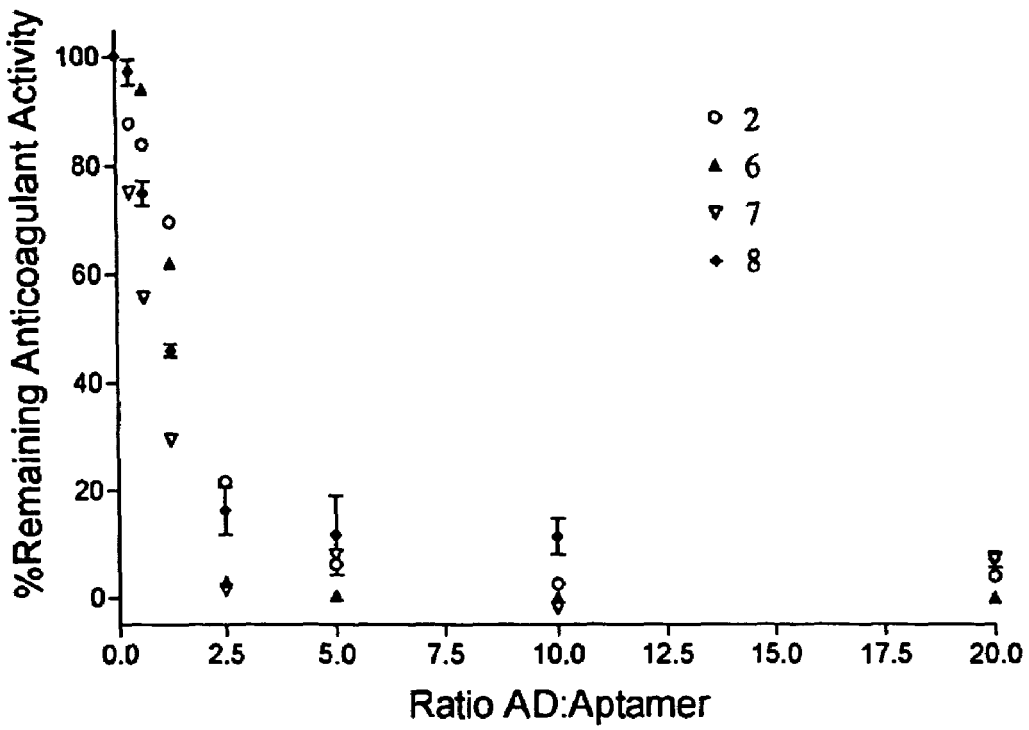
FIG. 3 is a graph of results of activated partial thromboplastin time (APTT) test assays of aptamers Apt 2 and 6-8 (right panel) and neutralizability by antidote (left panel).
Figure 3:
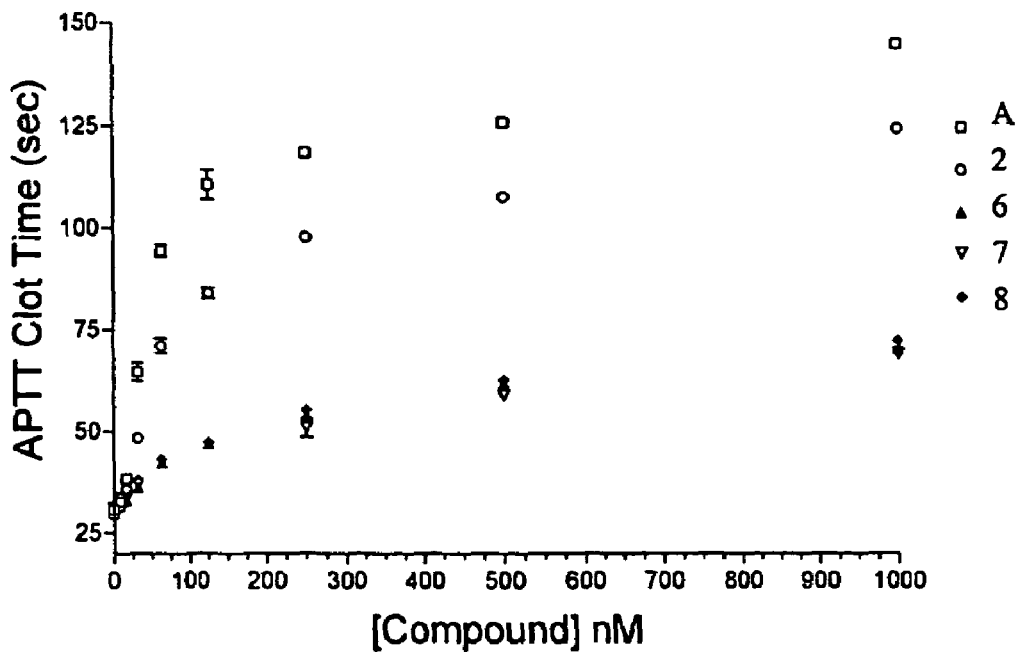
Figure 4:
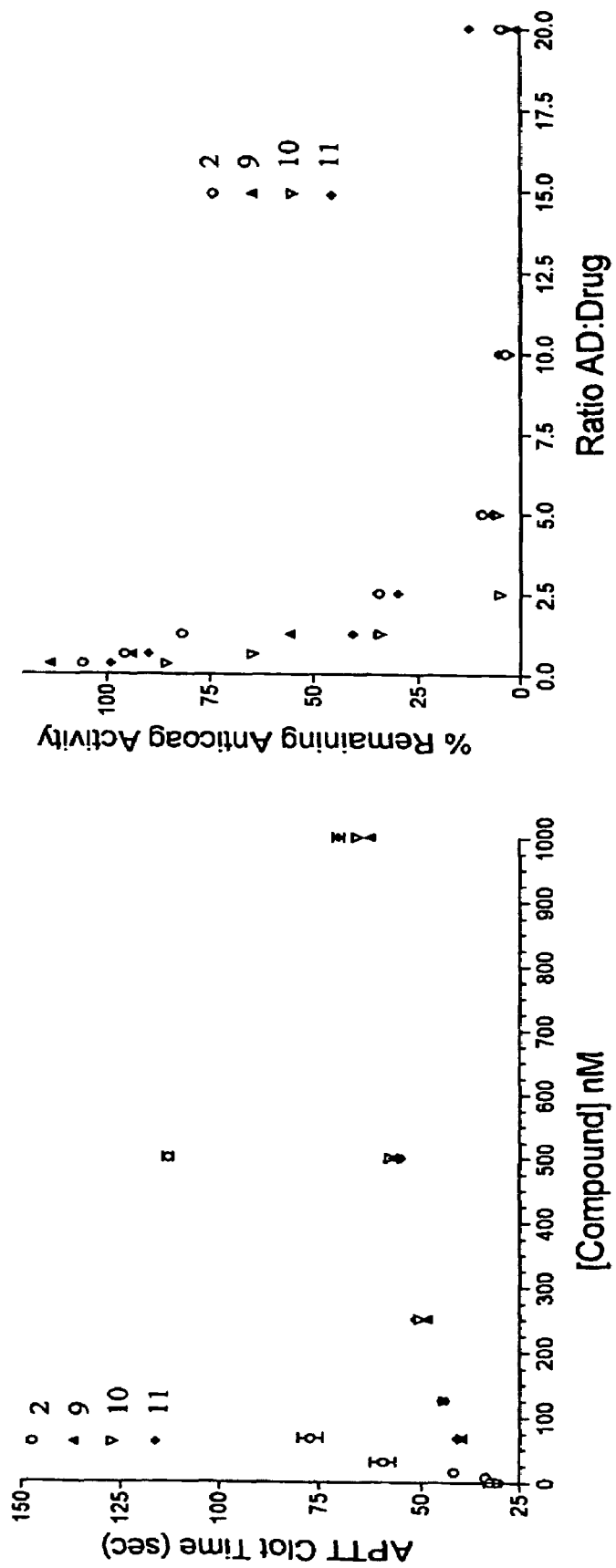
FIG. 4 is a graph of results of activated partial thromboplastin time (APTT) test assays of aptamers Apt 2 and 9-11 (left panel) and neutralizability by antidote (right panel).
Figure 5:
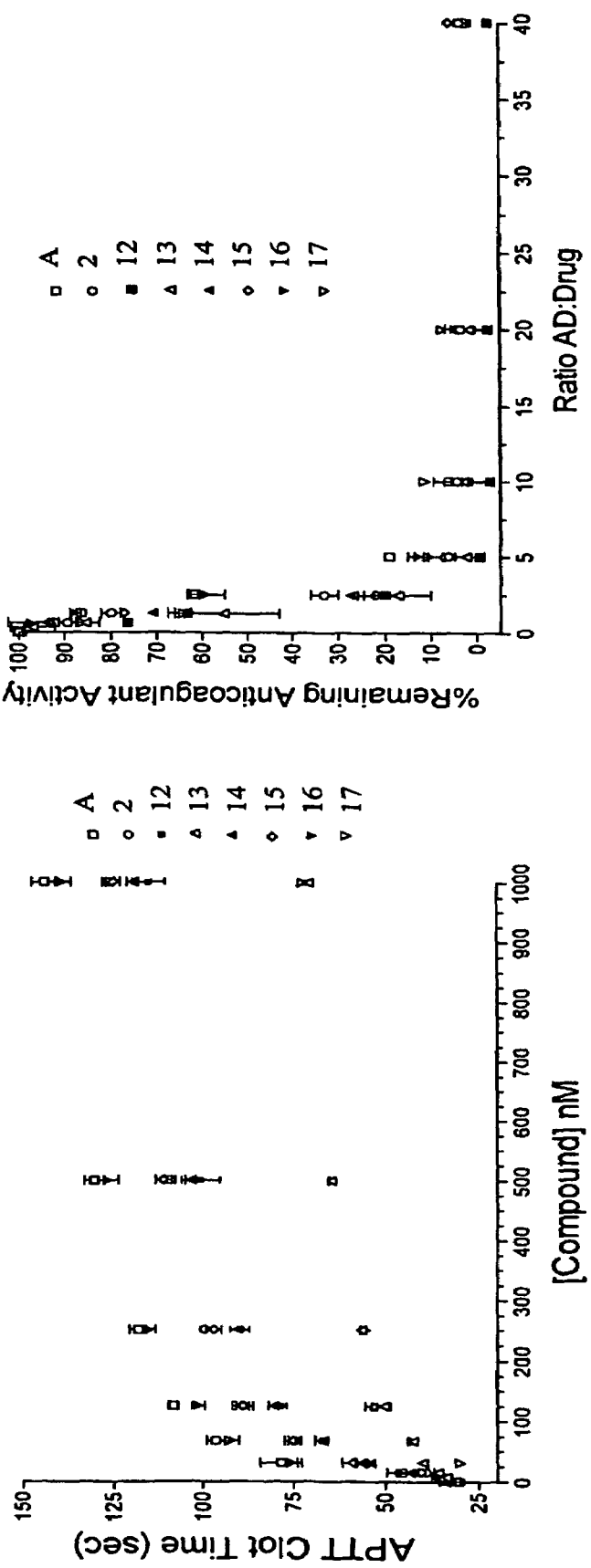
FIG. 5 is a graph of results of activated partial thromboplastin time (APTT) test assays of aptamers Apt A, 2 and 12-17 (left panel) and neutralizability by antidote (right panel).

Nucleic acid aptamers of the present invention can also be modified by varying the stem and loop sizes. Two families of aptamers with four, five, or six 2-O-methyl modified base pair stem 1 regions showed varying levels of anticoagulant activity and antidote control (see Example 2, FIGS. 3-5). Stem 1 mutants (FIG. 3) exhibit a loss of anticoagulant activity as measured in the APTT assay (FIGS. 4 and 5). All stem 1 variants exhibit less activity than the fully 2'-O-methyl purine/2'fluoro pyrimidine compound Apt 5, suggesting that one of the pyrimidines within stem 1 must contain a 2'fluoro sugar for the compound to retain potency. However, all exhibit similar activity levels suggesting stem length may not cause loss of activity. However, 5 base pair stem 1 constructs (Apt 10 and 7) do appear to be more readily antidote controlled than six base pair. Data suggests that a stem 1 of 5 base pairs may be preferable to those composed of 4, 6 or 7 base pairs to enhance antidote neutralization.

For targeting of an antidote, an improved aptamer can also be modified so as to include a single-stranded tail (3' or 5') in order to promote association with an oligonucleotide antidote. Suitable tails can comprise 1 to 20 nucleotides, preferably, 1-10 nucleotides, more preferably, 1-5 nucleotides and, most preferably, 3-5 nucleotides (e.g., modified nucleotides such as 2'-O-methyl sequences). Tailed aptamers can be tested in binding and bioassays (e.g., as described below) to verify that addition of the single-stranded tail does not disrupt the active structure of the aptamer. A series of oligonucleotides (for example, 2'-O-methyl oligonucleotides) that can form, for example, 1, 3 or 5 basepairs with the tail sequence can be designed and tested for their ability to associate with the tailed aptamer alone, as well as their ability to increase the rate of dissociation of the aptamer from, or association of the aptamer with, its target molecule. Scrambled sequence controls can be employed to verify that the effects are due to duplex formation and not non-specific effects.

In specific embodiments, the aptamers include the nucleotide sequences of any of the following sequences. ("A" is 2'OH A; "a" is 2'-O-methyl A; "G" is 2'-OH G; "g" is 2'-O-methyl G; "C" is 2'-Fluoro C; "c" is 2'-O-methyl C; "U" is 2'Fluoro U; "u" is 2'-O-methyl U; and "T" is inverted 2'H T.)

| Seq ID | Code | Sequence |
|---|---|---|
| 20 | AptA | AUGGGGA CUAUACC GCG UAAUGC UGC C UCCCCAU T |
| 21 | Apt1 | aUgggga CUAUACCGCGUAAUGCUGCC UCCCCaU T |
| 22 | Apt2 | AUGGGGA CUaUaCC GCG UAAUGC UGC C UCCCCAU T |
| 23 | Apt3 | AUGGGGA CUAUACC gCg UAAUGC UgC C UCCCCAU T |
| 24 | Apt4 | AUGGGGA CUAUACC GCG UaaUgC UGC C UCCCCAU T |
| 25 | Apt5 | aUgggga CUaUaCC gCg UaaUgC UgC C UCCCCaU T |
| 26 | Apt6 | ggga CUaUaCCGCGUAAUGCUGCC uccc T |
| 27 | Apt7 | gugga CUaUaCCGCGUAAUGCUGCC uccac T |
| 28 | Apt8 | gaugga CUaUaCCGCGUAAUGCUGCC uccauc T |
| 29 | Apt9 | cuga CUaUaCCGCGUAAUGCUGCC ucag T |
| 30 | Apt10 | ccuga CUaUaCCGCGUAAUGCUGCC ucagg T |
| 31 | Apt11 | cucuga CUaUaCCGCGUAAUGCUGCC ucagag T |
| 32 | Apt12 | aUgggga CUaUaCCGCGUAAUGCUGCC UCCCCaU T |
| 33 | Apt13 | augggga CUaUaCCGCGUAAUGCUGCC ucccau T |
| 34 | Apt14 | gUgagga CUaUaCCGCGUAAUGCUGCC UCCUCaC T |
| 35 | Apt15 | gUgaggA CUaUaCCGCGUAAUGCUGCC UCCUCaC T |
| 36 | Apt16 | gugaggA CUaUaCCGCGUAAUGCUGCC Uccucac T |
| 37 | Apt17 | gugagga CUaUaCCGCGUAAUGCUGCC uccucac T |
| 38 | Apt18 | gggA CUaUaCCGCGUAAUGCUGCC Uccc T |
| 39 | Apt19 | guggA CUaUaCCGCGUAAUGCUGCC Uccac T |
| 40 | Apt20 | gauggA CUaUaCCGCGUAAUGCUGCC Uccauc T |
| 41 | Apt21 | gugagga CUaUaCC GCG UAAUGC UGC C Uccucac T |
| 42 | Apt22 | gugaggA CUaUaCC gCg UAAUGC UGC C Uccucac T |
| 43 | Apt23 | gugagga CUaUaCC GCG UaaUgC UGC C Uccucac T |
| 44 | Apt24 | gugagga CUaUaCC gCg UaaUgC UgC C Uccucac T |
| 45 | Apt25 | gugaggA CUaUaCC GCg UaaUgC UgC C Uccucac T |
| 46 | Apt26 | gugaggA CUaUaCC gCa AUCG UgC C Uccucac T |
| 47 | Apt27 | gugaggA CUaUaCC GCA aUCg UGC C Uccucac T |
| 48 | Apt28 | gugaggA CUaUaCC gCa aUCg UgC C Uccucac T |
| 49 | Apt29 | gugaggA CUaUaCC GCa aUCg UgC C Uccucac T |
| 50 | Apt30 | gugagga CUaUaCC gCG UaaUgC UGC C Uccucac T |
| 51 | Apt31 | gugagga CUaUaCC gcg UaaUgC ugc C Uccucac T |
| 52 | Apt32 | gugagga CUaUaCC gcg UaaUgC UgC C Uccucac T |
| 53 | Apt33 | gugagga CUaUaCC gCg UaaUgC UGC C Uccucac T |
| 54 | Apt34 | gugagga CUaUaCC gCg UaaUgC uGc C Uccucac T |
| 55 | Apt35 | gugga CUaUaCC gCG UaaUgC UGC C Uccac T |
| 56 | Apt36 | gugga CUaUaCC gCG UaaUgC ugc C Uccac T |
| 57 | Apt37 | gugga CUaUaCC gCG UaaUgC UgC C Uccac T |
| 58 | Apt38 | gugga CUaUaCC gCg UaaUgC UGC C Uccac T |
| 59 | Apt39 | gugga CUaUaCC gCg UaaUgC uGc C Uccac T |

In one specific embodiment, the aptamer to Factor IXa comprises, consists, or consists essentially of, the nucleotide sequence: gugga CUaUaCC gCg UaaUgC uGc C Uccac T (Apt39; SEQ ID NO: 59).

In one embodiment, the aptamer is linked to one or more polyethylene glycol (PEG) molecules. In a specific embodiment, the aptamer is linked to 40 KD PEG using a six carbon amino linker. In one embodiment, one or more phosphate groups are included between the linker and the nucleic acid sequence. In a more specific embodiment, the six carbon amino linker is attached to the PEG through an amino acid attachment. In a subembodiment, the PEG is two twenty KD PEG that are attached to one or more amino acid, such as lysine, which is attached to the six carbon amino linker.

In one specific embodiment, the aptamer to Factor IXa is the following structure: 5'-O-[6-[$N^2$-(monomethoxy 20K polyethylene glycol carbamoyl)-$N^6$-(monomethoxy 20K polyethylene glycol carbamoyl)]-lysylamido]hexyl]-2'-methoxy-2'-deoxguanylyl-(3'-5')-2'-methoxy-2'-deoxyuridylyl-(3'-5')-2'-methoxy-2'-deoxyguanylyl-(3'-5')-2'-methoxy-2'-deoxyguanylyl-(3'-5')-2'-methoxy-2'-deoxyadenylyl-(3'-5')-2'-fluoro-2'-deoxycytidylyl-(3'-5')-2'-fluoro-2'-deoxyuridylyl-(3'-5')-2'-methoxy-2'-deoxyadenylyl-(3'-5')-2'-fluoro-2'-deoxyuridylyl-(3'-5')-2'-methoxy-2'-deoxyadenylyl-(3'-5')-2'-fluoro-2'-deoxycytidylyl-(3'-5')-2'-fluoro-2'-deoxycytidylyl-(3'-5')-2'-methoxy-2'-deoxyguanylyl-(3'-5')-2'-fluoro-2'-deoxycytidylyl-(3'-5')-2'-methoxy-2'-deoxyguanylyl-(3'-5')-2'-fluoro-2'-deoxyuridylyl-(3'-5')-2'-methoxy-2'-deoxyadenylyl-(3'-5')-2'-methoxy-2'-deoxyadenylyl-(3'-5')-2'-fluoro-2'-deoxyuridylyl-(3'-5')-2'-methoxy-2'-deoxyguanylyl-(3'-5')-2'-fluoro-2'-deoxycytidylyl-(3'-5')-2'-methoxy-2'-deoxyuridylyl-(3'-5')-riboguanylyl-(3'-5')-2'-methoxy-2'-deoxycytidylyl-(3'-5')-2'-fluoro-2'-deoxycytidylyl-(3'-5')-2'-fluoro-2'-deoxyuridylyl-(3'-5')-2'-methoxy-2'-deoxcytidylyl-(3'-5')-2'-methoxy-2'-deoxytidylyl-(3'-5')-2'-methoxy-2'-deoxyadenylyl-(3'-5')-2'-methoxy-2'-deoxycytidylyl-(3'-3')-thymidine.

In another embodiment, the aptamer to Factor IXa is of the following structure:

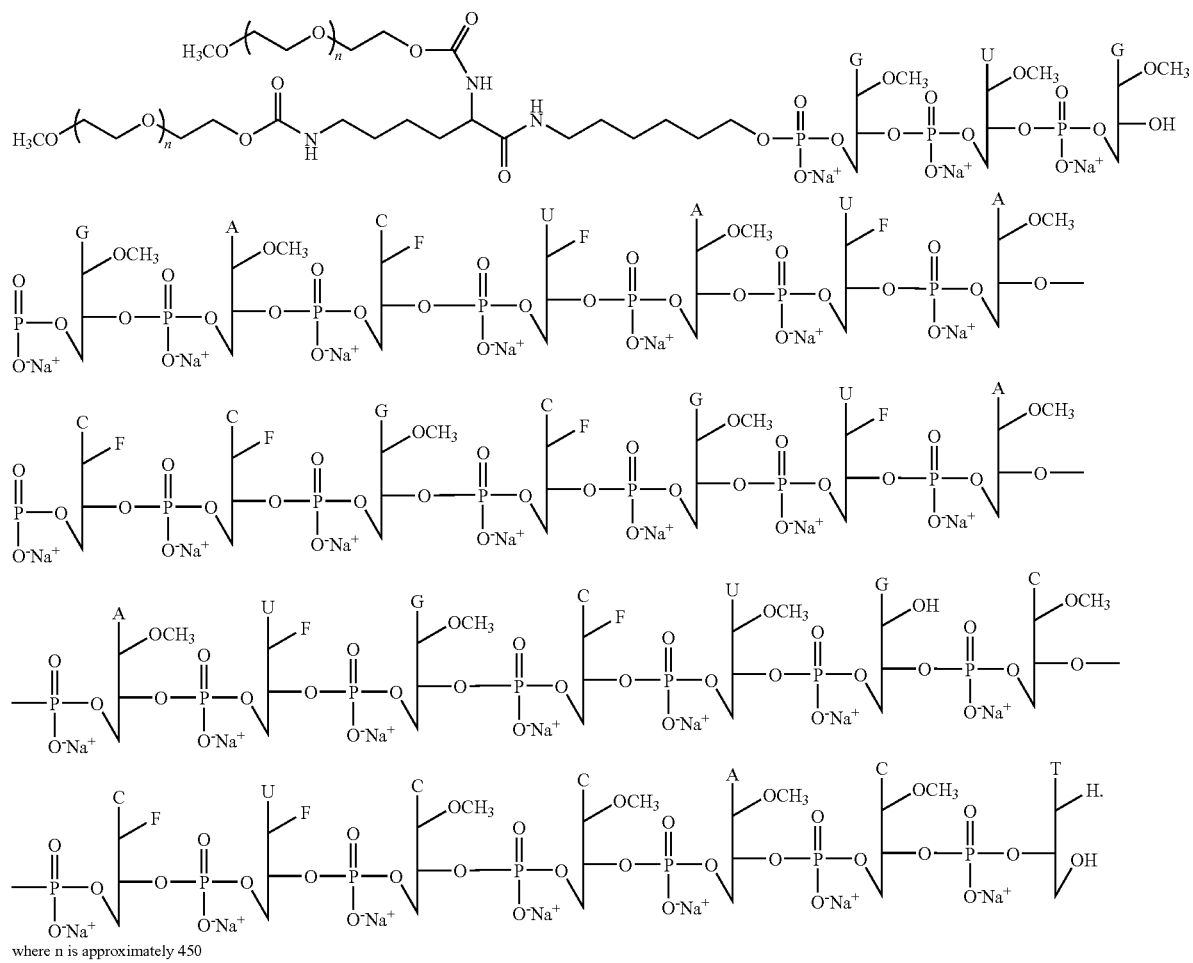

where n is approximately 450

In one embodiment, the molecular weight of the aptamer to Factor IXa is 10,282.4 Daltons in its protonated form. In another embodiment, the aptamer is in its sodium salt form. In yet another embodiment, the aptamer is PEGylated Apt39 and in its sodium salt.

The oligonucleotide antidotes can be administered directly (e.g., alone or in a liposomal formulation or complexed to a carrier, e.g. PEG)) (see for example, U.S. Pat. No. 6,147,204, U.S. Pat. No. 6,011,020). Surprisingly, the addition of a PEG molecule does not reduce aptamer binding to Factor IXa. A shorted stem 1 with pegylation do appears to increase neutralizability, providing a potentially more effective therapeutic. FIG. 10 shows the activity and neutralizability of a pegylated aptamer with a 5 base pair stem (Apt 19). Apt 19 possesses anticoagulant activity very similar to pegylated Apt16 with a 7 base pair stem 1, but ~90% of its activity can be neutralized with only a 2.5:1 excess of antidote to drug.

Therefore, in one embodiment, the improved aptamer or antidotes can be attached to a non-immunogenic, high molecular weight compound such as polyethylene glycol (PEG) or other water soluble pharmaceutically acceptable polymer as described herein. In one embodiment, the aptamer or antidote is associated with the PEG molecule through covalent bonds. Where covalent attachment is employed, PEG may be covalently bound to a variety of positions on the improved aptamer or antidote. In another embodiment, an oligonucleotide aptamer or antidote is bonded to the 5'-thiol through a maleimide or vinyl sulfone functionality. In one embodiment, a plurality of improved aptamers or antidotes can be associated with a single PEG molecule. The improved aptamers and antidotes can be the same or different sequences and modifications. In yet a further embodiment, a plurality of PEG molecules can be attached to each other. In this embodiment, one or more aptamers or antidotes to the same target or different targets can be associated with each PEG molecule. In embodiments where multiple aptamers or antidotes specific for the same target are attached to PEG, there is the possibility of bringing the same targets in close proximity to each other in order to generate specific interactions between the same targets. Where multiple aptamers or antidotes specific for different targets are attached to PEG, there is the possibility of bringing the distinct targets in close proximity to each other in order to generate specific interactions between the targets. In addition, in embodiments where there are aptamers or antidotes to the same target or different targets associated with PEG, a drug can also be associated with PEG. Thus the complex would provide targeted delivery of the drug, with PEG serving as a Linker.

Linkers can be selected from, for example, 6-(trifluoroacetamido)hexanol (2-cyanoethyl-N,N-diisopropyl)phosphoramidite of the structure:

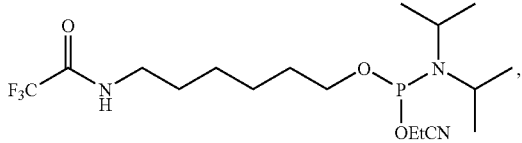

TFA-amino C4 CED phosphoramidite (available from ChemGenes, cat# CLP-1453) of the structure:

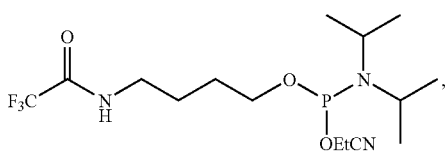

5'-amino modifier C3 TFA (available from Glen Research cat# 10-1923-90) of the structure:

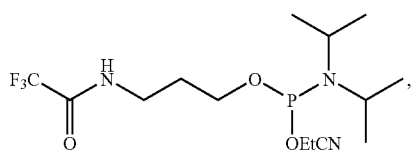

5'-Amino-Modifier C3-TFA

5'-amino modifier 5 (available from Glen Research cat# 10-1905-90) of the structure:

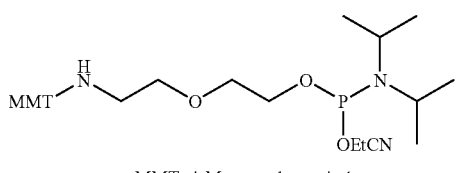

MMT: 4-Monomethoxytrityl
5'-Amino Modifier 5,

5'-amino modifier C12 (available from Glen Research cat# 10-1912-90) of the structure:

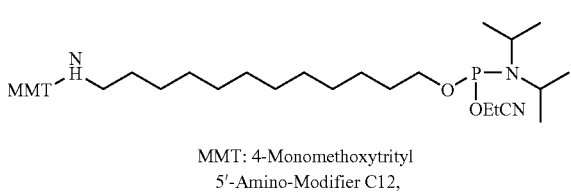

MMT: 4-Monomethoxytrityl
5'-Amino-Modifier C12,

5'thiol-modifier C6 (available from Glen Research cat# 10-1926-90) of the structure:

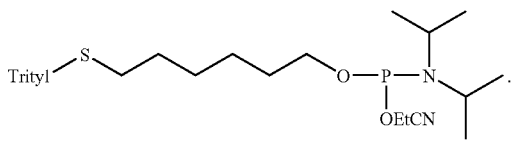

The 5'-thiol modified linker is used with PEG-maleimides, PEG-vinylsulfone, PEG-iodoacetamide and PEG-orthopyridyl-disulfide, for example.

Polyethylene glycols (PEGs) can be conjugated to biologically active compounds to serve as "inert" carriers to potentially (1) prolong the half-life of the compound in the circulation, (2) alter the pattern of distribution of the compound and/or (3) camouflage the compound, thereby reducing its immunogenic potential and protecting it from enzymatic degradation. PEGs can range in size from 5 to 200 KD, with typical PEGs used in pharmaceutical formulations in the 10-60 KD range. Linear chain PEGs of up to about 30 KD can be produced. For PEGs of greater than 30 KD, multiple PEGs can be attached together (multi-arm or 'branched' PEGs) to produce PEGs of the desired size. The general synthesis of compounds with a branched, "mPEG2" attachment (two mPEGs linked via an amino acid) is described in Monfardini, et al. (1995) *Bioconjugate Chem.* 6:62-69. For 'branched' PEGs, i.e. compounds that include more than one PEG or mPEG linked to a common reactive group, the PEGs or mPEGS can be linked together through an amino acid such as a lysine or they can be linked via, for example, a glycerine. For branched PEGs in which each mPEG is about 10, about 20, or about 30 KD, the total mass is about 20, about 40 or about 60 KD and the compound is referred to by its total mass (i.e. 40 kD mPEG2 is two linked 20 kD mPEGs). 40 KD total molecular weight PEGs, that can be used as reagents in producing a PEGylated compound, include, for example, [$N^2$-(monomethoxy 20K polyethylene glycol carbamoyl)-$N^6$-(monomethoxy 20K polyethylene glycol carbamoyl)]-lysine N-hydroxysuccinimide of the structures:

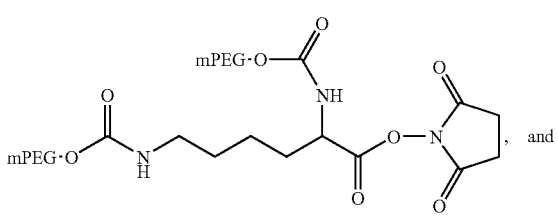

and

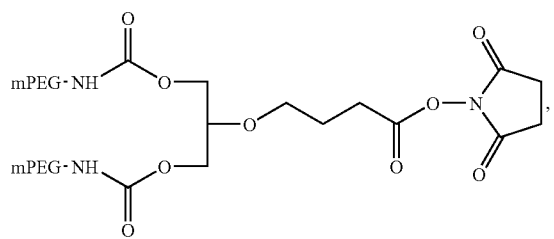

(mPEG is a 20 KD monomethoxy PEG). The general synthesis of compounds with a branched, "mPEG2" attachment is described in Monfardini, et al. (1995) *Bioconjugate Chem.* 6:62-69. For 'branched' PEGs, i.e. compounds that include more than one PEG or mPEG linked to a common reactive group, the PEGs or mPEGS can be linked together through an amino acid such as a lysine.

Additional PEG reagents that can be used to prepare stabilized compounds of the invention include other branched PEG N-Hydroxysuccinimide (mPEG-NHS) of the general formula:

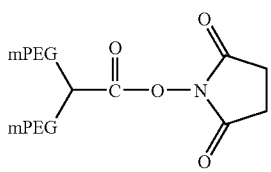

with a 40 KD or 60 KD total molecular weight (where each mPEG is about 20 or about 30 KD). Compounds of this structure are sold, for example, by Nektar Therapeutics as cat# 2Z3Y0L01 and cat# 2Z3Y0V01. As described above, the branched PEGs can be linked through any appropriate reagent, such as an amino acid, and in certain embodiments are linked via lysine residues or glycerine residues.

They can also include non-branched mPEG-Succinimidyl Propionate (mPEG-SPA), of the general formula:

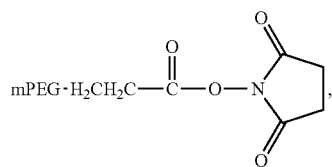

in which mPEG is about 20 KD or about 30 KD. In a specific embodiment, the reactive ester is —O—CH2CH2-CO2-NHS. Compounds of this structure are sold by Nektar Therapeutics as catalog numbers #2M4M0P01.

The reagents can also include a branched PEG linked through glycerol, such as the Sunbright™ series from NOF Corporation, Japan. Specific, non-limiting examples of these reagents are:

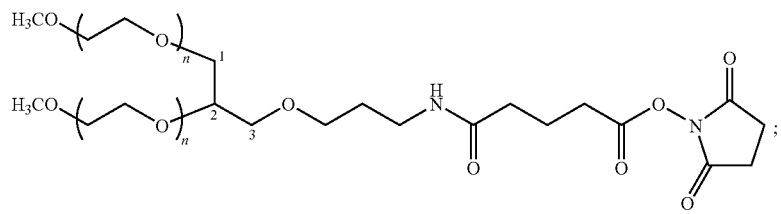

(SUNBRIGHT GL2-400GS2)

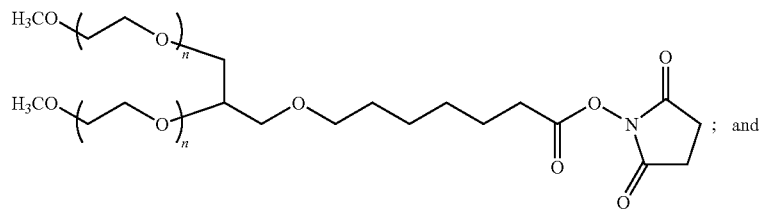

(SUNBRIGHT GL2-400HS) ; and

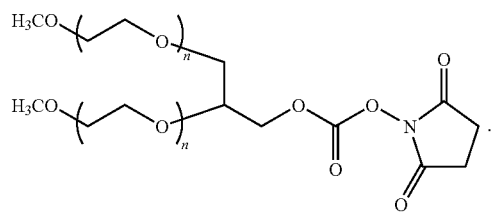

(SUNBRIGHT GL2-400TS)

The reagents can also include non-branched Succinimidyl alpha-methylbutanoate (mPEG-SMB) of the general formula:

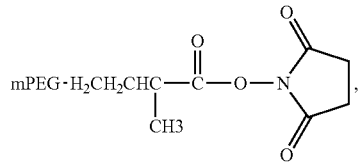

in which mPEG is between 10 and 30 KD. In a subembodiment, the reactive ester is —O—CH$_2$CH$_2$CH(CH$_3$)—CO$_2$—NHS. Compounds of this structure are sold by Nektar Therapeutics as catalog numbers cat#2M4K0R01.

PEG reagents can also include nitrophenyl carbonate linked PEGs, such as of the following structure:

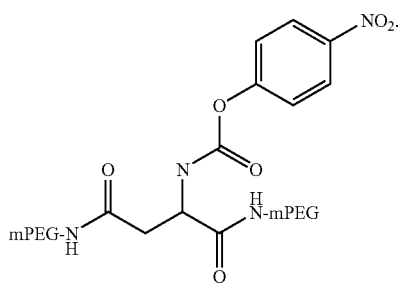

Compounds of this structure are commercially available, for example from Sunbio, Inc. Compounds including nitrophenyl carbonate can be conjugated to primary amine containing linkers. In this reaction, the O-nitrophenyl serves as the leaving group, leaving a structure [mPEG]$_n$-NH—CO—NH-linker-ligand.

PEGs with thiol-reactive groups that can be used with a thiol-modified linker, as described above, include compounds of the general structure:

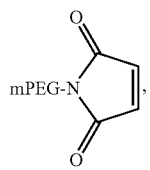

in which mPEG is about 10, about 20 or about 30 KD. Additionally, the structure can be branched, such as

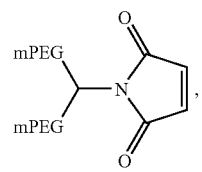

in which each mPEG is about 10, about 20, or about 30 KD and the total mass is about 20, about 40, or about 60 KD. Branched PEGs with thiol reactive groups that can be used with a thiol-modified linker, as described above, include compounds of the general structure (need structure), in which the branched PEG has a total molecular weight of about 40 or 60 KD (where each mPEG is 20 or 30 KD). Compounds of this general structure are commercially available, for example from Nektar Therapeutics, sold as cat#2F2M0P01, cat#2D3Y0T01, or cat#2D3Y0V01. PEG reagents can also be of the following structure:

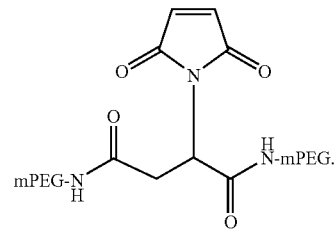

PEG reagents of this structure are sold, for example, by Sunbio, Inc. PEG-maleimide pegylates thiols of the target compound in which the double bond of the maleimic ring breaks to connect with the thiol. The rate of reaction is pH dependent and, in one embodiment, is carried out between pH 6 and 10, or between pH 7 and 9 or about pH 8.

In a general embodiment, the aptamers of the invention have the general structure:

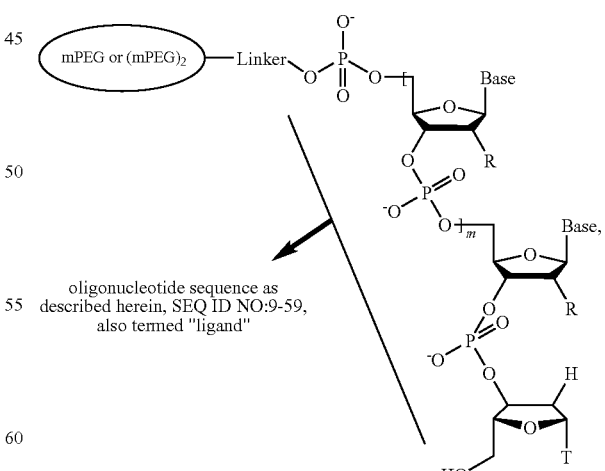

or a pharmaceutically acceptable salt thereof.

In one subembodiment, the aptamer has the following structure:

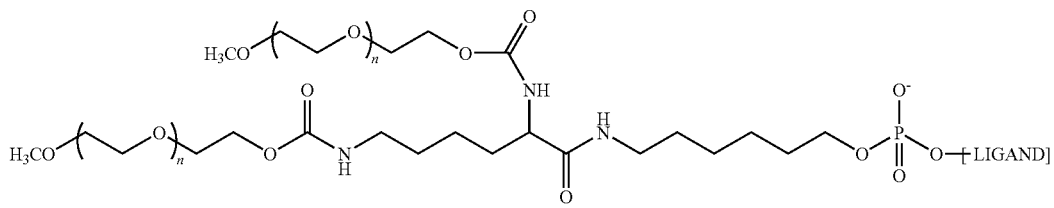

Ligand = oligonucleotide of SEQ ID NO:59
n = approximately 450 or a pharmaceutically acceptable salt thereof.

In another subembodiment, the aptamer is of the structure:

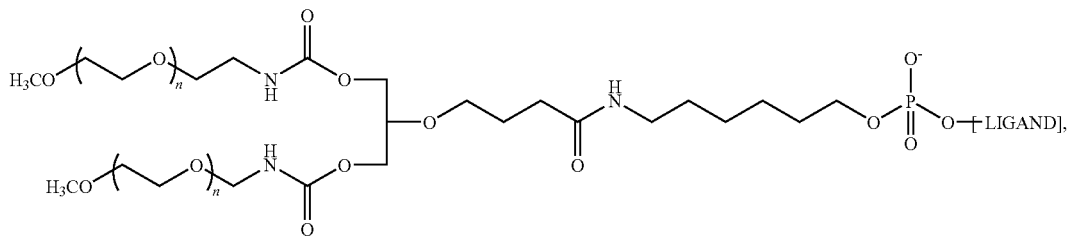

Ligand = oligonucleotide of SEQ ID NO:59
n = approximately 450 or a pharmaceutically acceptable salt thereof.

In another subembodiment, the aptamer is of the structure:

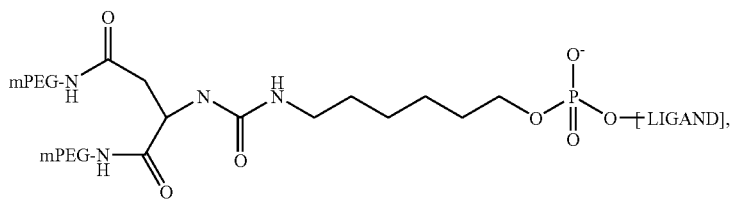

Ligand = oligonucleotide of SEQ ID NO:59
n = approximately 450 or a pharmaceutically acceptable salt thereof.

In another subembodiment, the aptamer is of the structure:

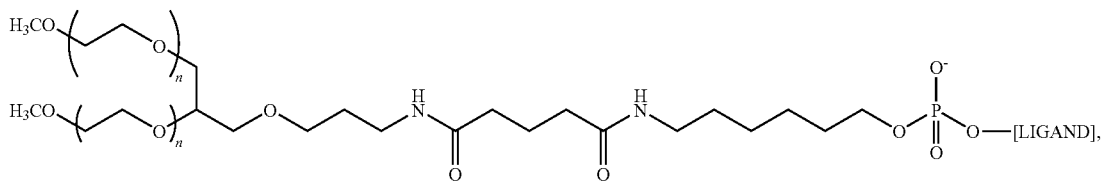

Ligand = oligonucleotide of SEQ ID NO:59
n = approximately 450 or a pharmaceutically acceptable salt thereof.

In another subembodiment, the aptamer is of the structure:

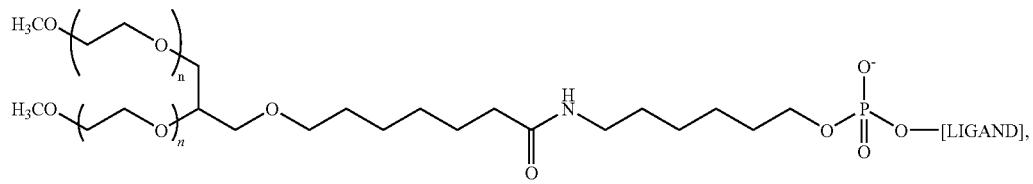

Ligand = oligonucleotide of SEQ ID NO:59
n = approximately 450 or a pharmaceutically acceptable salt thereof.

In another subembodiment, the aptamer is of the structure:

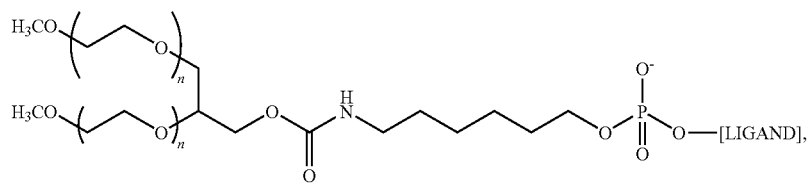

Ligand = oligonucleotide of SEQ ID NO:59
n = approximately 450 or a pharmaceutically acceptable salt thereof.

In another subembodiment, the aptamer is of the structure:

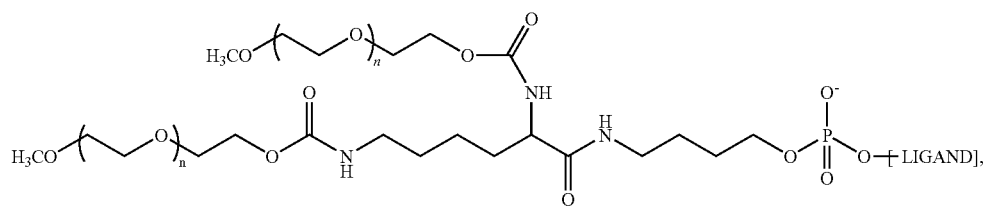

Ligand = oligonucleotide of SEQ ID NO:59
n = approximately 450 or a pharmaceutically acceptable salt thereof.

In another subembodiment, the aptamer is of the structure:

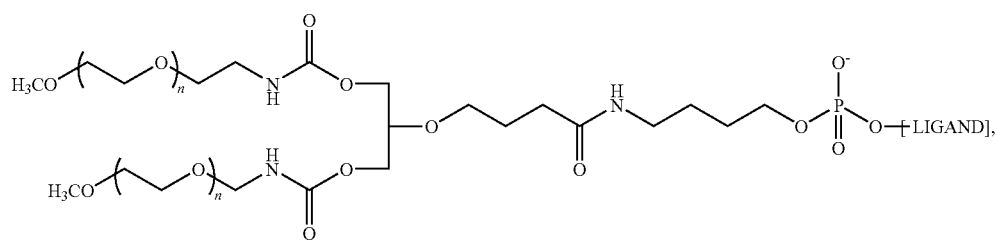

Ligand = oligonucleotide of SEQ ID NO:59
n = approximately 450 or a pharmaceutically acceptable salt thereof.

In another subembodiment, the aptamer is of the structure:

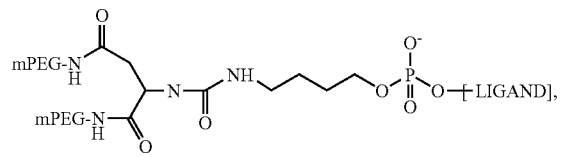

Ligand = oligonucleotide of SEQ ID NO:59
n = approximately 450 or a pharmaceutically acceptable salt thereof.

In another subembodiment, the aptamer is of the structure:

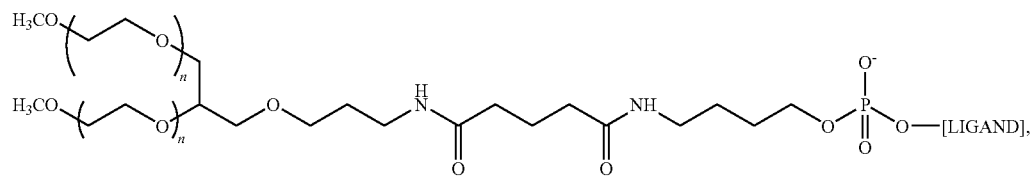

Ligand = oligonucleotide of SEQ ID NO:59
n = approximately 450 or a pharmaceutically acceptable salt thereof.

In another subembodiment, the aptamer is of the structure:

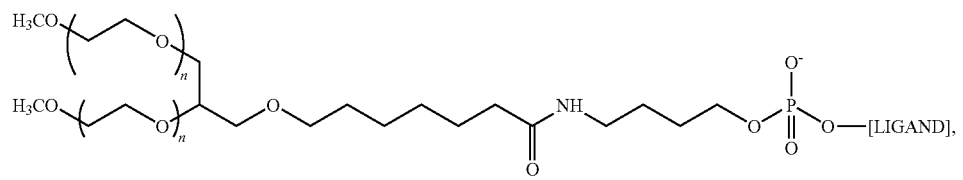

Ligand = oligonucleotide of SEQ ID NO:59
n = approximately 450 or a pharmaceutically acceptable salt thereof.

In another subembodiment, the aptamer is of the structure:

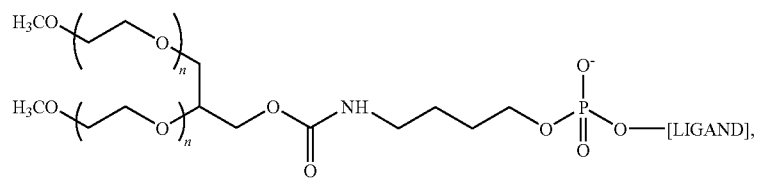

Ligand = oligonucleotide of SEQ ID NO:59
n = approximately 450 or a pharmaceutically acceptable salt thereof.

In yet another subembodiment, the aptamer is of the structure:

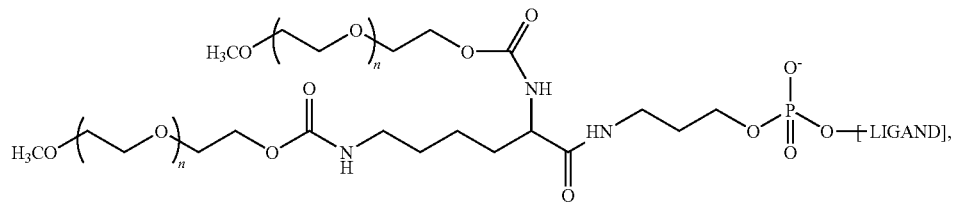

Ligand = oligonucleotide of SEQ ID NO:59
n = approximately 450 or a pharmaceutically acceptable salt thereof.

In another subembodiment, the aptamer is of the structure:

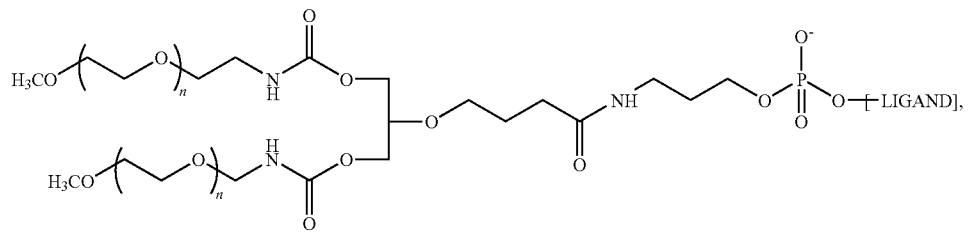

Ligand = oligonucleotide of SEQ ID NO:59
n = approximately 450 or a pharmaceutically acceptable salt thereof.

In yet another subembodiment, the aptamer is of the structure:

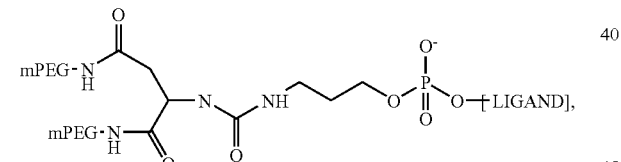

Ligand = oligonucleotide of SEQ ID NO:59
n = approximately 450 or a pharmaceutically acceptable salt thereof.

In yet another subembodiment, the aptamer is of the structure:

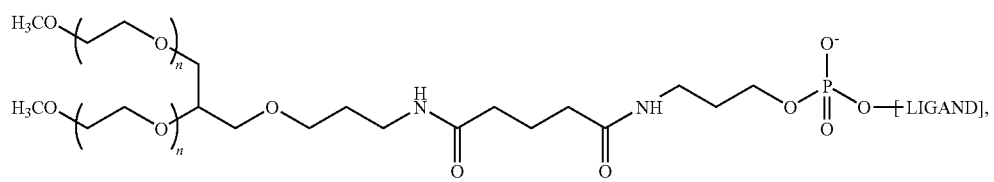

Ligand = oligonucleotide of SEQ ID NO:59
n = approximately 450 or a pharmaceutically acceptable salt thereof.

In yet another subembodiment, the aptamer is of the structure:

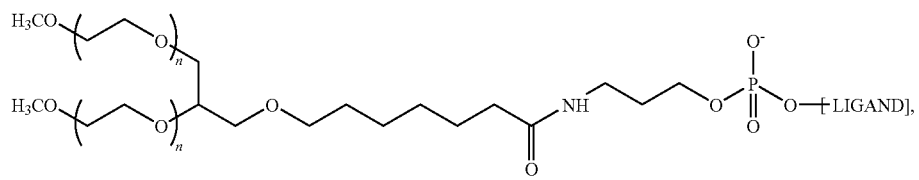

Ligand = oligonucleotide of SEQ ID NO:59
n = approximately 450 or a pharmaceutically acceptable salt thereof.

In yet another subembodiment, the aptamer is of the stricture:

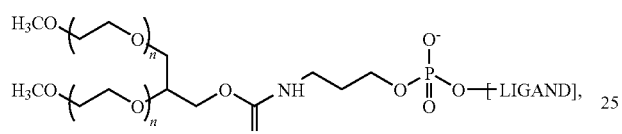

Ligand = oligonucleotide of SEQ ID NO:59
n = approximately 450 or a pharmaceutically acceptable salt thereof.

In another subembodiment, the aptamer is of the structure:

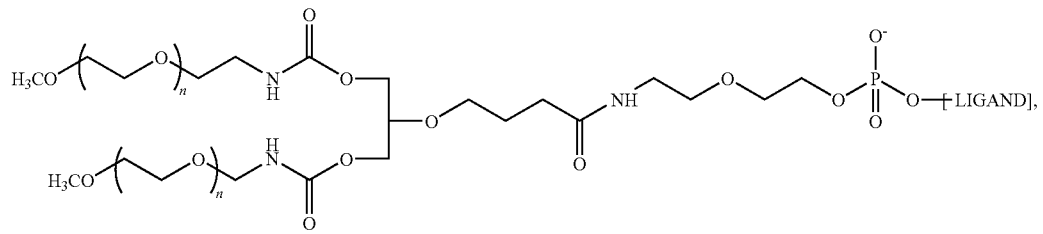

Ligand = olignucleotide of SEQ ID NO:59
n = approximately 450 or a pharmaceutically acceptable salt thereof.

In another subembodiment, the aptamer is of the structure:

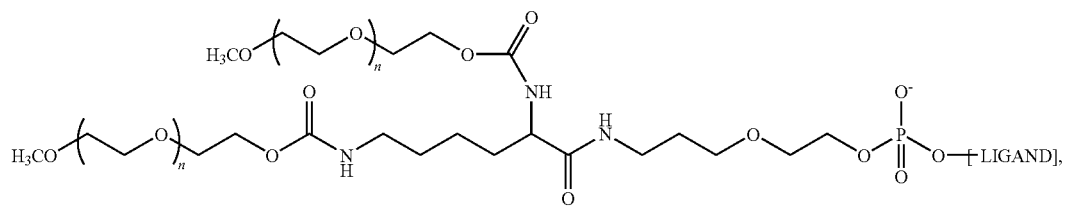

Ligand = olignucleotide of SEQ ID NO:59
n = approximately 450 or
a pharmaceutically acceptable salt thereof.

In another subembodiment, the aptamer is of the structure:

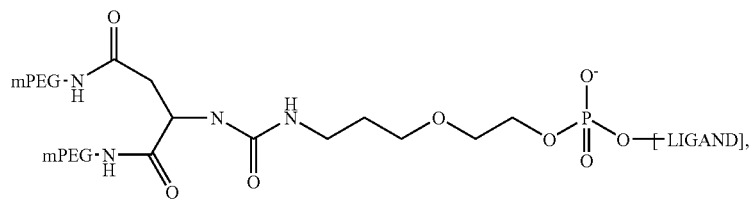

Ligand = oligonucleotide of SEQ ID NO:59
n = approximately 450 or a pharmaceutically acceptable salt thereof.

In another subembodiment, the aptamer is of the structure:

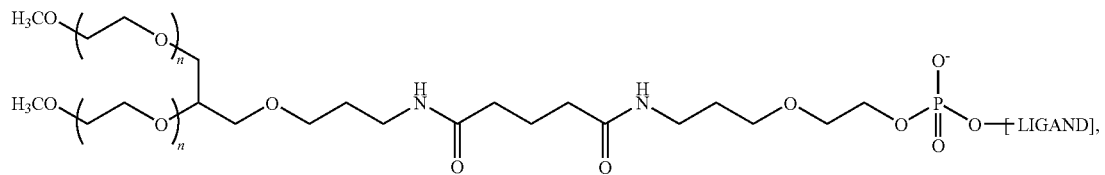

Ligand = oligonucleotide of SEQ ID NO:59
n = approximately 450 or a pharmaceutically acceptable salt thereof.

In another subembodiment, the aptamer is of the structure:

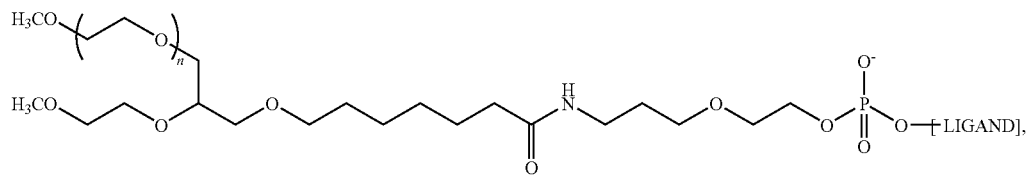

Ligand = oligonucleotide of SEQ ID NO:59
n = approximately 450 or a pharmaceutically acceptable salt thereof.

In another subembodiment, the aptamer is of the structure:

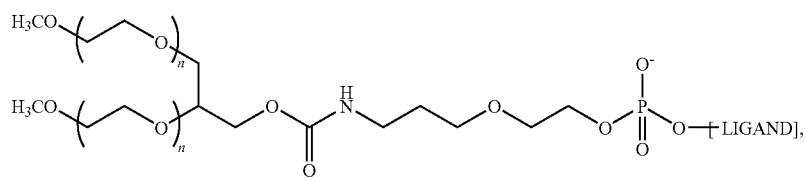

Ligand = oligonucleotide of SEQ ID NO:59
n = approximately 450 or a pharmaceutically acceptable salt thereof.

In another subembodiment, the aptamer is of the structure:

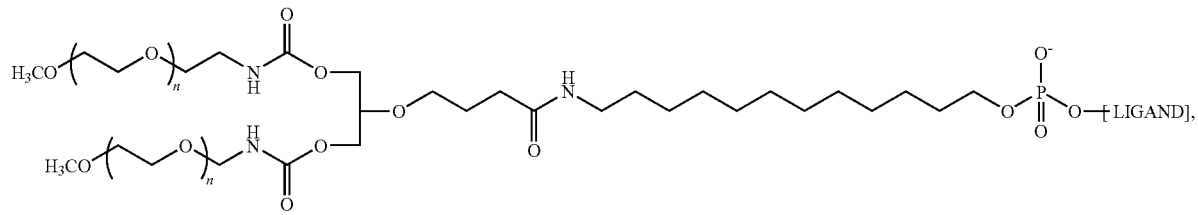

Ligand = oligonucleotide of SEQ ID NO:59
n = approximately 450 or a pharmaceutically acceptable salt thereof.

In another subembodiment, the aptamer is of the structure:

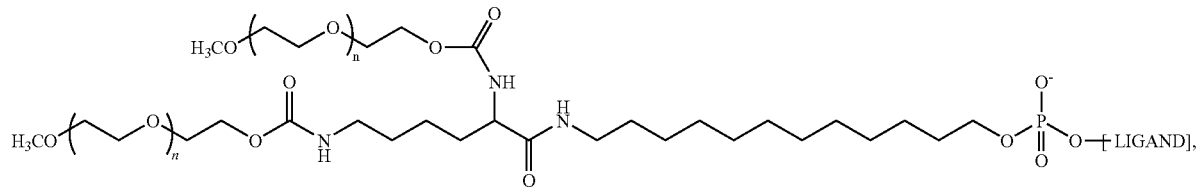

Ligand = oligonucleotide of SEQ ID NO:59
n = approximately 450 or a pharmaceutically acceptable salt thereof.

In another subembodiment, the aptamer is of the structure:

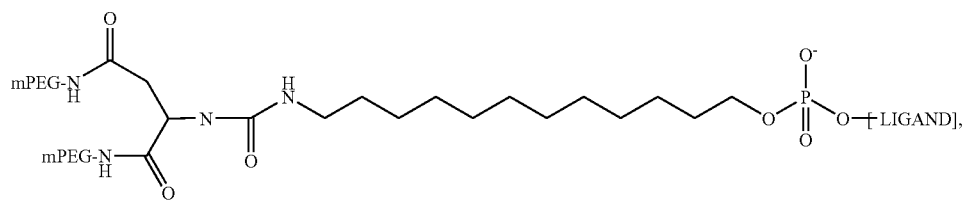

Ligand = oligonucleotide of SEQ ID NO:59
n = approximately 450 or a pharmaceutically acceptable salt thereof.

In another subembodiment, the aptamer is of the structure:

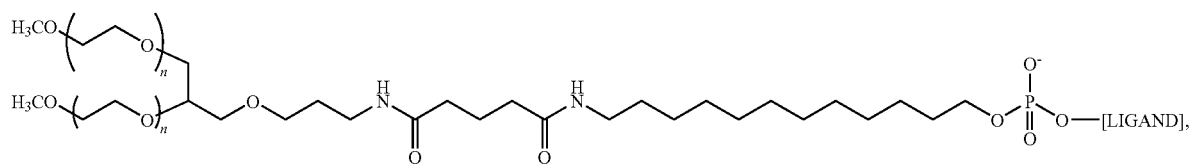

Ligand = oligonucleotide of SEQ ID NO:59
n = approximately 450 or a pharmaceutically acceptable salt thereof.

In another subembodiment, the aptamer is of the structure:

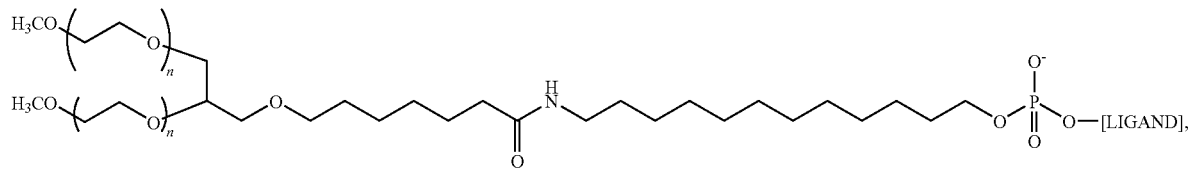

Ligand = oligonucleotide of SEQ ID NO:59
n = approximately 450 or a pharmaceutically acceptable salt thereof.

In another subembodiment, the aptamer is of the structure:

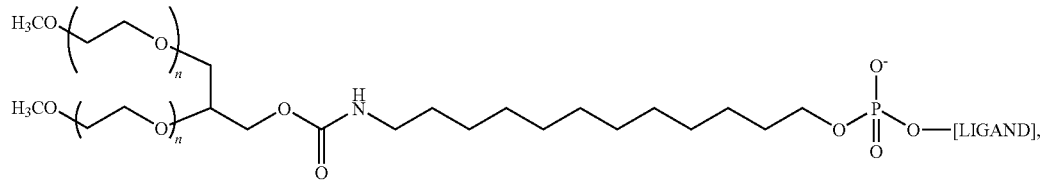

Ligand = oligonucleotide of SEQ ID NO:59
n = approximately 450 or a pharmaceutically acceptable salt thereof.

In another subembodiment, the aptamer is of the structure:

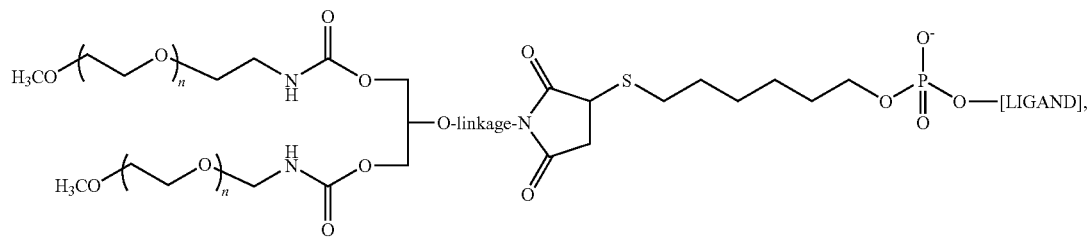

Ligand = oligonucleotide of SEQ ID NO:59
n = approximately 450 or a pharmaceutically acceptable salt thereof.

In another subembodiment, the aptamer is of the structure:

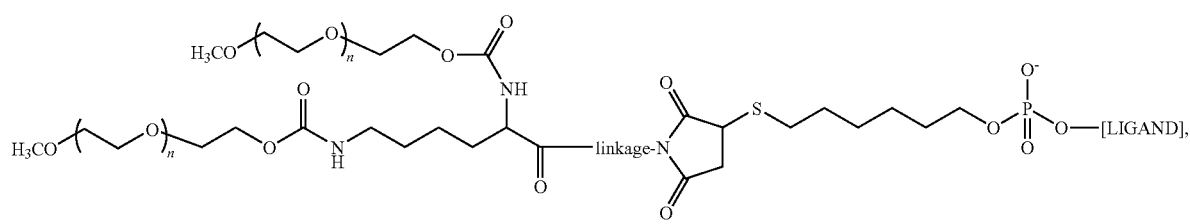

Ligand = oligonucleotide of SEQ ID NO:59
n = approximately 450 or a pharmaceutically acceptable salt thereof.

The aptamers or antidotes of the invention can also include other conjugate groups covalently bound to functional groups such as primary or secondary hydroxyl groups. Conjugate groups of the invention include polyamines, polyamides, polyethylene glycols, polyethers, groups that enhance the pharmacodynamic properties of oligomers, and groups that enhance the pharmacokinetic properties of oligomers. Groups that enhance the pharmacodynamic properties, in the context of this invention, include groups that improve oligomer bioavailability, enhance oligomer resistance to degradation, and/or strengthen sequence-specific hybridization with RNA.

4. Process of Manufacture of Aptamer

The improved aptamers described herein can be manufactured using techniques known in the art. For example, U.S. patents have issued describing methods of large scale manufacturing that can be used to manufacture aptamers. Caruthers et al., for example, describe in U.S. Pat. Nos. 4,973,679; 4,668,777; and 4,415,732 a class of phosphoramidite compounds that are useful in the manufacture of oligonucleotides. In another series of patents, Caruthers et al. disclose a method of synthesizing oligonucleotides using an inorganic polymer support. See, e.g., U.S. Pat. Nos. 4,500,707, 4,458,066 and 5,153,319. In still another series of patents, Caruthers et al. discloses a class of nucleoside phosphorodithioates that can be used to manufacture oligonucleotides. See, e.g., U.S. Pat. Nos. 5,278,302, 5,453,496 and 5,602,244.

In a specific embodiment, manufacture of improved nucleic acid ligands of the invention is a multi-step process involving solid phase chemical synthesis of the oligonucleotide strand; cleavage and deprotection of the crude oligonucleotide; purification by preparative anion exchange chromatography; desalting followed by PEGylation; purification of the PEGylated oligonucleotide by preparative anion exchange chromatography to remove unPEGylated oligonucleotide impurities; ultrafiltration for desalting; concentration and lyophilization of the final product.

Chemical synthesis via phosphoramidite chemistry involves sequential coupling of activated monomers to an elongating polymer, one terminus of which is covalently attached to a solid support matrix. The general steps include protecting a 3'-hydroxy of a nucleoside, coupling a 5'-carbon to a solid support, deprotecting, coupling a phosphoramidate-linked, protected nucleoside to the 3'-hydroxy, deprotecting, sequentially reacting phosphoramidate-linked nucleosides to build the molecule, coupling the terminal 5'-nucleoside with a linker and reacting with an inert carrier, such as a linked PEG. The solid phase approach allows for easy purification of the reaction product at each step in the synthesis by simple solvent washing of the solid phase.

In one embodiment, the oligonucleotides are sequentially assembled from the 3'-end towards the 5'-end by deprotecting the 5'-end of the support-bound molecule, allowing the support-bound molecule to react with an incoming tetrazole-activated phosphoramidite monomer, oxidizing the resulting phosphite triester to a phosphate triester, and blocking any unreacted hydroxyl groups by acetylation (capping) to prevent non-sequential coupling with the next incoming monomer to form a "deletion sequence". This sequence of steps is repeated for subsequent coupling reactions until the full-length oligonucleotides are synthesized. Due to the presence of a 3'-3' linkage at the 3' end and a C-6 linker for PEGylation at the 5' end, the synthesis is modified at the first and last step to accommodate these changes.

The overall cycle is schematically shown in Scheme 1 for the synthesis of the crude material.

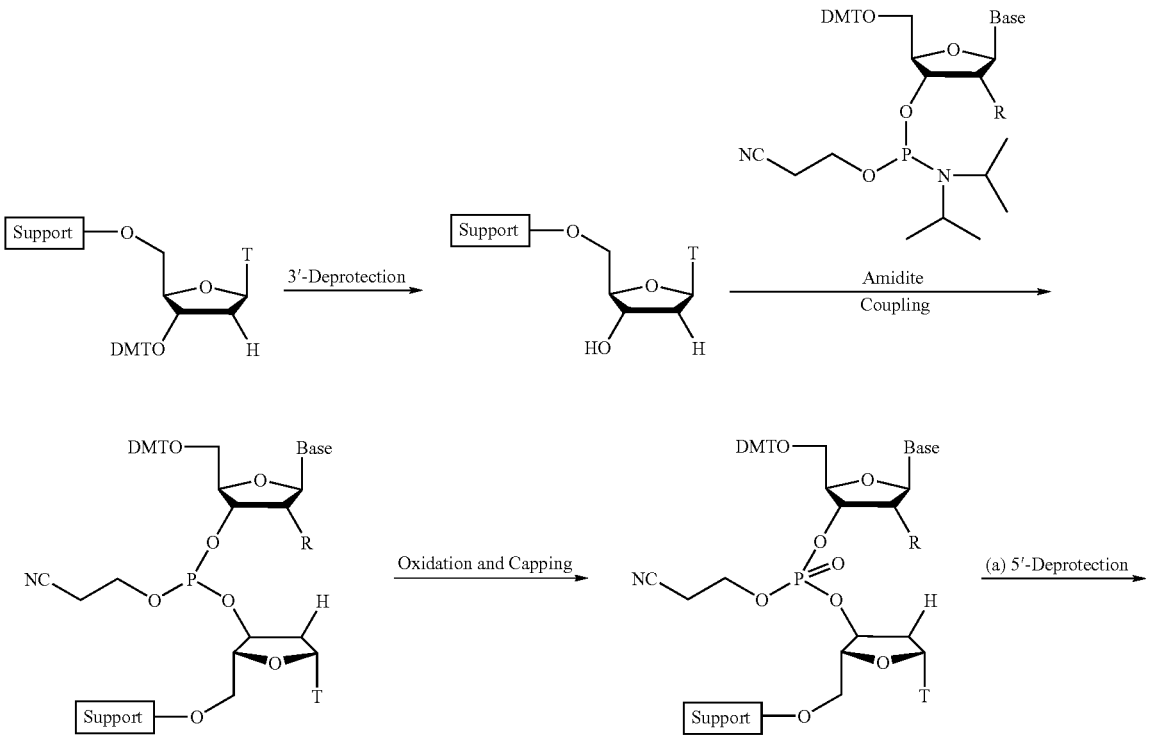

Scheme 1. Solid Phase Synthesis

-continued
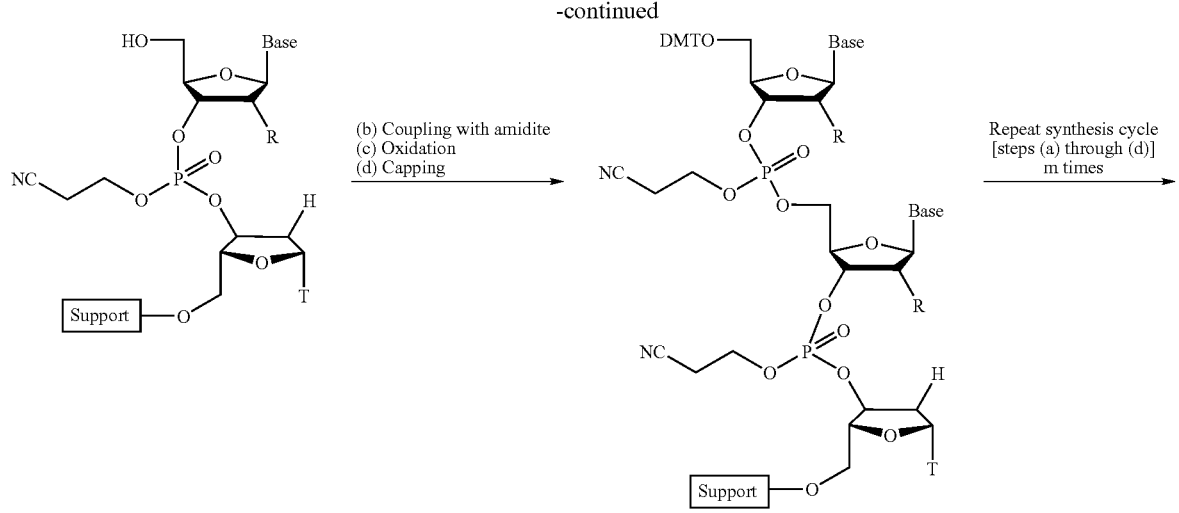
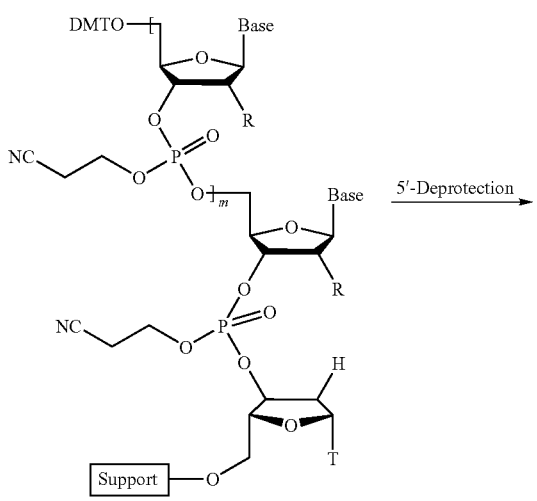
5'-Deprotection
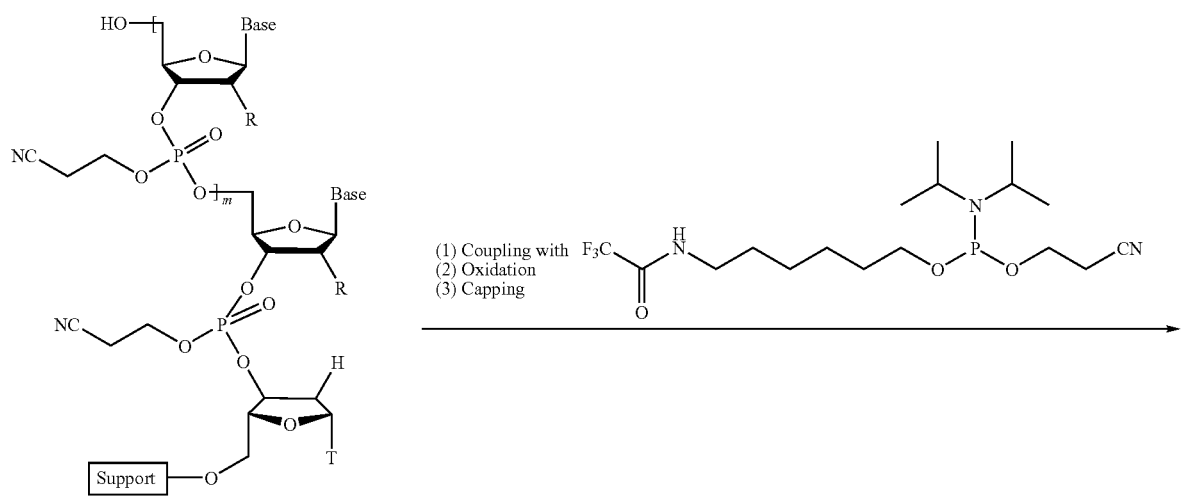
(1) Coupling with
(2) Oxidation
(3) Capping -continued

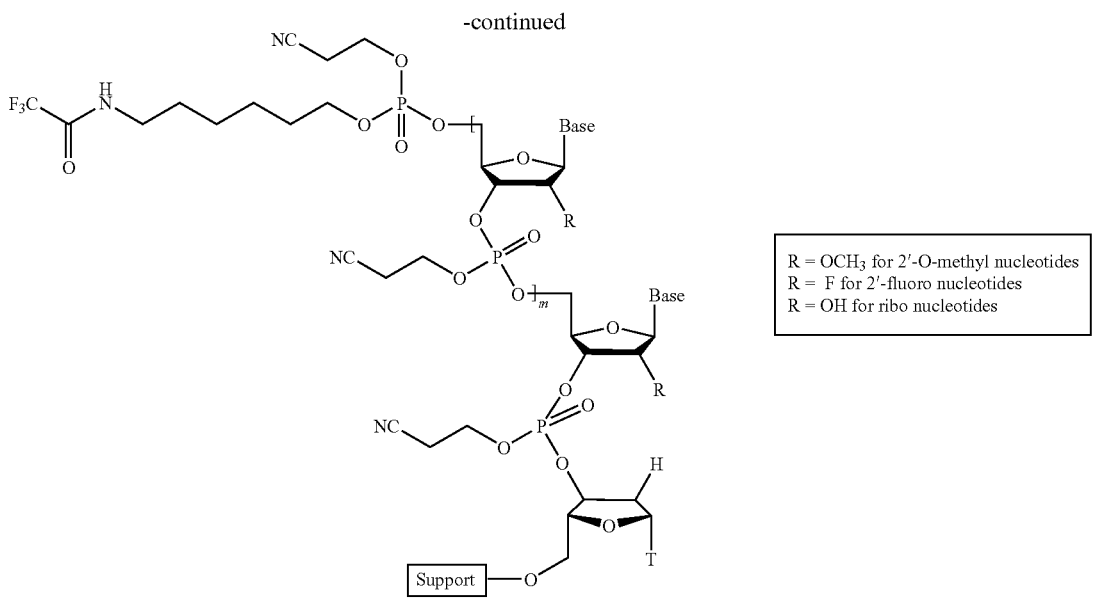

R = OCH₃ for 2'-O-methyl nucleotides
R = F for 2'-fluoro nucleotides
R = OH for ribo nucleotides Cleavage and Deprotection The oligonucleotide can then be cleaved from the solid support and protecting groups on the linker are removed. The support-attached intermediate is cleaved using basic conditions at an elevated temperature. The temperature can be from about 40 to about 55° C., or from about 42 to about 50° C., or from about 45 to about 50° C. An exemplary reaction is carried out in ammonium hydroxide and tert-butylamine. The protecting groups on the linker are removed by incubation with an appropriate deprotecting reagent at reduced temperature. An exemplary deprotecting reagent is triethylamine trihydrofluoride.

In a specific example, upon completion of synthesis, the solid-support and associated oligonucleotide are transferred to a filter funnel, dried under vacuum and transferred to a reaction vessel. Ammonium hydroxide (28-30%) and tert-butylamine are added and the mixture is heated to approximately 45° C. for approximately 15 hours to effect cleavage from the solid support, removal of the cyanoethyl phosphate protecting group, deprotection of exocyclic amine protecting groups as well as removal of the trifluoroacetyl group from the linker. The sample is cooled and the 2'-TBDMS protecting group is then cleaved by addition of Et₃N.3HF in DMSO followed by heating the sample to 45° C. for up to 5 hours to yield the crude oligoribonucleotide. The mixture is filtered under vacuum to remove the waste solid support. The reaction is quenched with glacial acetic acid to provide a pH neutral solution of crude product.

Scheme 1. (continued)

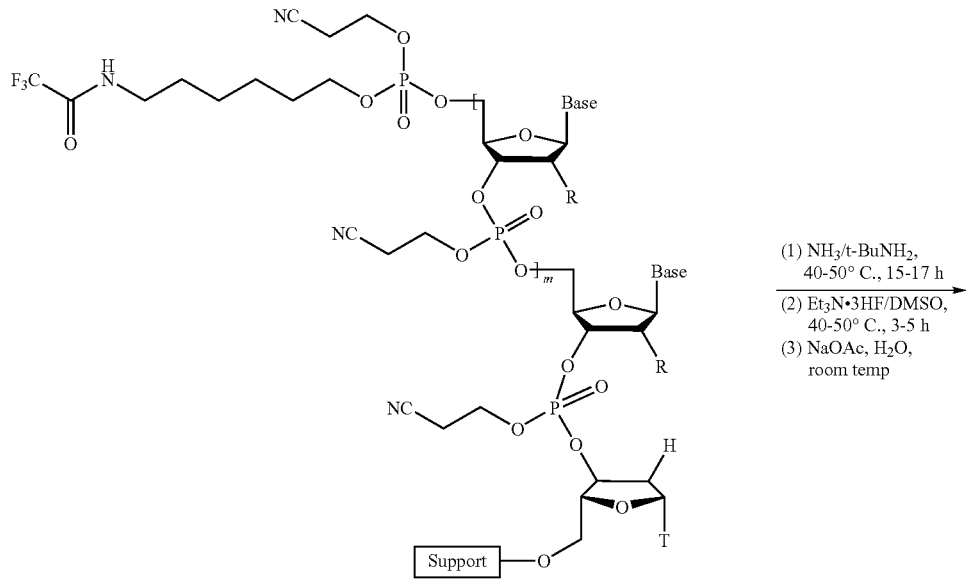

(1) NH₃/t-BuNH₂,
40-50° C., 15-17 h
(2) Et₃N•3HF/DMSO,
40-50° C., 3-5 h
(3) NaOAc, H₂O,
room temp -continued

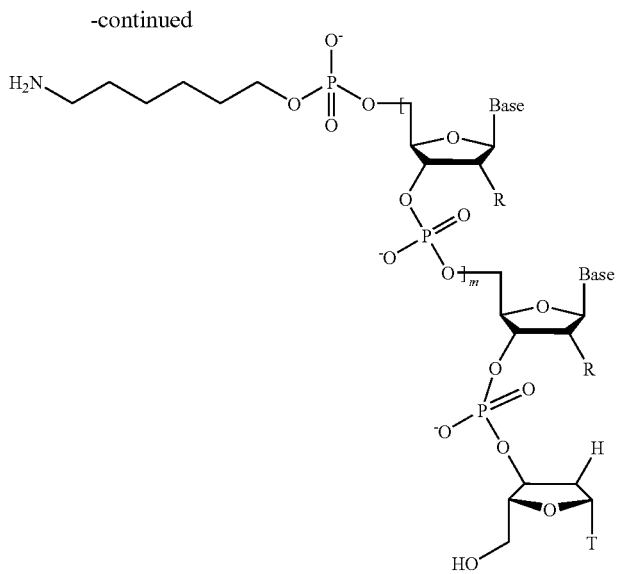

Anion Exchange Purification

The cleaved oligonucleotide can be purified using any techniques known in the art. In one embodiment, the oligonucleotide is purified by ion exchange chromatography.

In a specific example, the crude oligonucleotide is purified by preparative anion exchange chromatography using column chromatography, for example on a TosoBiosep TSK Gel SuperQ-5PW column. The purification can be performed using standard reagents and can be performed at elevated temperature (above room temperature). In a specific embodiment, the purification is performed at approximately 75° C. In a specific example, the reagents include increasing concentrations of sodium bromide as an eluting reagent. In one embodiment, the gradient is made of 10% ACN, 20 mM sodium phosphate, pH 8.0 (Buffer A) and 10% ACN, 20 mM sodium phosphate and 1.0M NaBr, pH 8.0 (Buffer B). Purification is accomplished by eluting the product from the column through a controlled increase in sodium bromide concentration in the buffer system by increasing the proportion of Buffer B. Fractions are collected and analyzed, for example by UV and IP RP-HPLC. When necessary, the fractions are combined to yield a product pool of the desired purity, desalted by ultrafiltration (e.g. using 1 KD Polyethersulfone (PES) Pall Filtron UF Cassettes) and concentrated at about 40° C. and about 80 mbar pressure using a rotary evaporator. The concentrated product is stored at 2-8° C.

PEGylation

For PEGylation of compounds that react with linkers containing primary amines, the purified and concentrated intermediate from above is reacted with a PEG reagent as described herein at a pH between about pH 7-10, or between about pH 8-10, or between about pH 8.5-10, or between about pH 8.8-9.8. As an example, a 40 KD mPEG-linked reagent can be incubated with the purified oligonucleotide at about 25° C. in 0.1 M sodium borate buffer (pH about 8.8) for 25-30 min. The reaction is shown in Scheme 2.

Scheme 2. PEGylation

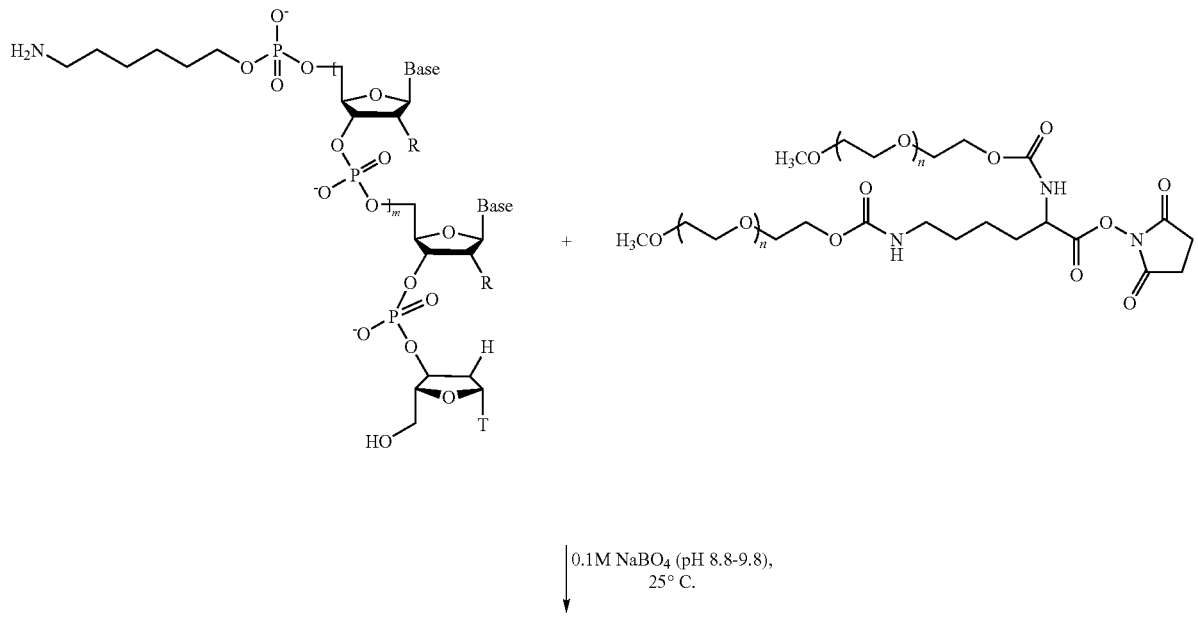

0.1M NaBO$_4$ (pH 8.8-9.8), 25° C.

-continued

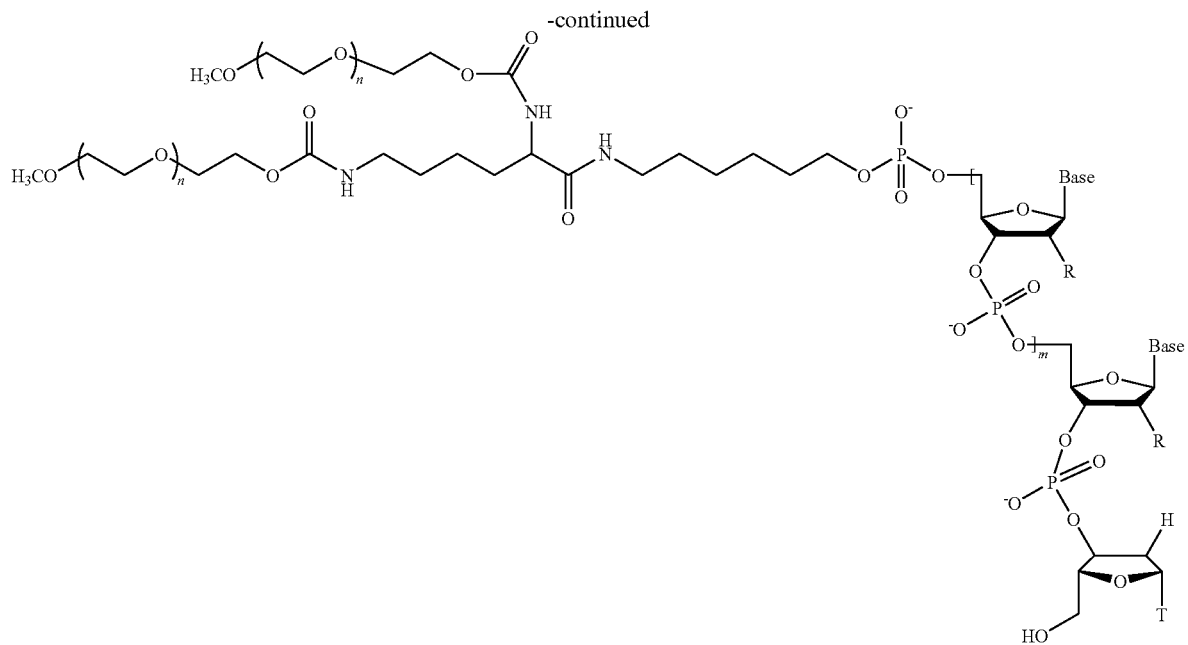

n = approximately 450

For linkers that include free thiol, the purified and concentrated intermediate is reacted with an appropriate PEG (i.e. PEG-Mal) at pH from about 6-8 or from about 6.5-7.5. Thiol PEGylation is specific for free thiols on biological reagents using mPEG-MAL. Coupling of maleimide to thiol groups is highly specific for thiols at ca. pH 6.5-7.5 in the presence of other functional groups. Reaction with a thiol moiety generates a stable 3-thiosuccinimidyl ether linkage.

5. Aptamer Antidotes

It is important to be able to release blood coagulation factors from inhibition. Life threatening diseases can result from over-inhibition of the blood coagulation factors such as Factor IX. For example, hemophilia B results from deficiencies in factor IL. All patients with hemophilia B have prolonged coagulation time and decreased factor IX clotting activity. Like hemophilia A, there are severe, moderate and mild forms of hemophilia B and reflect the factor IX activity in plasma.

Therefore, another embodiment of the invention includes an antidote paired with the aptamer of the invention. Antidotes or modulators can include any pharmaceutically acceptable agent that can bind an aptamer and modify the interaction between that aptamer and its target molecule (e.g., by modifying the structure of the aptamer) in a desired manner. Examples of such antidotes include (A) oligonucleotides complementary to at least a portion of the aptamer sequence (including ribozymes or DNAzymes or peptide nucleic acids (PNAs)), (B) nucleic acid binding peptides, polypeptides or proteins (including nucleic acid binding tripeptides (see, generally, Hwang et al. (1999) Proc. Natl. Acad. Sci. USA 96:12997), and (C) oligosaccharides (e.g. aminoglycosides (see, generally, Davis et al. (1993) Chapter 8, p. 185, RNA World, Cold Spring Harbor Laboratory Press, eds. Gestlaad and Atkins; Werstuck et al. (1998) Science 282:296; U.S. Pat. Nos. 5,935,776 and 5,534,408). (See also the following which disclose types of antidotes that can be used in accordance with the present invention: Chase et al. (1986) *Ann. Rev. Biochem.* 56:103, Eichorn et al. (1968) *J. Am. Chem. Soc.* 90:7323, Dale et al. (1975) *Biochemistry* 14:2447 and Lippard et al. (1978) *Acc. Chem. Res.* 11:211).

In one embodiment, the antidote oligonucleotide reverses or neutralizes at least 25%, 50%, 75%, 80% or 90% of the anticoagulant activity of the aptamer. The antidote generally has the ability to substantially bind to a nucleic acid ligand in solution at antidote concentrations of less than one 1 μM, or less than 0.1 μM and more preferably less than 0.01 μM. In one embodiment, the antidote reduces the biological activity of the aptamer by 50%.

Complementary Oligonucleotides

In one embodiment, the improved antidote of the invention is an oligonucleotide that comprises a sequence complementary to at least a portion of the targeted aptamer sequence. Absolute complementarity is not required. The sequence in one embodiment has sufficient complementarity to be able to hybridize with the aptamer. The ability to hybridize will depend on both the degree of complementarity and the length of the antisense nucleic acid. Advantageously, the antidote oligonucleotide comprises a sequence complementary to 6-25 consecutive nucleotides of the targeted aptamer, preferably, 8-20 consecutive nucleotides, more preferably, 10-15 consecutive nucleotides. In specific aspects the antidote is at least 10-25 nucleotides, at least 15-25, at least 20-25, at least 14, 17 or at least 25 nucleotides long. The antidotes of the invention can be DNA or RNA or chimeric mixtures or derivatives or modified versions thereof, single-stranded.

Formation of duplexes by binding of complementary pairs of short oligonucleotides is a fairly rapid reaction with second order association rate constants generally between $1 \times 10^6$ and $3 \times 10^5$ $M^{-1}s^{-1}$. Stability of short duplexes can be highly dependent on the length and base-composition of the duplex. The thermodynamic parameters for formation of short nucleic acid duplexes have been rigorously measured, resulting in nearest-neighbor rules for all possible base pairs such that accurate predictions of the free energy, $T_m$ and thus half-life of a given oligoribonucleotide duplex can be calculated (e.g., Xia et al. (1998) *Biochem.* 37:14719; see also Eguchi et al. (1991) Antigensis RNA, *Annu. Rev. Biochem.* 60:631).

In a specific embodiment, the present invention provides improved antidotes that specifically and rapidly reverse the anticoagulant and antithrombotic effects of the improved aptamers that target components of the coagulation pathway, in particular the aptamers of FIX and FIXa. The antidotes can be administered to reverse the aptamer activity by a physician or other health care provider. In specific embodiments, the improved antidotes according to the present invention are nucleic acids corresponding to the sequences: (5'-3') sequence: cgcgguauaguccccau (Apt/AD; SEQ ID NO:1); (5'-3') sequence: cgcgguauaguccc (Apt6/AD SEQ ID NO:2); (5'-3') sequence: cgcgguauaguccac (Apt7/AD; SEQ ID NO:3); (5'-3') sequence: cgcgguauaguccauc (Apt8/AD; SEQ ID NO:4); (5'-3') sequence: cgcgguauagucag (Apt9/AD; SEQ ID NO:5); (5'-3') sequence: cgcgguauagucagg (Apt10/AD; SEQ ID NO:6); (5'-3') sequence: cgcgguauagucagag (Apt11/AD; SEQ ID NO:7); (5'-3') sequence: cgcgguauaguccucac (Apt14/AD; SEQ ID NO:8), or any modification or derivative thereof. The antidote sequence can be at least 20%, 50%, 75% or 90% homologous to the sequence of the corresponding aptamer. In one embodiment, the antisense sequence is separately administered.

In one embodiment, the antidote has the structure 2'-methoxy-2'-deoxycytidylyl-(3'-5')-2'-methoxy-2'-deoxyguanylyl-(3'-5')-2'-methoxy-2'-deoxycytidylyl-(3'-5')-2'-methoxy-2'-deoxyguanylyl-(3'-5')-2'-methoxy-2'-deoxyguanylyl-(3'-5')-2'-methoxyuridylyl-(3'-5')-2-methoxy-2'-deoxyadenylyl-(3'-5')-2'-methoxyuridylyl-(3',5')-2'-methoxy-2'-deoxyadenylyl-(3'-5')-2'-methoxy-2'-deoxyguanylyl-(3'-5')-2'-methoxyuridylyl-(3'-5')-2'-methoxy-2'-deoxycytidylyl-(3'-5')-2'-methoxy-2'-deoxycytidylyl-(3',5')-2'-methoxy-2'-deoxyadenylyl-(3'-5')-2'-methoxy-2'-deoxycytidine.

Antisense techniques are discussed for example, in Okano, et al. (1991) *J. Neurochem.* 56:560 and "Oligodeoxynucleotides as Antisense Inhibitors of Gene Expression," (1988) CRC Press, Boca Raton, Fla. In one embodiment, oligonucleotide antidotes of the invention are advantageously targeted at single-stranded regions of the aptamer. This can facilitate nucleation and, therefore, the rate of aptamer activity modulation, and also, generally leads to intermolecular duplexes that contain more base pairs than the targeted aptamer. The aptamer to Factor IXa of the present invention may be used to design an antisense oligonucleotide. The antisense oligonucleotide hybridizes to the aptamer in vivo and blocks the binding of the aptamer to factor IXa.

To design an improved antidote to the improved aptamers of the invention, various strategies can be used to determine the optimal binding site. The complimentary oligonucleotides can be "walked" around the aptamer. This "walking" procedure includes, after a minimal consensus ligand sequence has been determined for a given improved aptamer, adding random sequence to the minimal consensus ligand sequence and evolving additional contacts with the target, such as in separate but adjacent domains. A walking experiment can involve two experiments performed sequentially. A new candidate mixture is produced in which each of the members of the candidate mixture has a fixed nucleic acid-region that corresponds to a nucleic acid ligand of interest. Each member of the candidate mixture also contains a randomized region of sequences. According to this method it is possible to identify what are referred to as "extended" nucleic acid ligands, which contain regions that can bind to more than one binding domain of a target.

Changes in the sugar can affect antidote stability, in part because sugar modifications that result in RNA-like oligonucleotides, e.g., 20-fluoro or 20-methoxy, do not appear to serve as substrates for RNase H. Alterations in the orientation of the sugar to the base can also affect RNase H activation. Additionally, backbone modifications influence the ability of oligonucleotides to activate RNase H. Methylphosphonates do not activate it, whereas phosphorothioates are excellent substrates. In addition, chimeric molecules have been studied as oligonucleotides that bind to RNA and activate RNase H. For example, oligonucleotides comprising wings of 20-methoxy phosphonates and a five-base gap of deoxyoligonucleotides bind to their target RNA and activate RNase H.

In one embodiment, 2'-O-methyl modified antidotes (e.g., 2'-O-methyl oligonucleotides) about 15 nucleotides in length can be used, the complementarity of which is staggered by about 5 nucleotides on the aptamer (e.g., oligonucleotides complementary to nucleotides 1-15, 6-20, 11-25, etc.). The impact of tertiary structure of the improved aptamer on the efficiency of hybridization is difficult to predict. Assays described in the Examples that follow can be used to assess the ability of the different oligonucleotides to hybridize to a specific aptamer. The ability of the different oligonucleotide antidotes to increase the rate of dissociation of the aptamer from, or association of the aptamer with, its target molecule can also be determined by conducting kinetic studies using, for example, BIACORE assays. Oligonucleotide antidotes can be selected such that a 5-50 fold molar excess of oligonucleotide, or less, is required to modify the interaction between the aptamer and its target molecule in the desired manner.

The antidotes of the invention may be conjugated to another molecule, e.g., a peptide, a hybridization-triggered cross-linking agent, a transport agent, a hybridization-triggered cleavage agent, etc.

The antisense oligonucleotide may optionally comprise at least one modified base moiety, including but not limited to one selected from 5-fluorouracil, 5-fluorocytosine, 5-bromouracil, 5-bromocytosine, 5-chlorouracil, 5-chlorocytosine, 5-iodouracil, 5-iodocytosine, 5-methylcytosine, 5-methyluracil, hypoxanthine, xantine, 4-acetylcytosine, 5-(carboxyhydroxylmethyl) uracil, 5-carboxymethylamin-O-methyl thiouridine, 5-carboxymethylamin-O-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 6-methylcytosine, N6-adenine, 7-methylguanine, 5-methylamine-O-methyluracil, 5-methoxyamine-O-methyl-2-thiouracil, beta-D-mannosylqueosine, 5'-methoxycarboxymethyluracil, 5-methoxyuracil, 5-methoxycytosine, 2-methylthio-N-isopentenyladenine, uracil oxyacetic acid (v), butoxosine, pseudouracil, queosine, 2-thiocytosine, 5-methyl thiouracil, 2-thiouracil, 4-thiouracil, 5-methyluracil, uracil-5-oxyacetic acid methylester, uracil oxyacetic acid (v), 5-methyl thiouracil, 3-(3-amino-3-N carboxypropyl)urdeil, (acp3)w, and 2,6-diaminopurine.

The antidotes may also include at least one modified sugar moiety selected from the group including, but not limited to, arabinose, 2-fluoroarabinose, xylulose, hexose, 2'-fluororibose, 2'-O-methylribose, 2'-O-methoxyethylribose, 2'-O-propylribose, 2'-O-methylthioethylribose, 2'-O-diethylaminooxyethylribose, 2'-O-(3-aminopropyl)ribose, 2'-O-(dimethylaminopropyl)ribose, 2'-O-(methylacetamido) ribose, and 2'-O-(dimethylaminoethyloxyethyl)ribose. In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiainidate, a methylphosphonate, an alkyl phosphotriester, and a formacetal or analog thereof.

Manufacturing of Antidote

Manufacture of nucleic acid antidotes is a multi-step process involving solid phase chemical synthesis of the oligonucleotide strand; cleavage and deprotection of the crude oligonucleotide; purification by preparative anion exchange chromatography; desalting and lyophilization of the final product.

Chemical synthesis via phosphoramidite chemistry involves sequential coupling of activated monomers to an elongating polymer, one terminus of which is covalently attached to a solid support matrix. The solid phase approach allows for easy purification of the reaction product at each step in the synthesis by simple solvent washing of the support-bound intermediates. The oligonucleotide can be sequentially assembled from the 3'-end towards the 5'-end by deprotecting the 5'-end of the support-bound intermediate, allowing the support-bound intermediate to react with an incoming tetrazole-activated phosphoramidite monomer, oxidizing the resulting phosphite triester to a phosphate triester, and blocking any unreacted hydroxyl groups by acetylation to prevent non-sequential coupling with the next incoming monomer to form a "deletion sequence". This sequence of steps is repeated for subsequent coupling reactions until the full-length oligonucleotides are synthesized.

A specific cycle is shown schematically shown in Scheme 3 for the synthesis of a crude product.

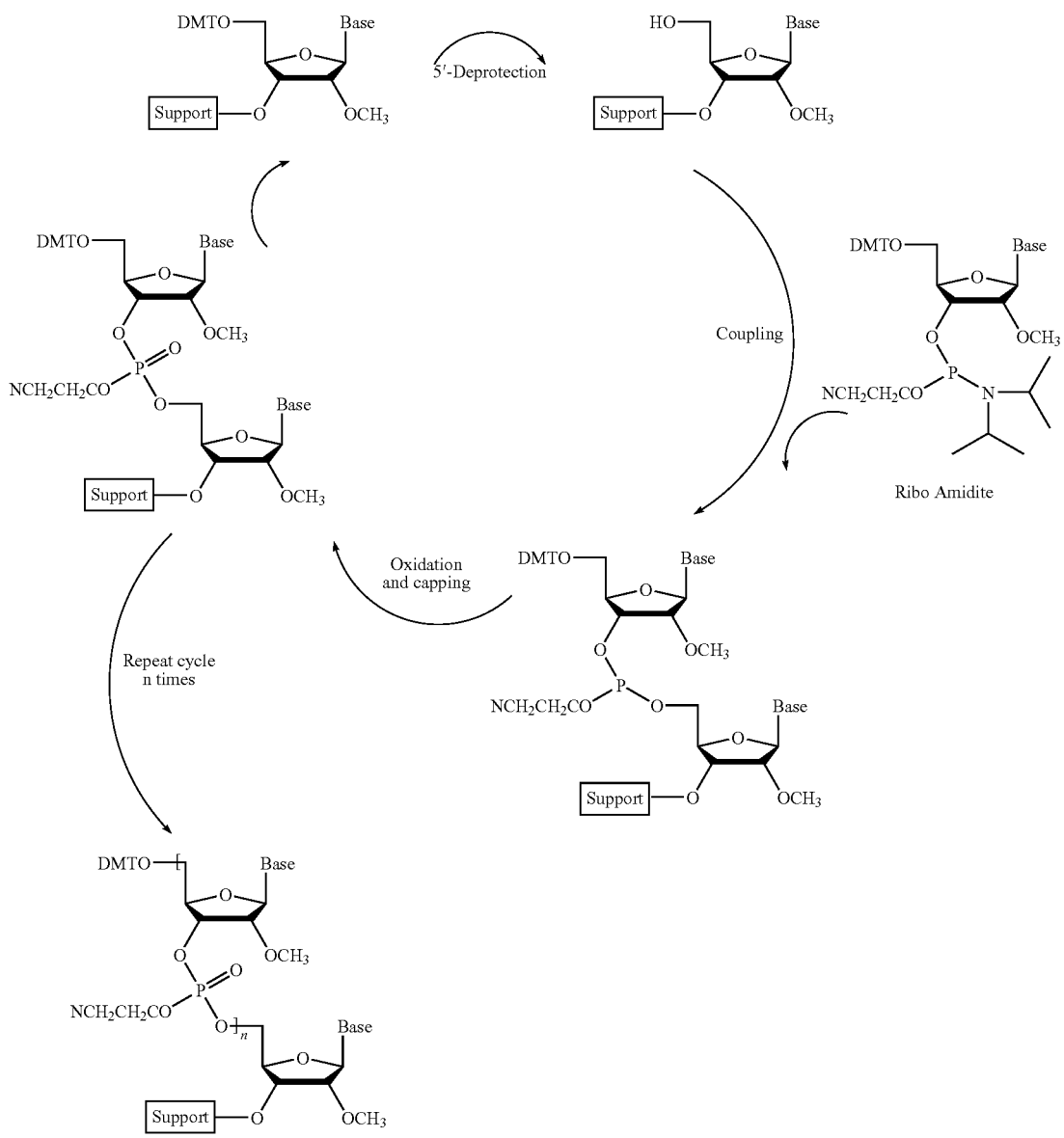

Cleavage and Deprotection

The oligonucleotide can then be cleaved from the solid support and protecting groups on the linker are removed. The support-attached intermediate is cleaved using basic conditions at an elevated temperature. In a specific example, upon completion of the synthesis, the support-bound crude product is transferred to a filter funnel, dried under vacuum and transferred to a reaction vessel. A basic reagent is added to effect cleavage from the solid support, removal of the cyanoethyl phosphate protecting group and deprotection of exocyclic amine protecting groups. The reaction temperature can also be increased to enhance cleavage. In a specific example, the reagent is 30-40% methylamine and the mixture is heated to approximately 45° C. for up to 90 minutes. The mixture is filtered under vacuum to remove the waste solid support. The reaction is quenched with glacial acetic acid to provide a pH neutral solution of crude product.

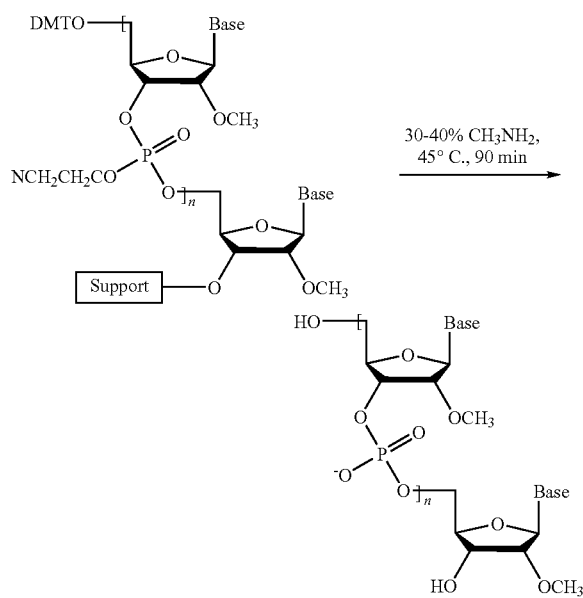

Anion Exchange Purification

The cleaved oligonucleotide can be purified using any techniques known in the art. In one embodiment, the oligonucleotide is purified by ion exchange chromatography.

In a specific example, the crude product is purified by preparative anion exchange chromatography using, for example, a TosoBiosep TSK Gel SuperQ-5PW column. The purification can be performed using standard reagents and can be performed at elevated temperature (above room temperature). In a specific example, the reagents include increasing concentrations of sodium bromide as an eluting reagent. In one embodiment, the gradient is made of 5-35% of Buffer B (10% ACN, 20 mM sodium phosphate and 1.0 M NaBr, pH 8.0) in Buffer A (10% ACN, 20 mM sodium phosphate, pH 8.0). The purification can be performed at approximately 70° C. using. Purification is accomplished by eluting the product from the column through a controlled increase in sodium bromide concentration in the buffer system. Fractions can be collected and analyzed by UV and AX-HPLC. Selected fractions can be combined to yield a product pool with of the desired purity, desalted by ultrafiltration and stored at 2-8° C. Aliquots can be freeze-dried to a dry powder and stored in glass at −15° C. to −25° C.

Ribozymes and DNAzymes

Improved aptamers or antidotes can also be enzymatic nucleic acids. Such a ribozyme or DNAzyme act by first binding to a target RNA or DNA (see Cech U.S. Pat. No. 5,180,818) and then cleaving the target. An enzymatic nucleic acid can repeatedly bind and cleave new targets thereby allowing for inactivation of RNA aptamers. There are at least five classes of ribozymes that each display a different type of specificity. In the case of antidotes, this enzymatic activity can complement or substitute for the introduction of a "suicide position" in the improved aptamer.

The enzymatic nature of a ribozyme may be advantageous over other technologies because the effective concentration of ribozyme necessary to effect a therapeutic treatment is lower than that of an antisense oligonucleotide. A single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it may be that the specificity of action of a ribozyme is greater than that of antisense oligonucleotide binding the same RNA site.

Another class of catalytic molecules are called "DNAzymes". DNAzymes are single-stranded, and cleave both RNA and DNA. A general model for the DNAzyme has been proposed, and is known as the "10-23" model. DNAzymes following the "10-23" model, also referred to simply as "10-23 DNAzymes", have a catalytic domain of 15 deoxyribonucleotides, flanked by two substrate-recognition domains of seven to nine deoxyribonucleotides each. In vitro analyses show that this type of DNAzyme can effectively cleave its substrate RNA at purine:pyrimidine junctions under physiological conditions. As used herein, "DNAzyme" means a DNA molecule that specifically recognizes and cleaves a distinct target nucleic acid sequence, which may be either DNA or RNA.

Adapted Nucleic Acids

In another aspect of the invention, the antidote to the improved aptamers are Peptide Nucleic Acids (PNAs). PNAs are compounds that are analogous to oligonucleotides, but differ in composition in that the deoxyribose backbone of oligonucleotide is replaced by a peptide backbone. Each subunit of the peptide backbone is attached to a naturally-occurring or non-naturally-occurring nucleobase.

PNAs can be advantageous as fast acting antidotes because they bind more tightly to the corresponding improved aptamers than their non-substituted oligonucleotide counterparts. PNAs bind to both DNA and RNA and the resulting PNA/DNA or PNA/RNA duplexes are bound tighter than corresponding DNA/DNA or DNA/RNA duplexes as evidenced by their higher melting temperatures ($T_m$). Another advantage of PNA/DNA (RNA) duplexes is that $T_m$ is practically independent of salt concentration. Since PNAs are an analogue of DNA in which the backbone is a pseudopeptide rather than a sugar, they mimic the behaviour of DNA and binds complementary nucleic acid strands.

PNAs are synthetic polyamides comprised of repeating units of the amino acid, N-(2-aminoethyl)-glycine, to which the nucleobases adenine, cytosine, guanine, thymine and uracil are attached through a methylene carbonyl group. Natural and unnatural nucleobases, such as pseudo isocytosine, 5-methyl cytosine and 2,6-diaminopurine, inosine, uracil, 5-methylcytosine, thiouracil, 2,6-diaminopurine, bromothymine, azaadenines or azaguanines among many others, also can be incorporated in PNA synthons. PNAs are most commonly synthesized from monomers (PNA synthons) protected according to the t-Boc/benzyl protection strategy, wherein the backbone amino group of the growing polymer is protected with the t-butyloxycarbonyl (t-Boc) group and the exocyclic amino groups of the nucleobases, if present, are protected with the benzyloxycarbonyl(benzyl) group. PNA synthons protected using the t-Boc/benzyl strategy are now commercially available.

Morpholino nucleic acids (MNAs) can also be advantageous in antidote preparation because morpholinos are completely resistant to nucleases and they appear to be free of most or all of the non-antisense effects that plague S-DNAs. MNAs are assembled from morpholino subunits, each of which contains one of the four genetic bases (adenine, cytosine, guanine, and thymine) linked to a 6-membered morpholine ring. Subunits of are joined by non-ionic phosphorodiamidate intersubunit linkages to give a MNA. These MNAs can have substantially better antisense properties than do RNA, DNA, and their analogs having 5-membered ribose or deoxyribose backbone moieties joined by ionic linkages (see www.gene-tools.com/Morpholinos/body_morpholinos.HTML).

U.S. Pat. No. 6,153,737 to Manoharan et al. is directed to derivatized oligonucleotides wherein the linked nucleosides are functionalized with peptides, proteins, water soluble vitamins or lipid soluble vitamins. This disclosure was directed towards antisense therapeutics by modification of oligonucleotides with a peptide or protein sequence that aids in the selective entry of the complex into the nuclear envelope. Similarly, water-soluble and lipid-soluble vitamins can be used to assist in the transfer of the anti-sense therapeutic or diagnostic agent across cellular membranes.

Locked nucleic acids (LNAs) can also be used to prepare the antidotes of the present invention. LNAs are a novel class of DNA analogues that possess certain features that make them prime candidates for improving nucleic acid properties. The LNA monomers are bicyclic compounds structurally similar to RNA-monomers. LNAs share most of the chemical properties of DNA and RNA, are water-soluble, can be separated by gel electrophoreses, ethanol precipitated, etc. (Tetrahedron, 54, 3607-3630 (1998)). However, introduction of LNA monomers into either DNA or RNA oligos results in high thermal stability of duplexes with complementary DNA or RNA, while, at the same time obeying the Watson-Crick base-pairing rules. This high thermal stability of the duplexes formed with LNA oligomers together with the finding that primers containing 3' located LNA(s) are substrates for enzymatic extensions, e.g. the PCR reaction, makes these compounds suitable for the antidotes of the present invention. For examples of LNAs see U.S. Pat. No. 6,316,198.

In other embodiments, the stabilized nucleic acid can be a PCO (pseudocyclic oligonucleobase), or a 2'-O,4'-C-ethylene bridged nucleic acid (ENA).

6. Methods of Use

Regulating Coagulation with an Improved Aptamer

The invention includes the use of improved aptamers to bind to FIX, FIXa, or the intrinsic tenase complex. The binding can be ill vitro or in vivo. The result of the binding to FIX, FIXa or the tenase complex can be to inhibit the biological activity of the proteins or complex. The improved aptamers can be used to treat diseases such as deep venous thrombosis, arterial thrombosis, post surgical thrombosis, coronary artery bypass graft (CABG), percutaneous transdermal coronary angioplasty (PTCA), stroke, tumour metastasis, inflammation, septic chock, hypotension, ARDS, pulmonary embolism, disseminated intravascular coagulation (DIC), vascular restenosis, platelet deposition, myocardial infarction, angiogenesis, or the prophylactic treatment of mammals with atherosclerotic vessels at risk for thrombosis.

In one embodiment, the improved aptamer inhibits blood coagulation by binding to FIXa. The invention includes administering the aptamer of the invention to a mammal, for example, a human, in need thereof to inhibit blood coagulation. Another embodiment of the invention provides methods of using aptamers that are well suited for administration during a therapeutic regime.

A method of improved regulating coagulation in a mammal in need thereof is provided. In one embodiment, the method comprises: (a) administering to a warm-blooded vertebrate or mammal in need thereof, an effective amount of an improved aptamer that selectively binds coagulation pathway FIX, FIXa, or the intrinsic tenase complex, or inhibits a subunit of the intrinsic tenase complex (i.e. FIX, FIXa, FVIII binding to or activation of FX); (b) modulating the biological activity of the coagulation pathway factor in the warm-blooded vertebrate through the administering of the aptamer in step (a); and (c) providing an improved antidote to reverse the effects of the aptamer. In certain embodiments, the warm-blooded vertebrate or mammal is a human.

As used herein, the term "mammal" is meant to include any human or non-human mammal, including but not limited to porcine, ovine, bovine, rodents, ungulates, pigs, sheep, lambs, goats, cattle, deer, mules, horses, monkeys, dogs, cats, rats, and mice.

An important area for consideration is plasma half-life. Modifications can alter the half-life in vivo of the improved aptamers from a few minutes to 12 or more hours. The improved aptamers of the present invention can be used to treat percutaneous coronary interventions where vascular injury occurs at a specific time and place, yielding a sudden but relative brief prothrombotic stimulus. This may also be the case following carotid angioplasty. In another embodiment, the improved aptamers can be used in extracorporeal circulation utilized in coronary bypass grafting and hemodialysis. The latter condition is somewhat complex because of the inherent thrombogenicity of arteriovenous (AV) shunts. The aptamers of the invention also can be used to treat a venous thromboembolic disease, mechanical heart valve replacement, atrial fibrillation, and conceivably in either primary or secondary prevention of cardiovascular events among patients with prior events, an unfavorable risk profile, documented multibed vascular disease, vascular inflammation (early stages of atherosclerotic vasculopathy).

A method of treating cardiovascular disease in a warm-blooded vertebrate is also provided. The method comprises administering an effective amount of an improved aptamer to a vertebrate subject suffering from cardiovascular disease that selectively binds a coagulation pathway factor IX, IXa, or the intrinsic tenase complex, or inhibits a subunit of the intrinsic tenase complex (i.e. FIX, FIXa, FVIII binding to or activation of FX). Administration of the aptamer treats the cardiovascular disease in the vertebrate subject. The method can further comprise providing an antidote to reverse the effects of the improved aptamer by administration of an antidote.

The improved aptamers can be administered to mammals who require blood coagulation therapy. The invention provides methods of treating mammals with an aptamer to inhibit blood coagulation. The paired antidote can be administered to reverse the effects of the aptamer. A benefit of this discovery is that blood coagulation can be controlled in real time and does not rely on the mammal's own metabolism.

The compositions and methods of the present invention are particularly useful for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, CABG surgery and disseminated intravascular coagulation.

In addition, the improved aptamers and antidotes of the present invention can inhibit other cardiovascular disease associated with FIX or FIX-regulated cascades. Coagulation plays an important part in ischaemic cardiovascular disease. Results of studies have shown that extremes in hypocoagulability protect against ischaemic cardiovascular disease. A mild decrease in coagulability found in hemophiliac patients can have a protective effect against fatal ischaemic heart disease (Sramek A, et al. (2003) *Lancet* 362(9381):351-4; Bilora F, et al. (1999) *Clin Appl Thromb Hemost.* 5(4):232-5.

The aptamers can be administered to prevent coagulation-induced inflammation. Inflammation is induced by thrombolytic therapy in patients with acute myocardial infarction (AMI), which might contribute to microvascular obstruction and reperfusion injury. Improved aptamers of the present invention can inhibit this early inflammatory response. In one embodiment, methods are provided to reduce the early inflammatory response in mammals that are in need thereof by administering the improved aptamers of the present invention.

The improved aptamers and antidotes of the present invention can be used to inhibit atherosclerosis. Some adverse events in atherosclerosis are associated with ruptured plaques, which are a major cause of morbidity and mortality associated with atherosclerosis. In addition to conventional coronary heart disease risk factors, coagulation factor IX activation peptide and fibrinogen can be positively associated with risk of coronary heart disease (R. Rosenberg et al. (2001) *Thromb Haemost* 86: 41-50; J A Cooper et al. (2000) *Circulation* 102: 2816-2822). The intrinsic pathway may significantly enhance thrombogenicity of atherosclerotic lesions after removal of the endothelial layer and exposure of SMCs and macrophages to blood flow (Ananyeva N M et al. (2002) *Blood* 99: 44754485). In addition, the improved aptamers can also be provided to prevent morbidity in mammals suffering from acute coronary syndrome (ACS) associated with inflammation.

In certain clinical scenarios, the contact pathway becomes the major pathway for blood clotting. These include surgical procedures where the blood products are removed from the body, such as contact of the blood with the cardiopulmonary bypass (CPB) circuit and oxygenator induces an inflammatory state during and post CPB. Genetic epidemiology and prospective clinical studies have linked the magnitude of the inflammatory response during coronary revascularization procedures with multiple adverse effects of CPB, including renal damage, atrial fibrillation, stroke, gut damage and neuronal damage. The inflammatory response induced by activation of the coagulation pathway is mediated by coagulation factors Xa and thrombin, which in addition to their role in blood clot formation, are themselves proinflammatory and mitogenic signaling proteins. The improved aptamers can also be administered to prevent adverse effects associated with post-angioplasty restenosis.

Regulating Coagulation with Improved Aptamer-Antidote Pairs

Among the many challenges of treating patients with thrombotic disorders or during a coagulation-inducing event is the potential risk of hemorrhage associated with anticoagulant drug therapy. The mechanisms which underlie bleeding risk are complex, but are unquestionably a function of drug variability (excess anticoagulant effect for the degree of thrombogenicity or extent of thrombus burden), relatively poor correlation between drug concentration and anticoagulant effect, wide-spread compromise of hemostatic barriers (platelet performance, vascular integrity, multiple phases of coagulation) and limited control of the anticoagulant's behavior.

At least three clinical scenarios exist in which the ability to rapidly reverse the activity of an antithrombotic or anticoagulant nucleic acid ligand is desirable. The first case is when anticoagulant or antithrombotic treatment leads to hemorrhage, including intracranial or gastrointestinal hemorrhage. While identifying safer target proteins may reduce this risk, the potential for morbidity or mortality from this type of bleeding event is such that the risk can not be overlooked. The second case is when emergency surgery is required for patients who have received antithrombotic treatment. This clinical situation arises in a percentage of patients who require emergency coronary artery bypass grafts (CABG) while undergoing percutaneous coronary intervention under the coverage of GPIIb/IIIa inhibitors. Current practice in this situation is to allow for clearance of the compound (for small molecule antagonists such as eptifibatide), which may take 2-4 hours, or platelet infusion (for Abciximab treatment). The third case is when an anticoagulant nucleic acid ligand is used during a cardiopulmonary bypass procedure. Bypass patients are predisposed to post operative bleeding. In each case, acute reversal of the anticoagulant effects of a compound via an antidote (e.g., an oligonucleotide antidote of the invention targeted to an anticoagulant or antithrombotic nucleic acid ligand) allows for improved, and likely safer, medical control of the anticoagulant or antithrombotic compound.

The applicants have discovered improved aptamer-antidote pairs that precisely regulate proteins in the blood coagulation cascade. In one embodiment, the antidotes of the invention are provided to a mammal in need thereof after the aptamers of the invention to reverse the effects of the aptamers. Aptamers and aptamer-antidote pairs can be administered in real time as needed based on various factors, including the progress of the patient, as well as the physician's discretion in how to achieve optimal therapy. Thus, this invention discloses an improved regulatable therapeutic regime in the course of nucleic acid ligand therapy for blood coagulation.

Individuals who are undergoing surgery also require the targeted modulation of coagulation that occurs through the use of the improved aptamers and antidotes of the present invention. In certain embodiments, the aptamers are administered to patients undergoing general surgery. In certain other embodiments, the aptamers are administered to patients with cardiovascular disease, which can include coronary heart disease. The patients can be undergoing treatment including bypass surgery or percutaneous coronary interventions. The mammals who can be treated with the aptamers of the present invention can also include patients who have had physical trauma that requires coagulation therapy.

Preoperative assessment of the patient can identify drug-induced, acquired, or inherited coagulation defects. The main attention in anticoagulant therapy is directed to the perioperative period. A further, often overlooked, management strategy in treating major coagulopathies is the consideration of the cost and half-lives of the coagulation factors in individual blood components. Prevention of bleeding has become possible by manipulation of the control of coagulation and inflammatory processes. Additionally, because diagnosis of patients is often difficult, the modulatable improved aptamers and antidote pairs of the present invention are particularly useful in ensuring that, in case of incorrect diagnosis and treatment, treatment can immediately be disabled. For example, the symptoms of coronary infarction can closely mimic those of an acute coronary dissection. See Scarabeo et al. (2002) *Italian Heart Journal* 3: 490-494. A diagnosis of coronary infarction immediately calls for an anticoagulant, which is counterindicated in acute coronary dissection. With the improved aptamer-antidote pairs described herein, a mistake by a health care provider can readily be reversed.

Agents that restore vascular patency in stroke also increase the risk of intracerebral hemorrhage (ICH). As Factor IXa is a key intermediary in the intrinsic pathway of coagulation, targeted inhibition of Factor IXa-dependent coagulation can inhibit microvascular thrombosis in stroke without impairing extrinsic hemostatic mechanisms that limit ICH. The improved aptamers and antidotes of the present invention can be used to inhibit stroke associated with cardiovascular disease and surgery.

Administration

The present method for treating cardiovascular disease in a tissue contemplates contacting a tissue in which cardiovascular disease is occurring, or is at risk for occurring, with a composition comprising a therapeutically effective amount of an improved aptamer capable of binding a coagulation factor as well as providing an improved antidote to reverse the effects of the aptamer by administration of an antidote. Thus, the method comprises administering to a patient a therapeutically effective amount of a physiologically tolerable composition containing the RNA aptamer as well as a method to provide an antidote to reverse the effects of the aptamer by administration of an antidote.

The dosage ranges for the administration of the antidote depend upon the form of the antidote, and can be assessed by a physician or other health care provider. Generally, the dosage will vary with the age, condition, sex and extent of the disease in the patient and can be determined by one of skill in the art. The individual physician in the event of any complication can also adjust the dosage.

Generally, a therapeutically effective amount is an amount of a antidote sufficient to produce a measurable modulation of the effects of the nucleic acid ligand, including but not limited to a coagulation-modulating amount or an inflammation-modulating amount.

Preferred modes of administration of the improved aptamers of the present invention are parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump or via catheter. In one embodiment, the agent and carrier are administered in a slow release formulation such as an implant, bolus, microparticle, microsphere, nanoparticle or nanosphere.

The antidotes of the present invention can be preferably administered parenterally by injection or by gradual infusion over time. Although the tissue to be treated can typically be accessed in the body by systemic administration and therefore most often treated by intravenous administration of therapeutic compositions, other tissues and delivery techniques are provided where there is a likelihood that the tissue targeted contains the target molecule. Thus, antidotes of the present invention are typically administered orally, topically to a vascular tissue, intravenously, intraperitoneally, intramuscularly, subcutaneously, intra-cavity, transdermally, and can be delivered by peristaltic techniques. As noted above, the pharmaceutical compositions can be provided to the individual by a variety of routes such orally, topically to a vascular tissue, intravenously, intraperitoneally, intramuscularly, subcutaneously, intra-cavity, transdermally, and can be delivered by peristaltic techniques. Representative, non-liming approaches for topical administration to a vascular tissue include (1) coating or impregnating a blood vessel tissue with a gel comprising a nucleic acid ligand, for delivery in vivo, e.g. by implanting the coated or impregnated vessel in place of a damaged or diseased vessel tissue segment that was removed or by-passed; (2) delivery via a catheter to a vessel in which delivery is desired; (3) pumping a nucleic acid ligand composition into a vessel that is to be implanted into a patient. Alternatively, the nucleic acid ligand can be introduced into cells by microinjection, or by liposome encapsulation. Advantageously, nucleic acid ligands of the present invention can be administered in a single daily dose, or the total daily dosage can be administered in several divided doses. Thereafter, the antidote is provided by any suitable means to alter the effect of the nucleic acid ligand by administration of the antidote.

Compositions

The aptamers and antidotes of the invention can be formulated into pharmaceutical compositions that can include, in addition to an improved aptamer, a antidote or modulator, and a pharmaceutically acceptable carrier, diluent or excipient. The precise nature of the composition will depend, at least in part, on the nature of the improved aptamer and antidote and the route of administration. Optimum dosing regimens can be readily established by one skilled in the art and can vary with the improved aptamer, the antidote combination, the patient and the effect sought.

For standard information on pharmaceutical formulations, see Ansel, et al., Pharmaceutical Dosage Forms and Drug Delivery Systems, Sixth Edition, Williams & Wilkins, 1995. The therapeutic compositions comprising aptamers and antidotes of the present invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e. carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Pharmaceutically useful compositions comprising an aptamer or antidote of the present invention can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the aptamer. Such compositions can contain admixtures of more than one aptamers or antidotes.

The effective amount of an improved aptamer of the invention can vary according to a variety of factors such as the individual's condition, weight, sex and age. Other factors include the mode of administration. Generally, the compositions will be administered in dosages adjusted for body weight, e.g., dosages ranging from about 0.1 mg/kg body weight to about 100 mg/kg body weight. In specific embodiments, the dosages are about 0.5 mg/kg body weight to 50 mg/kg body weight. In specific embodiments, the dosage is between 0.1, 0.2, 0.3, 0.4, 0.5, 0.6, 0.7, 0.8, 0.9, and 1 mg/kg body weight, and any dosage in between. Specific dosage units can range from 1 ng to 1 g, but are more conventionally about 0.01 µg, 0.1 µg, 1 µg, 10 µg, 100 µg, 500 µg, or 1 g or any amount in between.

The effective amount of antibody being delivered to a patient will vary according to a variety of factors such as the individual's condition, weight, sex, age and amount of nucleic acid ligand administered. In one embodiment, the antidote ranges from 0.5-50 mg/kg. In another embodiment, the amount of antidote being delivered ranges from 0.5-10, 0.5-5, 1-10 or 1-5 mg/kg. In general, the amount of antidote being delivered is not less than the amount of aptamer being delivered. Typically, the amount of antidote is from about 1 to about 20 times the amount of aptamer. In certain embodiments, the antidote is about 1, 2, 3, 4, 5, 6, 7, 8, 9, or 10 times the amount of aptamer delivered to a patient.

Improved combinations of aptamers and antidotes in pharmaceutical compositions are administered in therapeutically effective amounts, that is, in amounts sufficient to generate a coagulation-modulating response, or in a prophylactically effective amounts, that is in amounts sufficient to prevent a coagulation factor from acting in a coagulation cascade. The therapeutically effective amount and prophylactically effective amount can vary according to the modulator. The pharmaceutical composition can be administered in single or multiple doses.

Because the activity of the improved antidotes is lasting, once the desired level of modulation of the nucleic acid ligand by the antidote is achieved, infusion of the antidote can be terminated, allowing residual antidote to clear the human or animal. This allows for subsequent re-treatment with the nucleic acid ligand as needed. Alternatively; and in view of the specificity of the antidotes of the invention, subsequent treatment can involve the use of a second, different improved aptamer/antidote pair.

Antidotes synthesized or identified according to the methods disclosed herein can be used alone at appropriate dosages defined by routine testing in order to obtain optimal modulation of nucleic acid ligand activity in coagulation, while minimizing any potential toxicity. In addition, co-administration or sequential administration of other agents can be desirable. For combination treatment with more than one active agent, where the active agents are in separate dosage formulations, the active agents can be administered concurrently, or they each can be administered at separately staggered times.

The dosage regimen utilizing the improved aptamers and antidotes of the present invention is selected in accordance with a variety of factors including type, species, age, weight, sex and medical condition of the patient; the severity of the condition to be treated; the route of administration; the renal and hepatic function of the patient; and the particular combination employed. A physician of ordinary skill can readily determine and prescribe the effective amount of the aptamer required to prevent, counter or arrest the progress of the condition. Optimal precision in achieving concentrations of the combination within the range that yields efficacy without toxicity requires a regimen based on the kinetics of the aptamer and antidote's availability to target sites. This involves a consideration of the distribution, equilibrium, and elimination of the modulator.

In the methods of the present invention, the combinations described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that can be employed include glycerin and the like. For parenteral administration, sterile suspensions and solutions are desired. Isotonic preparations that generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 mydstyl propionate, and the like, to form, e.g. alcoholic solutions, topical cleansers, cleansing creams, skin gels, skin lotions, and shampoos in cream or gel formulations.

The aptamers and antidotes of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The aptamers and antidotes of the present invention can also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyleneoxidepolylysine substituted with palmitoyl residues. Furthermore, the aptamers and antidotes of the present invention can be coupled (preferably via a covalent linkage) to a class of biodegradable polymers useful in achieving controlled release of a drug, for example, polyethylene glycol (PEG), polylactic acid, polyepsilon caprolactone, polyhydroxy butyric acid, polyorthoesters, polyacetals, polydihydro-pyrans, polycyanoacrylates and cross-linked or amphipathic block copolymers of hydrogels. Cholesterol and similar molecules can be linked to the aptamers to increase and prolong bioavailability.

In certain embodiments of this invention, the complex comprises a liposome with a targeting nucleic acid ligand (s) associated with the surface of the liposome and an encapsulated therapeutic or diagnostic agent. Preformed liposomes can be modified to associate with the nucleic acid ligands. For example, a cationic liposome associates through electrostatic interactions with the nucleic acid. Alternatively, a nucleic acid attached to a lipophilic compound, such as cholesterol, can be added to preformed liposomes whereby the cholesterol becomes associated with the liposomal membrane. Alternatively, the nucleic acid can be associated with the liposome during the formulation of the liposome. Preferably, the nucleic acid is associated with the liposome by loading into preformed liposomes.

Certain aspects of the invention can be described in greater detail in the non-limiting Examples that follow.

EXAMPLES

Tests of Aptamers for Coagulation

The following tests are used to assess the capacity of modified aptamers and antidotes to inhibit coagulation factors.

The Activated Clotting Time Test (ACT) is a screening test that resembles the activated partial thromboplastin time (APTT) test, but is performed using fresh whole blood samples. ACT can be to monitor a patient's coagulation status in connection with clinical procedures, such as those that involve the administration of high doses of heparin (e.g., CPB and PTCA).

The Activated Partial Thromboplastin Time Test (APTT) is a common central laboratory test, typically performed using an automated coagulometer, for example Diagnostica Stago's STA coagulometer (MDA/96/23), or another coagulometer produced by this company or otherwise known in the art, The test is performed using a plasma sample, in which the intrinsic pathway is activated by the addition of phospholipid, an activator (ellagic acid, kaolin, or micronized silica), and $Ca^{2+}$.

The bleeding time test can be used for the diagnosis of hemostatic dysfunction, von Willebrand's disease, and vascular disorders. It also can be used to screen for platelet abnormalities prior to surgery. The test is performed by making a small incision on the forearm and wicking away the blood from the wound site. The time it takes for bleeding to stop is recorded and in control subjects is approximately 3.5 minutes. Prolongation of the bleeding time is indicative of qualitative or quantitative platelet defects.

The Prothrombin Time Test (PT), which was first described by Quick in 1935, measures the tissue factor-induced coagulation time of blood or plasma. It is used as a screening test to evaluate the integrity of the extrinsic coagulation pathway, and is sensitive to coagulation factors I, II, V, VII, and X. The test can be performed by adding thromboplastin and $Ca^{2+}$ to a patient sample and measuring the time for clot formation. A prolonged clotting time suggests the presence of an inhibitor to, or a deficiency in, one or more of the coagulation factors of the extrinsic pathway. But PT clotting time can also be prolonged for patients on warfarin therapy, or for those with vitamin K deficiency or liver dysfunction. The PT test can provide an assessment of the extrinsic coagulation pathway, and is widely used to monitor oral anticoagulation therapy.

The Thrombin Clotting Time Test (TCT) measures the rate of a patient's clot formation compared to that of a normal plasma control. The test can be performed by adding a standard amount of thrombin to a patient's plasma that has been depleted of platelets, and measuring the time required for a clot to form. This test has been used as an aid in the diagnosis of disseminated intravascular coagulation (DIC) and liver disease.

There are also a number of tests that may be used in the diagnosis of a patient's coagulative status. These fall into two categories: complex tests, some of which are based on the screening tests outlined above, and immunoassays. Complex Tests include specific factor assays based on laboratory tests, such as the APTT, PT, and TCT tests. One assay measures the level of the activation Factor IXa or the Factor IXa-antithrombin III complex. These measurements are used to determine the levels of factor IXa or factor VII-tissue mediated complex. Assays for activated protein C resistance, antithrombin, protein C deficiency, and protein S deficiency are also part of this group. Asymptomatic individuals who have heterogeneous deficiencies of proteins C and S, and resistance to activated protein C, have significantly elevated levels of the prothrombin fragment F1.2 compared to controls.

Example 1

Substitution of 2'-O-methyl for 2'-hydroxyl sugars in sectors

2'-Hydroxyl purines were substituted with 2'-O-methyl purines in the 4 secondary structure units of in which purine residues are present: Stem 1 (Apt 1); Loop 1 (Apt 2); Stem 2 (Apt 3); Loop 2 (Apt 4) (see FIG. 1A).

Procedure: The anticoagulant activity of AptA derivatives Apt 1-5 was evaluated in standard APTT coagulation assays over compound concentrations ranging from 1 uM to low nanomolar (FIG. 2). The "neutralizability" of Apt1-5 was evaluated in standard APTT antidote assays over AptA antidote concentrations (AptA AD; see sequence listings) ranging from 5 uM and down (FIG. 2). For these assays, the concentration of AptA and derivatives was fixed at 125 nM.

Apt 4 showed gain of anticoagulant activity (FIG. 2); Apt 1-3 showed moderate loss of activity; and Apt 5 showed severe loss of activity. Apt 1-3 exhibit enhanced neutralization, suggesting that introduction of 2'-O-methyl residues within the antidote binding site improves the ability of the antidote oligonucleotide to bind to the aptamer.

Sequence Listings:

| # | Name | Length | (5'-3') sequence |
|---|------|--------|------------------|
| 1) | AptA | Length: 35 | (5'-3') sequence: AUGGGGA CUAUACC GCG UAAUGC UGC C UCCCCAU T (SEQ ID NO:20) |
| 1) | Apt 1 | Length: 35 | (5'-3') sequence: aUgggga CUAUACCGCGUAAUGCUGCC UCCCCaU T (SEQ ID NO: 21) |
| 3) | Apt 2 | Length: 35 | (5'-3') sequence: AUGGGGA CUaUaCC GCG UAAUGC UGC C UCCCCAU T (SEQ ID NO:22) |
| 4) | Apt 3 | Length: 35 | (5'-3') sequence: AUGGGGA CUAUACC gCg UAAUGC UgC C UCCCCAU T (SEQ ID NO:23) |
| 5) | Apt 4 | Length: 35 | (5'-3') sequence: AUGGGGA CUAUACC GCG UaaUgC UGC C UCCCCAU T (SEQ ID NO:24) |
| 6) | Apt 5 | Length: 35 | (5'-3') sequence: aUgggga CUaUaCC gCg UaaUgC UgC C UCCCCaU T (SEQ ID NO:25) |
| 7) | AptA AD | Length: 17 | (5'-3') sequence: cgcgguaua gucccau (SEQ ID NO:1) |

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine.

| # | Name | Length | (5'-3') |
|---|------|--------|---------|
| 1) | Apt 6 | Length: 29 | (5'-3'): ggga CUaUaCCGCGUAA UGCUGCC uccc T (SEQ ID NO:26) |
| 2) | Apt 7 | Length: 31 | (5'-3'): gugga CUaUaCCGCGUA AUGCUGCC uccac T (SEQ ID NO:27) |
| 3) | Apt 8 | Length: 33 | (5'-3'): gaugga CUaUaCCGCGU AAUGCUGCC uccauc T (SEQ ID NO:28) |
| 4) | Apt 9 | Length: 29 | (5'-3'): cuga CUaUaCCGCGUAA UGCUGCC ucag T (SEQ ID NO:29) |
| 5) | Apt 10 | Length: 31 | (5'-3'): ccuga CUaUaCCGCGUA AUGCUGCC ucagg T (SEQ ID NO:30) |
| 6) | Apt 11 | Length: 33 | (5'-3'): cucuga CUaUaCCGCGU AAUGCUGCC ucagag T (SEQ ID NO:31) |
| 7) | Apt 6 AD | Length: 14 | (5'-3'): cgcgguauaguccc (SEQ ID NO:2) |
| 8) | Apt 7 AD | Length: 15 | (5'-3'): cgcgguauaguccac (SEQ ID NO:3) |
| 9) | Apt 8 AD | Length: 16 | (5'-3'): cgcgguauaguccauc (SEQ ID NO:4) |
| 10) | Apt 9 AD | Length: 14 | (5'-3'): cgcgguauagucag (SEQ ID NO:5) |
| 11) | Apt 10 AD | Length: 15 | (5'-3'): cgcgguauagucagg (SEQ ID NO: 6) |
| 12) | Apt 11 AD | Length: 16 | (5'-3'): cgcgguauagucagag (SEQ ID NO:7) |

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine.

Example 2

Stem 1 Modifications

Two "families" of stem 1 variants were designed (Apt 6-8 and 9-11; FIG. 1B) consisting of 4, 5, and 6 basepair stems. All constructs were designed in the Apt-2 background. Stem 1 sequences were evaluated for the ability to design complementary antidote oligonucleotides to them such that the antidotes contain minimal secondary structure, and for the ability of the aptamer to assume the proper secondary structure.

Stems were wholly 2'-O-methyl modified. Antidote oligonucleotides were designed specific for Apt 6-11 that bind to their respective target aptamer in the same register as AptA AD (see sequence listings below).

Experiments: The anticoagulant activity of Apt 6-11 was evaluated in standard APTT coagulation assays over compound concentrations ranging from 1 uM to low nanomolar. The antidote control of Apt 6-11 was evaluated in standard APTT antidote assays over antidote concentrations ranging from 5 uM and down. For these assays, the concentration of Apt 2, and Apt 6-11 was set at 250 nM (as opposed to 125 nM for standard AptA and Apt 2 experiments).

Apt 6-8 exhibit loss of anticoagulant activity (FIG. 3), however, all exhibit similar activity levels. Thus stem length is not be the main cause for loss of activity. The 5 base pair stem 1 constructs (Apt 10 and Apt 7) do appear to be more neutralizable than Apt 2 (FIGS. 3 and 4). Data suggests that a stem 1 of 5 base pairs may be preferable to those composed of 4, 6 or 7 base pairs to enhance antidote neutralization.

Example 3

Stem 1 Sugar Chemistry

The anticoagulant activity of Apt 12-17 was evaluated in standard APTT coagulation assays over compound concentrations ranging from 1 uM to low nanomolar. The "neutralizability" of Apt 12-17 was evaluated in standard APTT antidote assays over antidote concentrations ranging from 5 uM and down. For Apt 12, 14, 15, and 16, the aptamer concentration was fixed at 125 nM in these assays, and for Apt 13 and 17, the aptamer concentration was fixed at 250 nM.

Comparison of the anticoagulant activity of Apt 12 with Apt 13 and Apt17 (FIG. 5) demonstrates that the loss of activity observed for Apt6-11 is due to the presence of 2'-O-methyl substitutions at one or more critical residues. Comparison of the anticoagulant activity of Apt14 to Apt12 indicates that the stretch of 4 consecutive guanosines within stem 1 can be altered without a significant impact on anticoagulant activity. Comparison of Apt15 and 16 with Apt 2, 12 and 17 a) demonstrates that the presence of 2'-O-methyl sugars at each position within stem 1 except for the closing A-U pair at the top of stem 1 enhances activity; b) demonstrates that the sugar of the U in this base pair must be 2'fluoro for the aptamer to retain potency; and c) suggests that the sugar of the A in this base pair can be a 2'-O-methyl sugar without a significant impact on anticoagulant activity. In fact, Apt 16 retains essentially full potency.

Comparison of the neutralization of Apt14-16 with Apt14/AD suggests that the antidote can more readily bind the aptamer when stem 1 is a 2'-O-methyl-2'fluoro stem as opposed to when both strands of the duplex contain largely 2'-O-methyl residues. Apt21 was designed in which the sugar of the A at the stop of stem 1 is 2'-O-methyl substituted (FIG. 1). Substitution of a 2'-O-methyl sugar at this adenosine residue is well tolerated in the background of a largely 2'-O-methyl stem (FIG. 6). Antidote neutralization of Apt 21 is enhanced as compared to Apt16 (see especially the 2.5:1 and 5:1 AD:Drug data points in FIG. 4).

Sequence Listings:

```
1) Apt2      Length: 35   (5'-3') sequence: aUgggga
                          CUaUaCCGCGUAAUGCUGCC UCCCC
                          aU T
                          (SEQ ID NO:32)

2) Apt13     Length: 35   (5'-3') sequence: augggga
                          CUaUaCCGCGUAAUGCUGCC uccccc
                          au T
                          (SEQ ID NO:33)

3) Apt14     Length: 35   (5'-3') sequence: gUgagga
                          CUaUaCCGCGUAAUGCUGCC UCCUC
                          aC T
                          (SEQ ID NO:34)

4) Apt15     Length: 35   (5'-3') sequence: gUgaggA
                          CUaUaCCGCGUAAUGCUGCC UCCUC
                          aC T
                          (SEQ ID NO:35)

5) Apt16     Length: 35   (5'-3') sequence: gugaggA
                          CUaUaCCGCGUAAUGCUGCC Uccuc
                          ac T
                          (SEQ ID NO:36)

6) Apt17     Length: 35   (5'-3') sequence: gugagga
                          CUaUaCCGCGUAAUGCUGCC uccuc
                          ac T
                          (SEQ ID NO:37)

7) Apt14AD   Length: 17   (5'-3') sequence: cgcgguaua
                          guccucac
                          (SEQ ID NO:8)

8) Apt21     Length: 35   (5'-3') sequence: gugagga C
                          UaUaCC GCG UAAUGC UGC C
                          Uccucac T
                          (SEQ ID NO:41)
```

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluro-Uridine; "u": 2'-O-methyl Uridine; "T": inverted 2'H Thymidine.

Example 4

Reducing Length of Stem 1

The anticoagulant activity of Apt 18-20 was evaluated in standard APTT coagulation assays over compound concentrations ranging from 1 uM to low nanomolar. The "neutralizability" of Apt 18-20 was evaluated in standard APTT antidote assays over antidote concentrations (Antidote 6, 7 and 8 for 18-20 respectively) ranging from 5 uM and down. The aptamer concentration was fixed at 125 nM in these assays.

Figure 8:
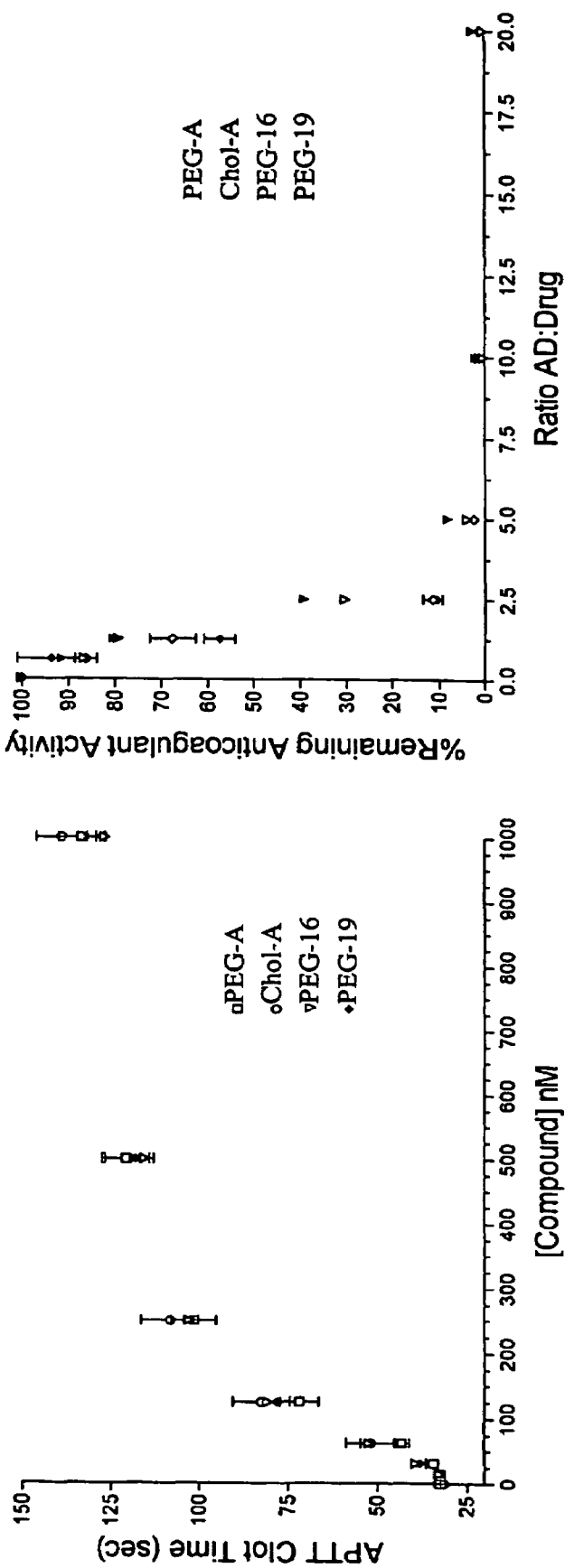
FIG. 8 is a graph of results of activated partial thromboplastin time (APTT) test assays of pegylated AptA compared to pegylated Apt 16 and 19 and cholesterol-modified Apt A (chol-A). Left panel is aptamer control of coagulation factor IX and right panel is neutralizability by antidote.

Each of the aptamers (Apt 18-20) is a potent anticoagulant, as or more potent than Apt 2 (FIG. 7). Furthermore, all three are readily neutralized by their respective antidote oligonucleotides. Apt 19 was evaluated for anticoagulant activity of a pegylated version. PEG Apt 19 and, for comparison, PEG-Apt 16 are used (PEG is a 40 KDa bifunctional polyethylene glycol mPEG2-NHS ester (MW 40 KDa; Nektar/Shearwater 2Z3XOT01, which includes two 20 KD monomethoxy PEGs bound together through a lysine and linked via a 6-carbon linker to a 5'-terminal phosphate on the aptamer), appended to the 5'end via conjugation to a C6 amino linker added to the aptamer during solid phase synthesis). FIG. 8 indicates that the length of stem 1 does not affect how 40 KDa PEG addition impacts the activity of AptA and AptA derivatives. The anticoagulant activity of PEG Apt 19 and 16 is essentially identical to the anticoagulant activity of both pegylated (PEG AptA) and cholesterol-modified (CH-AptA) versions of the parental AptA sequence. In addition, like Apt 19, PEG Apt 19 is more readily neutralized by its matched antidote (7 AD) than AptA, Apt 16 or any of the PEG or cholesterol-modified versions of these compounds. FIG. 8 shows approximately 90% reversal of PEG Apt 19 at 2.5:1 AD:Aptamer. Looked at as an absolute change in APTT rather than on a % reversal basis, the APTT of plasma treated with PEG Apt 19+2.5:1 7AD:Aptamer is only 4-5 seconds above baseline.

Sequence Listings:

```
1) Apt18      Length: 29   (5'-3') sequence: gggA CUaU
                           aCCGCGUAAUGCUGCC Uccc T
                           (SEQ ID NO:38)

2) Apt19      Length: 31   (5'-3') sequence: guggA
                           CUaUaCCGCGUAAUGCUGCC Uccac
                           T
                           (SEQ ID NO:39)

3) Apt20      Length: 33   (5'-3') sequence: gauggA
                           CUaUaCCGCGUAAUGCUGCC Uccauc
                           T
                           (SEQ ID NO:40)

4) PEG Apt    Length: 35   (5'-3') sequence: P-L-gugag
   16                      gA CUaUaCCGCGUAAUGCUGCC
                           Uccucac T 5) PEG Apt    Length: 31   (5'-3') sequence: P-L-guggA
   19                      CUaUaCCGCGUAAUGCUGCC Uccac
                           T
```

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine; "P": mPEG2-NHS ester MW 40 KDa (Nektar/Shearwater 2Z3XOT01); "L": C6 amino linker Example 5

Stem 2 and Loop 2 Substitutions

Two series of variants evaluating the optimal sugar composition for the residues in stem 2 and loop 2. The first series in the Apt 16 background. The second series in the Apt 16 background, but substituting the tetraloop found in FIXa aptamer 9.20 (see Rusconi et al Nature 419, p. 90-94, 2002 and FIG. 1) for the hexanucleotide loop found in AptA. Studies on Apt 4 indicated that 2'-O-methyl purine substitution within loop 2 led to an enhancement in AptA potency, whereas 2'-O-methyl purine substitution within stem 2 led to a modest loss of potency, and that simultaneous 2'-O-methyl purine substitution within stem 2 and loop 2 in the context of a 2'-O-methyl purine stem 1 led to a significant loss of AptA potency (Apt 5). Therefore, independently substitute 2'-O-methyl purines in stem 2 (Apt 22, 26) and loop 2 (Apt 23, 27) (FIG. 9). Re-evaluated complete 2'-O-methyl substitution of purines within stem 2 and loop 2 (Apt 24, Apt 28) but leave the G at the base of stem 2 as a 2'hydroxyl (Apt 25, 29) in the event that a 2'hydroxyl is required at this position.

The anticoagulant activity of Apt 22-29 was evaluated in standard APTT coagulation assays over compound concentrations ranging from 1 uM to low nanomolar. The "neutralizability" of Apt 22-29 was evaluated in standard APTT antidote assays over antidote concentrations ranging from 5 uM and down. The aptamer concentration was fixed at 125 nM in these assays, except for Apt 24 in which the aptamer concentration was fixed at 250 nM.

Figure 14A:
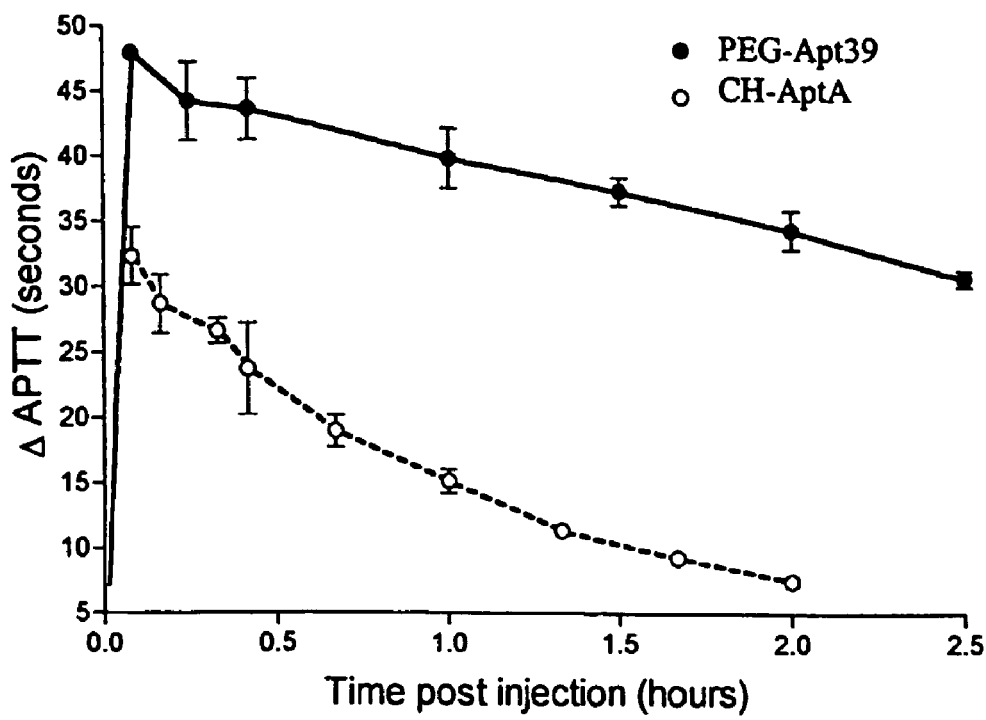
FIG. 14 are graphs of systemic anticoagulant activity (14a) and neutralizability (14b) of PEG-Apt39 in swine. The change in the value of the respective clotting assays is the difference between the clotting time at the time point and the pre-injection baseline for that animal. n=2 for PEG-Apt39 treated animals and n=3 for CH-AptA treated animals. Whole blood ACT values are shown in the bottom panel, and plasma APTT values in the panel at the top.
Figure 14A:
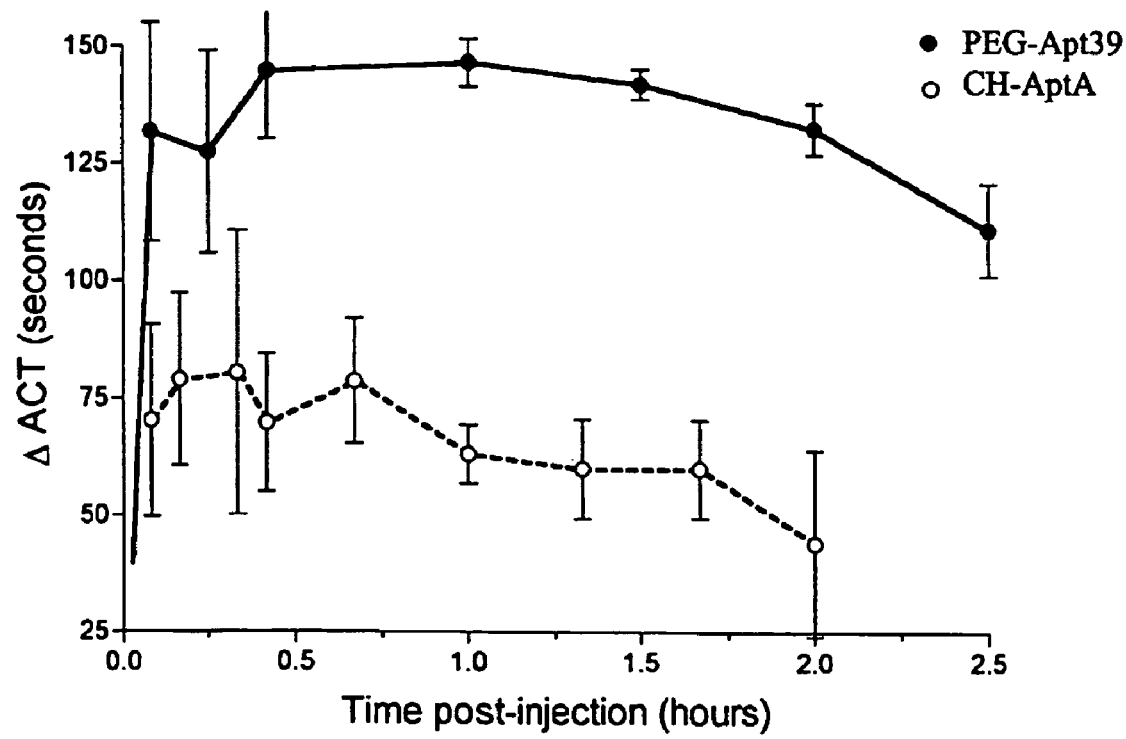

As previously observed with Apt 3, substitution of 2'-O-methyl purines within loop 2 leads to enhanced potency (Apt 23, compare Apt 23 to 16) (FIG. 9). Likewise, substitution of 2'-O-methyl purines into stem 2 leads to a moderate loss of activity (Apt 22, 24) (FIG. 14). Apt 24 is significantly more potent than Apt 5. Maintenance of a 2'hydroxyl on the G residue at the base of stem 2 (Apt 25) does not lead to enhanced activity as compared to Apt 24, indicating that a) substitution of a 2'-O-methyl sugar at this residue is not the problem within Apt 22 and 24 and b) the sugar on this residue can be 2'-O-methyl. Substitution of the 9.20 tetraloop for the hexanucleotide loop present in AptA led to a loss of activity (Apt 26-29). Antidote neutralization of Apt 23 is reduced as compared to Apt 16, but still equivalent to AptA.

Sequence Listings:

1) Apt 22 Length: 35 (5'-3') sequence: gugaggA CUaUa CC gCg UAAUGC UgC C Uccucac T (SEQ ID NO:42)

2) Apt 23 Length: 35 (5'-3') sequence: gugaggA CUaUa CC GCG UaaUgC UGC C Uccucac T (SEQ ID NO:43)

3) Apt 24 Length: 35 (5'-3') sequence: gugaggA CUaUa CC gCg UaaUgC UgC C Uccucac T (SEQ ID NO:44)

4) Apt 25 Length: 35 (5'-3') sequence: gugaggA CUaUa CC GCg UaaUgC UgC C Uccucac T (SEQ ID NO: 45)

5) Apt 26 Length: 33 (5'-3') sequence: gugaggA CUaUa CC gCa AUCG UgC C Uccucac T (SEQ ID NO:46)

6) Apt 27 Length: 33 (5'-3') sequence: gugaggA CUaUa CC GCA aUCg UGC C Uccucac T (SEQ ID NO:47)

7) Apt 28 Length: 33 (5'-3') sequence: gugaggA CUaUa CC gCa aUCg UgC C Uccucac T (SEQ ID NO:48)

8) Apt 29 Length: 33 (5'-3') sequence: gugaggA CUaUa CC GCa aUCg UgC C Uccucac T (SEQ ID NO: 49)

Example 6

Stem 2 Sugar Chemistry

The anticoagulant activity of Apt 30-33 was evaluated in standard APTT coagulation assays over compound concentrations ranging from 1 uM to low nanomolar. The "neutralizability" of Apt 30 and 33 was evaluated in standard APTT antidote assays over antidote concentrations (Apt 14 AD) ranging from 5 uM and down. The aptamer concentration was fixed at 125 nM in these assays (see FIG. 10).

Figure 10A:
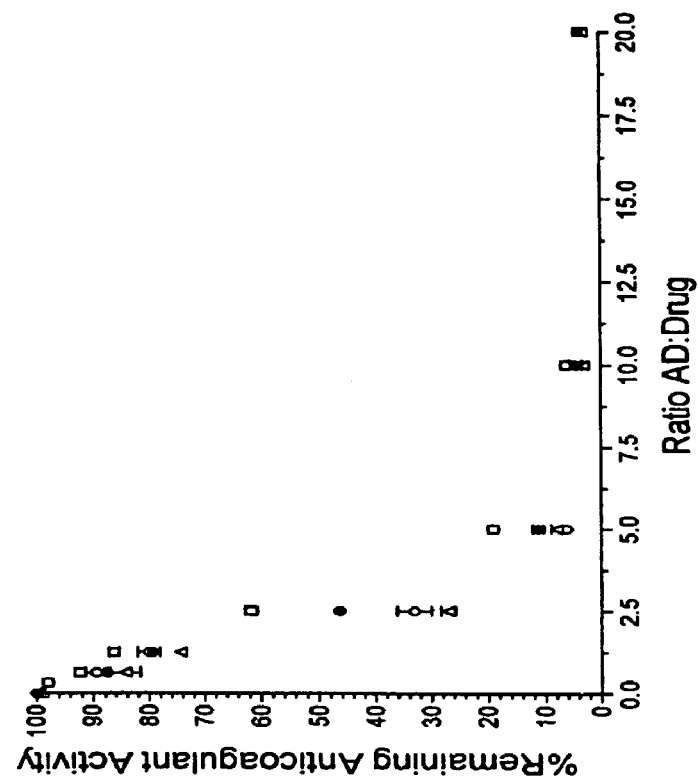
FIG. 10 is a graph of results of activated partial thromboplastin time (APTT) test assays of aptamers Apt 2 and 30-33 (A, left panel), neutralizability by antidote of Apt 2, 30 and 33 (A, right panel), APTT test assays of aptamers Apt 2, 30, 33 and 34 (B, left panel) and neutralizability by antidote (B, right panel).
Figure 10A:
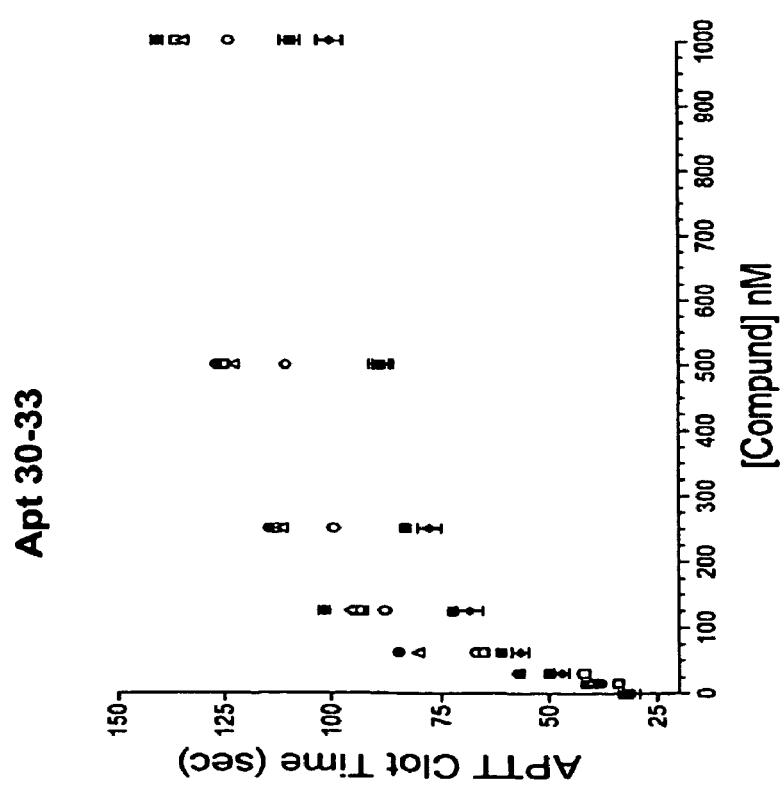

Comparison of the activity of Apt 30 and 33 to Apt 31 and 32 demonstrates that C16 needs to contain a 2'fluoro sugar and G25 a 2'hydroxyl sugar (FIG. 10a). Activity observed between Apt 31 and 32 suggests that remaining positions within stem 2 can contain 2'-O-methyl sugars. In fact, Apt 31 appears to possess slightly greater potency than Apt 32, indicating that a compound with 2'fluoro at C16, 2'hydroxyl at G25, and the remaining residues 2'-O-methyl may exhibit greater potency than Apt 33. Regardless, Apt 33 exhibits greater activity than Apt 2 and is fairly equivalent to original AptA. Apt 33 is more readily neutralizable than Apt 30, suggesting additional 2'-O-methyl residue within the antidote-binding site of the aptamer improves antidote binding.

Figure 10B:
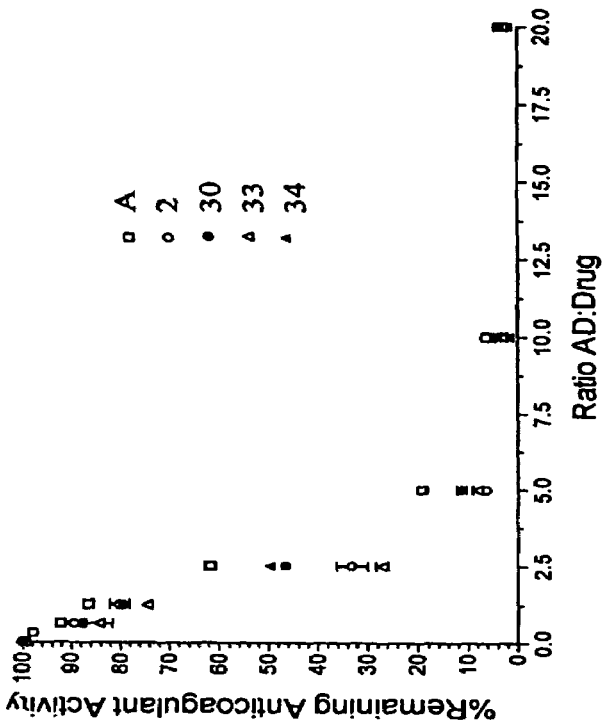
Figure 10B:
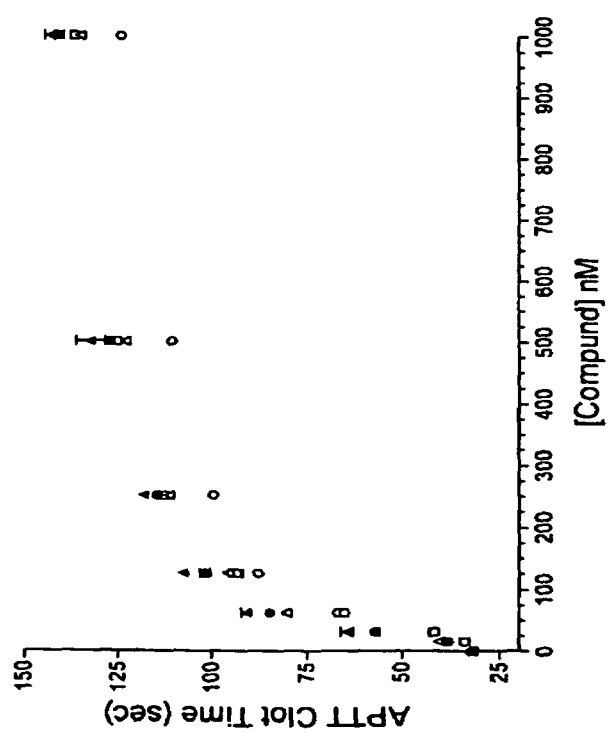

Apt 34 had C16 a 2'fluoro rather than 2'-O-methyl (FIG. 10b). Increase in anticoagulant activity (compare Apt 34 to Apt 33). However, substitution did result in a modest loss of "neutralizability", although 34 still requires a lower excess of antidote to achieve 90% neutralization (~5:1 vs 10:1) than the parental AptA compound. Both results are consistent with an increase in the stability of stem 2 due to 2'-O-methyl substitution.

Sequence Listings:

1) Apt 30 Length: 35 (5'-3') sequence: gugagga CUaUa CC gCG UaaUgC UGC C Uccucac T (SEQ ID NO: 50)

2) Apt 31 Length: 35 (5'-3') sequence: gugagga CUaUa CC gcg UaaUgC ugc C Uccucac T (SEQ ID NO: 51)

3) Apt 32 Length: 35 (5'-3') sequence: gugagga CUaUa CC gcg UaaUgC UgC C Uccucac T (SEQ ID NO: 52)

4) Apt 33 Length: 35 (5'-3') sequence: gugagga CUaUa CC gCg UaaUgC UGC C Uccucac T (SEQ ID NO: 53)

5) Apt 34 Length: 35 (5'-3') sequence: gugagga CUaUa CC gCg UaaUgC uGc C Uccucac T (SEQ ID NO:54)

Example 7

Individual Base Modifications

Apt35-39 compared with original AptA (numbering based upon AptA stem 1):
1) Apt 30 to 31: differences are C16, G17, U24, G25, C26.
2) Apt 30 to 32: differences are C16, G17, G25.
3) Apt 31 to 32: differences are U24, C26.

Figure 11:
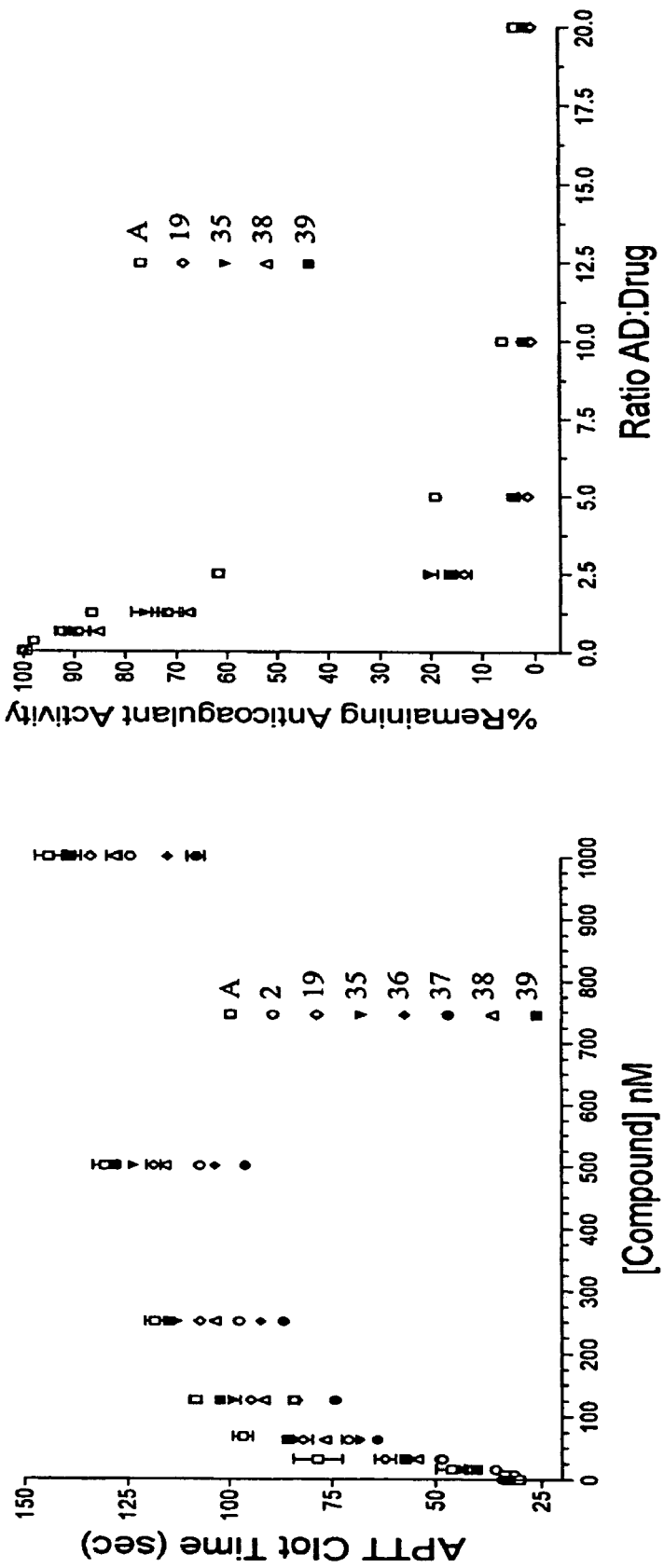
FIG. 11 is a graph of results of activated partial thromboplastin time (APTT) test assays of aptamers Apt A, 2, 19 and 35-39 (left panel) and neutralizability by antidote of Apt A, 19, 35, 38 and 39 (right panel).

The anticoagulant activity of Apt 35-39 was evaluated in standard APTT coagulation assays over compound concentrations ranging from 1 uM to low nanomolar. The "neutralizability" of Apt 35, 38 and 39 was evaluated in standard APTT antidote assays over antidote concentrations (Apt 7 AD) ranging from 5 uM and down. The aptamer concentration was fixed at 125 nM in these assays (FIG. 11).

Figure 12:
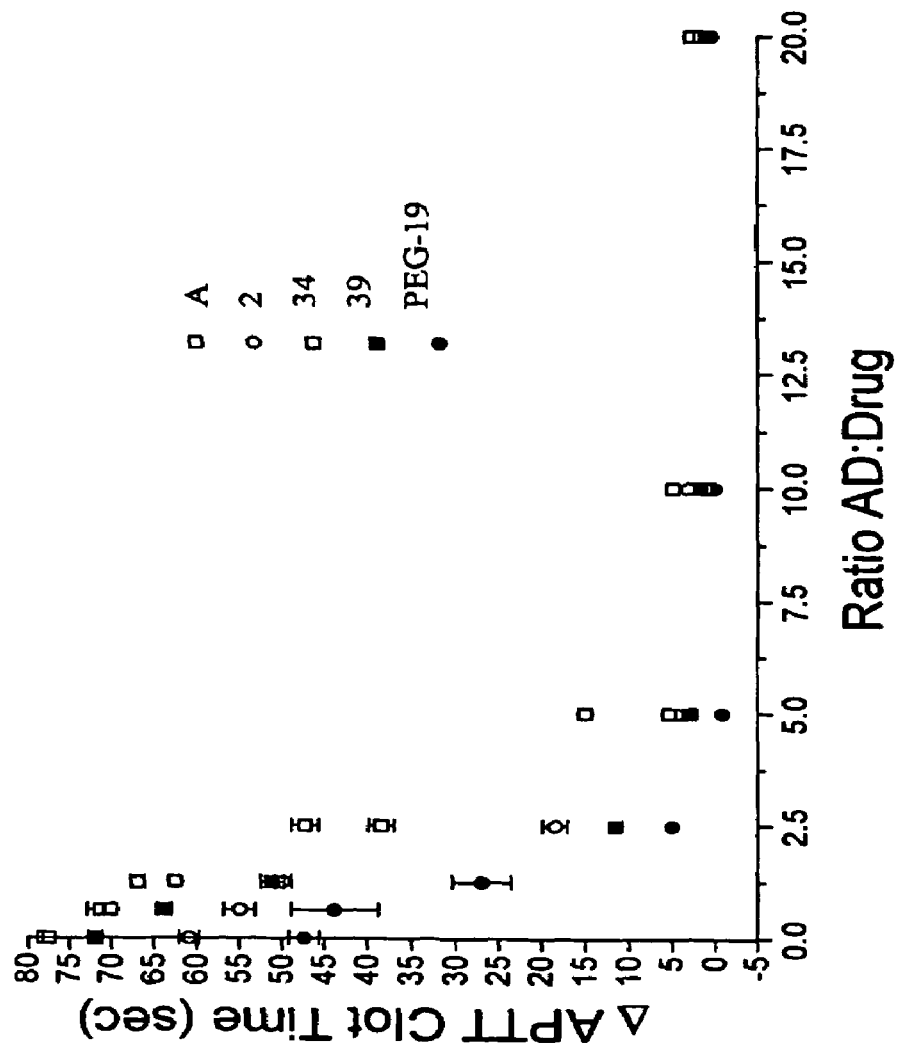
FIG. 12 is a graph of results of neutralizability by antidote assays of aptamers Apt 2, 34, 39 and Peg-19.

Apt 35-39: Anticoagulant activity of Apt 39 is superior to Apt 19 and all other stem 2-optimization constructs in the Apt 19 background (FIG. 11). Results were consistent with those obtained with Apt 34. In addition, potency of Apt 39 is comparable to parental AptA and greater than Apt 2. The neutralization of Apt 39 by Apt7AD is excellent, and similar to neutralization of Apt 19 (FIG. 12). Again, sugar optimization and truncation of Apt 39 has resulted in a compound neutralized at lower excesses of antidote:drug as compared to parental AptA and Apt 2 (FIG. 11).

Sequence Listings:

```
1) Apt35 Length: 31  (5'-3') sequence: gugga CUaUaCC
                      gCG UaaUgC UGC C Uccac T
                      (SEQ ID NO: 55)

2) Apt36 Length: 31  (5'-3') sequence: gugga CUaUaCC
                      gCG UaaUgC ugc C Uccac T
                      (SEQ ID NO:56)

3) Apt37 Length: 31  (5'-3') sequence: gugga CUaUaCC
                      gCG UaaUgC UgC C Uccac T
                      (SEQ ID NO:57)

4) Apt38 Length: 31  (5'-3') sequence: gugga CUaUaCC
                      gCg UaaUgC UGC C Uccac T
                      (SEQ ID NO:58)

5) Apt39 Length: 31  (5'-3') sequence: gugga CUaUaCC
                      gCg UaaUgC uGc C Uccac T
                      (SEQ ID NO:59)
```

Example 8

Conjugation of Aptamer to Delivery Vehicle

The anticoagulant tested is Apt39 with a 40 KDa polyethylene glycol (PEG) conjugated to the 5' end of the aptamer sequence via a 6-carbon $NH_2$ linker (PEG-Apt39). The antidote is Apt7AD.

The anticoagulant activity of PEG-Apt39 was evaluated in standard APTT coagulation assays over compound concentrations ranging from 1 uM to low nanomolar. The anticoagulant activity of Apt39 was compared to two formulations of the parental AptA, CH-Apt S (5' cholesterol-modified) and PEG-AptA (5' 40 KDa PEG-modified). For these studies, the molecular weight of the "aptamer" portion only was used to calculate the concentration of each compound. The "neutralizability" of PEG-Apt39 was evaluated in standard APTT antidote assays over antidote concentrations (Apt7AD) ranging from 5 uM and down. The aptamer concentration was fixed at 125 nM in these assays.

Figure 13:
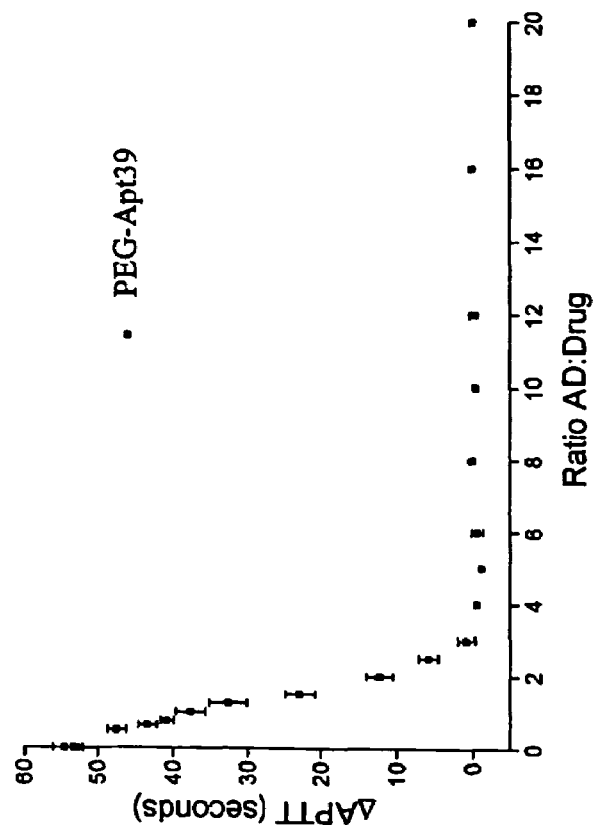
FIG. 13 is a graph of the in vitro anticoagulant activity of PEG-Apt39 compared to CH-AptA and PEG-AptA.
Figure 13:
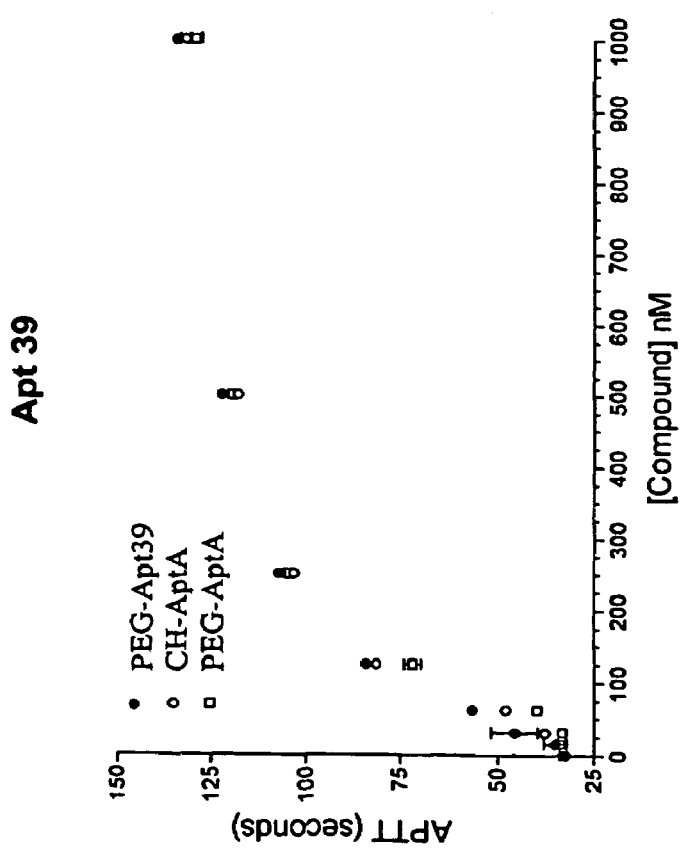

The in vitro anticoagulant activity of PEG-Apt39 is essentially equivalent to CH-AptA and PEG-AptA (FIG. 13).

In vivo Studies

This study compares the in vivo anticoagulant and antidote neutralization activity of PEG-Apt39 in swine to previous data obtained with CH-AptA with respect to: a) Potency and durability of anticoagulant activity and the b) Neutralization of anticoagulant activity. The three experimental groups (n=2 animals for each) are a) Systemic anticoagulation; b) Systemic anticoagulation and drug neutralization; and c) Systemic anticoagulation, drug neutralization and re-anticoagulation.

Experiment: Six neonatal piglets (1 week old, 2.5-3.5 kg) were randomly assigned to three groups. Femoral arterial and venous lines were placed in the piglet. The arterial line was used to monitor blood pressure and arterial blood sampling. The venous line was used to administer drugs and test compounds as specified. Temperature of the piglet was monitored with a nasopharyngeal temperature probe.

The dose of PEG-Apt39 was 0.5 mg/kg (dose of aptamer based upon molecular weight of nucleic acid component only; 10,103.2 Da) for each animal. In the prior experiments with CH-AptA, the aptamer dose was also 0.5 mg/kg (dose of aptamer based upon molecular weight of nucleic acid component only). In experiments in which Apt7 AD was used as an antidote, the dose of the antidote was 3 mg/kg. By comparison, in experiments with CH-AptA in which AptA AD was used, the antidote dose was 5 mg/kg.

a) Systemic anticoagulation. A pre-injection blood sample was taken prior to injection of PEG-Apt39, the drug was then injected (time of injection is t=0), and blood samples removed at 5, 15, 25, 60, 90, 120 and 150 minutes post injection. Activated clotting times (ACT's) were performed on-site immediately after blood draw on the whole blood in duplicate using the Hemochron 801 junior and glass-activated flip-top tubes per the manufacturers directions. Blood samples were then transferred to citrated vacutainer tubes and stored on ice. Platelet poor plasma was prepared, and APTT and PT assays performed per the standard protocol. (FIG. 14A)

The in vivo anticoagulant potency of PEG-Apt39 is superior to CH-AptA. In addition, the loss of anticoagulant activity over time is reduced for PEG-Apt39 vs. CH-AptA. These results are in contrast with the in vitro anticoagulant activity studies, which demonstrate that the anticoagulant activity of PEG-Apt39 and CH-AptA are equivalent in vitro in pooled human plasma.

b) Systemic anticoagulation and drug neutralization. A pre-injection blood sample was taken prior to injection of PEG-Apt39, the drug was then injected (0.5 mg/kg; time of injection is t=0), and blood samples removed at 5 and 15 minutes post drug injection. At t=15 minutes post drug injection, REG1 S7 AD was administered (3 mg/kg), and additional blood samples removed at 25, 60, 90, 120 and 150 minutes post drug injection. Activated clotting times (ACT's) were performed on-site immediately after blood draw on the whole blood in duplicate using the Hemochron 801 junior and glass-activated flip-top tubes per the manufacturers directions. Blood samples were then transferred to citrated vacutainer tubes and stored on ice. Platelet poor plasma was prepared, and APTT and PT assays performed per the standard protocol.

Figure 14B:
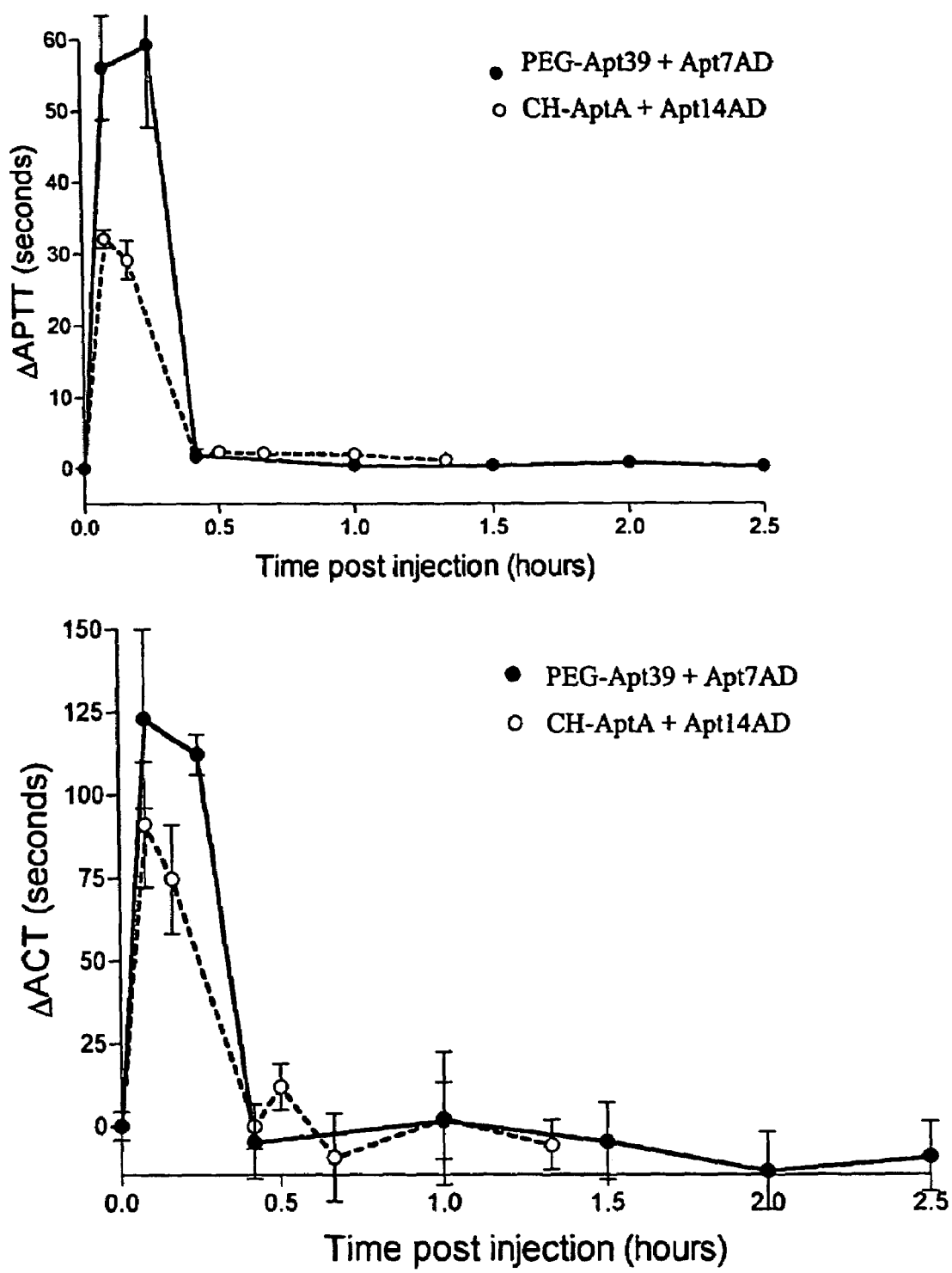
Figure 15:
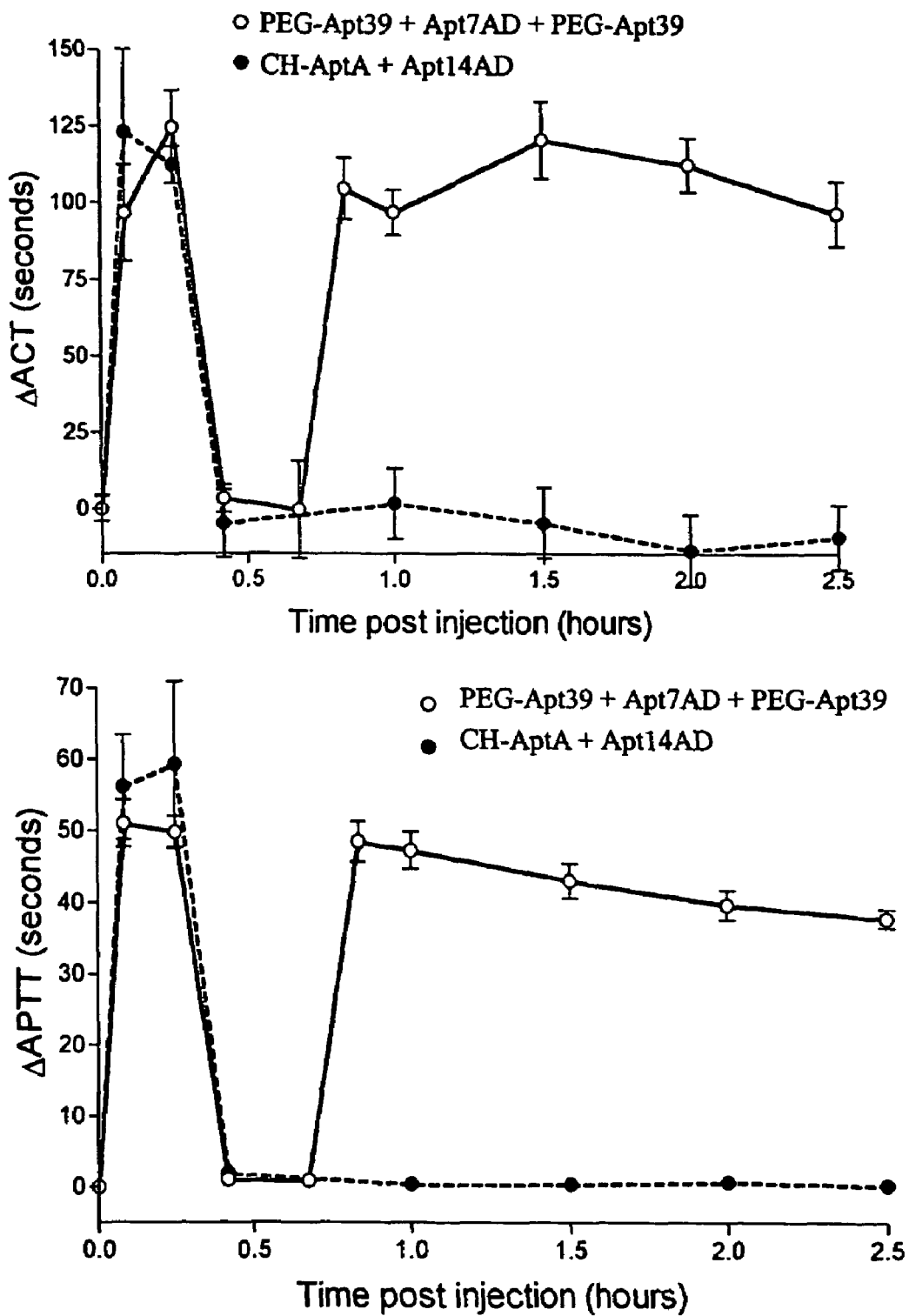
FIG. 15 is graphs of systemic anticoagulant activity (14a) and neutralizability (14b) of PEG-Apt39 in swine. The change in the value of the respective clotting assays is the difference between the clotting time at the time point and the pre-injection baseline for that animal. n=2 for PEG-Apt39 treated animals. Data from this experiment is compared to the anticoagulation and neutralization data for PEG-Apt39 presented in FIG. 3. Whole blood ACT values are shown in the left panel, and plasma APTT values in the panel at right.

Essentially complete neutralization of the anticoagulant activity of PEG-Apt39 was achieved within 10 minutes of administration of 3 mg/kg Apt7 AD. The anticoagulant activity remained neutralized throughout the remainder of the experiment (2 hr and 5 min after initial demonstration of drug neutralization). Thus, the neutralization of PEG-Apt39 appears to be superior to that of CH-AptA, as similar levels of neutralization of PEG-Apt39 can be achieved with a 40% lower dose of antidote (3 mg/kg of Apt7 AD vs. 5 mg/kg REG1 AD). This in vivo data is consistent with in vitro experiments in pooled human plasma in which PEG-Apt39 is more readily neutralized by its matched antidote than any prior formulation of AptA. (FIG. 14B)

c) Systemic anticoagulation, drug neutralization and re-anticoagulation. A pre-injection blood sample was taken prior to injection of PEG-Apt39, the drug was then injected (0.5 mg/kg; time of injection is t=0), and blood samples removed at 5 and 15 minutes post drug injection. At t=15 minutes post drug injection, Apt7 AD was administered (3 mg/kg), and additional blood samples removed at 25, and 40 minutes post drug injection. At t=45 minutes post drug injection (30 minutes following antidote administration), PEG-Apt39 was re-administered (0.5 mg/kg) and additional blood samples removed at 50, 60, 90, 120, and 150 minutes post drug injection. Activated clotting times (ACT's) were performed on-site immediately after blood draw on the whole blood in duplicate using the Hemochron 801 junior and glass-activated flip-top tubes per the manufacturers directions. Blood samples were then transferred to citrated vacutainer tubes and stored on ice. Platelet poor plasma was prepared, and APTT and PT assays performed per the standard protocol. (FIG. 15)

Re-administration of PEG-Apt39 following neutralization of the initial drug dose is feasible within 30 minutes of administration of the neutralizing antidote. The levels of anticoagulation achieved following administration of the first and second dose appear to be equivalent to each other, suggesting that there is little remaining "free" antidote in the circulation at the time of administration of the second dose of drug.

Example 9

Quantification of Aptamer Complex Formation in Plasma

Aptamer levels in plasma are determined using a sandwich-type hybridization assay with an enzyme-linked immunoassay (ELISA) for detection. Quantitation of aptamer employs two oligonucleotide probes, a DNA capture probe, and a 2'O-methyl RNA detection probe. The DNA capture probe is 15 nucleotides in length, is complementary to the 3' terminal 15 nucleotides of the aptamer, and contains a biotin moiety on its 5' terminus, allowing for capture of oligonucleotide complexes containing this probe to an avidin coated surface. The 2'O-methyl RNA detection probe is also 15 nucleotides in length, is complementary to the portion of aptamer to which antidote binds, and contains a digoxigenin moiety to enable detection of complexes containing this probe using standard enzyme-linked fluorescence generating enzyme/substrate reagents.

Quantitation of aptamer is achieved by hybridization of the capture and detection probes to aptamer in plasma and subsequent immobilization of the complex onto the surface of a Neutravidin-coated microtitre plate by way of the 5'-biotin group. Measurement of the digoxigenin-labeled 2'-O-methyl RNA probe is performed subsequent to the plate immobilization reaction using an anti-digoxigenin antibody conjugated to alkaline phosphatase, which catalyzes the fluorescence of a substrate. Fluorescence intensity is then measured, the signal of which is directly proportional to the amount of aptamer present in the calibration standards and validation samples.

The in vitro anticoagulant activity of aptamer Apt39 (SEQ ID NO:88) in plasma from cynomolgus monkeys is reflected by concentration-dependent prolongation of time-to-clot in the APTT assay. Plasma FIX assays were performed to aid in interpretation of the Apt39 APTT dose-response curve in monkey plasma. As shown in Table A, the APTT in monkey plasma is sensitive to the FIX level. However, the magnitude of the response to reduction in the FIX level is modest. A 75% reduction in the FIX level results in a 1.4-fold increase in the APTT, a >95% reduction in the FIX level results in a doubling of the APTT, and a 99.9% reduction in the plasma FIX level yields a 2.5-fold increase in the APTT.

TABLE A

FIX Activity Assay Standard Curve in Cynomolgus Monkey Plasma

| % FIX Level | APTT Clot Time | Fold Increase in Clot Time |
|---|---|---|
| 100* | 35.1 | 1.0 |
| 50 | 41.9 | 1.2 |
| 25 | 49.4 | 1.4 |
| 12.5 | 55.9 | 1.6 |
| 6.25 | 62.2 | 1.8 |
| 3.13 | 68.0 | 1.9 |
| 1.56 | 74.7 | 2.1 |
| 0.78 | 77.7 | 2.2 |
| 0.39 | 83.8 | 2.4 |
| 0.098 | 88.1 | 2.5 |

*100% FIX level represents a 1:5 dilution of normal pooled cynomolgus plasma in buffer. Human FIX-deficient plasma (George King Biomedical) was used as the source of FIX-deficient plasma.

The date in table A indicate that ~6 µg/mL Apt39 is required to inhibit approximately 90% of plasma FIX activity in monkeys (i.e., this concentration yields a 1.6-fold increase in the APTT), and that >95% inhibition of plasma FIX activity occurs at Apt39 concentrations of 10-12 µg/mL.

In vivo Activity of Apt39 and Apt7AD in Cynomolgus Monkeys

The relationship between the anticoagulant properties of Apt39 and the Apt39/Apt7AD complex and the plasma levels of these compounds was evaluated in monkey. Briefly, 12 monkeys were assigned to three treatment groups. Group 1 received the anti-FIXa aptamer Apt39, Group 2 received the antidote Apt7AD and Group 3 was treated with Apt39 and three hours later with Apt7AD. Doses were escalated through two quantities of test articles, with the first dose occurring on Day 4 of the study and the second dose occurring on Day 13. To better understand the dose-response to aptamer, the four monkeys assigned to Group 1 were subdivided into two groups at Day 13, with two animals receiving a low dose (Group 1a, 5 mg/kg) and two animals receiving a high dose (Group 1b, 30 mg/kg).

Figure 16:
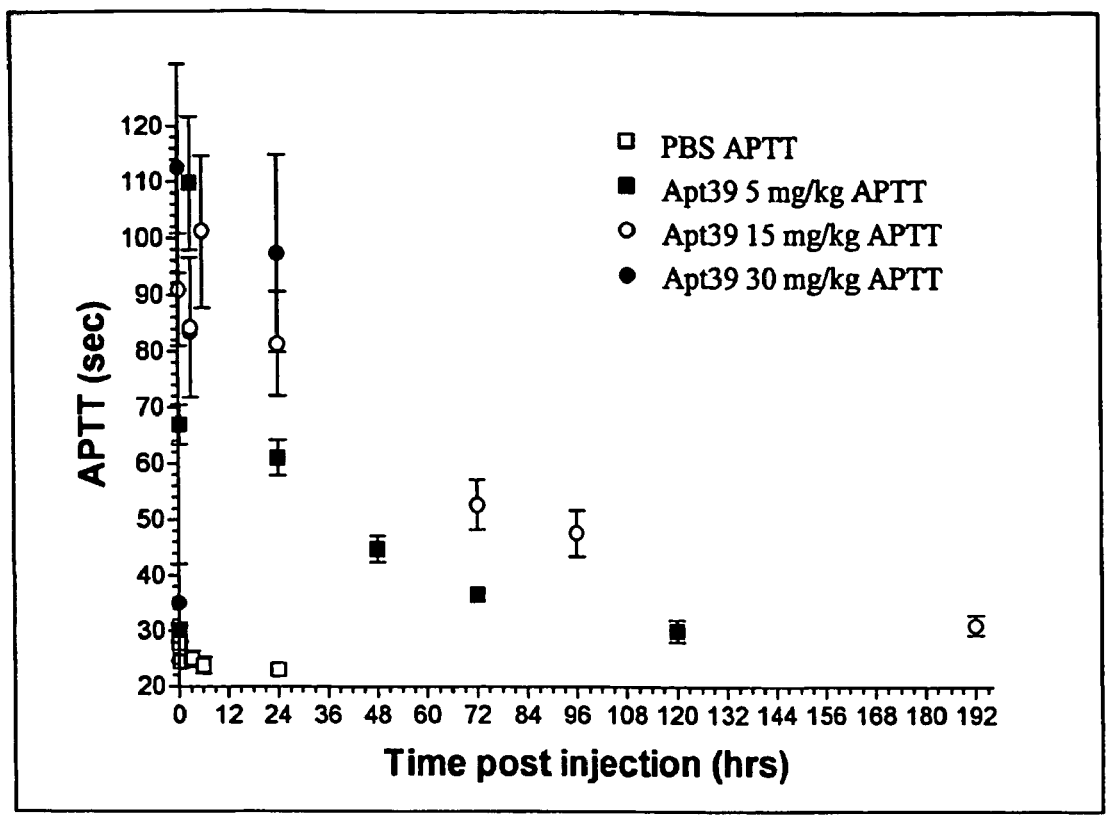
FIG. 16 is a graph of systemic anticoagulation of monkeys by Apt39 administration as described in Example 9. The level of anticoagulation in the monkeys was monitored with the APTT. For animals treated with 15 mg/kg, Apt39 data are presented as the mean ±SEM. For animals at the 5 and 30-mg/kg dose levels, data are presented as the mean ±range, as there were only 2 animals at each of these dose levels.

As shown in FIG. 16, administration of Apt39 at doses ranging from 5 to 30 mg/kg resulted in a profound level of anticoagulation in the monkeys. The mean APTT at each dose level exceeded 60 seconds from 0.25 to 24 hours following aptamer administration, which is equivalent to <0.1% normal plasma FIX levels in the monkey. There is a dose-dependent increase in APTT in response to Apt39 administration. However, the dose-response is not immediately evident due to the fact that, up to the 6-hour time point following Apt39 administration, the aptamer plasma level exceeded the concentration at which the ill vitro APTT dose-response curve approaches a plateau (~40-50 µg/mL; see Table B). At times beyond 6 hours after administration, as the aptamer concentration decreases below this level, the dose-response is more apparent. APTT was followed until it returned to baseline in monkeys receiving 5 and 15 mg/kg doses. Mean APTT returned to baseline by 120 hours at the 5-mg/kg dose level and 192 hours at the 15-mg/kg dose level, consistent with both the ill vitro APTT dose-response curve (data not shown) and the observed half-life of approximately 12 hours in monkeys (see Table B). The whole-blood activated clotting time (ACT) data mirrored the APTT data (data not shown).

There is an excellent correspondence between the mean Apt39 concentration 24 hours post administration in the Group 1a animals and the mean APTT of these animals. The mean aptamer concentration of the animals treated with 5 mg/kg at 24 hours was 15.9 μg/mL and the mean APTT was 61.1 seconds.

TABLE B

Group 1 Apt39 Plasma Levels (μg/mL)

| Time Post Injection | Group 1 Dose Levels (animals/dose level) | | |
|---|---|---|---|
| (hours) | 5 mg/kg (n = 2)* | 15 mg/kg (n = 4) | 30 mg/kg (n = 2)* |
| Pre-dose | 0.2 | <0.04 | 0.2 |
| 0.25 | 59.8 | 179.8 ± 28.9 | 465.5 |
| 3 | 66.6 | 145.6 ± 32.5 | 328.9 |
| 6 | 42.1 | 101.5 ± 13.4 | 275.3 |
| 24 | 15.9 | 51.1 ± 11.2 | 164.6 |

*For Day 13 dosing, animals were split into Group 1a (5 mg/kg) and 1b (30 mg/kg). For these dose levels, the average plasma level for the two animals per dose level is reported. The Apt39 present in Group 1a and 1b animals at the pre-dose time point is residual Apt39 from the 15-mg/kg dose at Day 4. The LLOQ of the assay is <0.04 μg/mL.

In the Group 2 animals treated with the antidote only, mean APTT and ACT were not affected by antidote administration at either dose level tested (30 and 60 mg/kg). Toxicokinetic data were collected at several time points over the first 24 hours after administration. As shown in Table C, low, but measurable levels of the antidote were present in plasma from animals receiving antidote at 0.25 hours after injection of 30 mg/kg on Day 4 or 60 mg/kg on Day 13. The post-dosing level of the antidote was very low by comparison to the concentration of the aptamer (in Group 1) following IV injection.

TABLE C

Group 2 Apt7AD Plasma Levels (μg/mL)

| Time Post Apt39 Injection (hours) | Group 2 Dose Levels (4 animals/dose) | |
|---|---|---|
| | 30 mg/kg | 60 mg/kg |
| Pre-dose | <0.01 | <0.01 |
| 3.25 | 0.4 ± 0.1 | 0.6 ± 0.5 |
| 6 | 0.02 ± 0.01* | <0.02*** |
| 24 | 0.01 ± 0.01** | <0.01*** |

Figure 17:
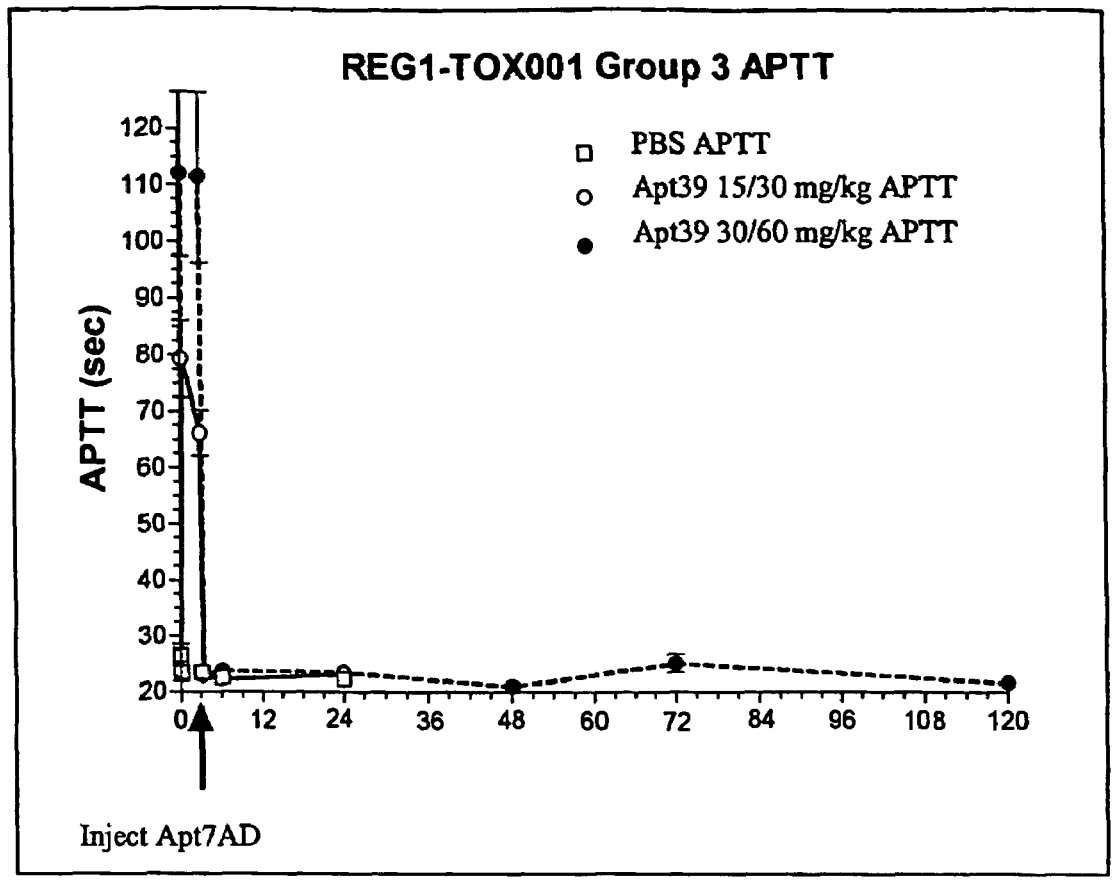
FIG. 17 is a graph of the systemic anticoagulation of monkeys with Apt39 and reversal with antidote Apt7AD, as described in Example 9. The level of anticoagulation in the monkeys was monitored with the APTT. Apt7AD was administered at t=3 hours following Apt39 administration. Data are presented as the mean ±SEM.

*1 animal at <LLOQ of 0.01 included in calculations
**3 animals at <LLOQ of 0.01 included in calculations
***Average of LLOQs The APTT data from animals treated with aptamer followed by antidote 3 hours later (Group 3) are shown in FIG. 17. In agreement with the data from animals treated with aptamer only, administration of aptamer at these dose levels resulted in a profound level of anticoagulation, with the mean APTTs at 0.25 and 3 hours post administration consistent with essentially complete FIX inhibition at both dose levels. Subsequent administration of Apt7AD rapidly and completely neutralized the anticoagulant effects of Apt39 in the monkey, with the mean APTT returning to baseline within 15 minutes following Apt7AD administration. In the Group 3 animals treated with 30/60 mg/kg Apt39/Apt7AD, the APTT was followed for 5 days post aptamer administration. APTT data collected over this time frame indicate the anticoagulant effects of aptamer were durably neutralized, with no evidence of rebound anticoagulation over 120 hours, or approximately 10 half-lives of aptamer in the monkey (FIG. 17).

Toxicokinetic data were collected for 24 hours following Apt39 administration in the Group 3 animals (Table D). For Group 3 animals, both free aptamer and complexed aptamer plasma concentrations were measured. Within 15 minutes of antidote administration, the mean concentration of free aptamer decreased 5,000-10,000 fold, to levels below the Lower Limit of Quantitation (LLOQ) of the assay employed. Concomitant with the decrease in free aptamer levels, the mean plasma concentration of complexed aptamer increased from below the LLOQ of the assay to ~125 to 220 μg/mL at the 15/30 and 30/60 mg/kg dose levels respectively, indicating the rapid decrease in free Apt39 concentrations was due to binding of Apt7AD. The concentration of free aptamer remained below the LLOQ of the assay as long as 3 hours after antidote administration, consistent with the APTT results. At 21 hours after antidote administration, very low levels of Apt39 were detectable in several animals (mean of only 0.17 μg/mL or lower).

TABLE D

Group 3 Free and Complexed Apt389 Plasma Levels (μg/mL)

| Time Post Apt39 Injection (hours) | Group 3 Dose Levels | | | |
|---|---|---|---|---|
| | 15/30 mg/kg Apt39 + Apt7AD | | 30/60 mg/kg Apt39 + Apt7AD | |
| | Free Apt39 | Complexed Apt39 | Free Apt39 | Complexed Apt39 |
| Pre-dose | <0.04 | ND | 0.05 ± 0.01 | ND |
| 0.25 | 280.2 ± 64.3 | ND | 467.6 ± 67 | ND |
| 3.0 | 214.6 ± 31.8 | <0.04 | 488.4 ± 68.6 | <0.04 |
| 3.25 | <0.04 | 125.1 ± 7.9 | <0.04 | 218.2 ± 27.2 |
| 6 | <0.04 | 98.7 ± 20.5 | <0.04 | 184.8 ± 28.9 |
| 24 | 0.14 ± 0.08* | 8.3 ± 4.5 | <0.04 ± 0.01** | 22.3 ± 12 |

*1 animal at <LLOQ of 0.04 μg/mL included in calculations
**3 animals at <LLOQ of 0.04 μg/mL included in calculations
Apt7AD administered at t = 3 hrs immediately after 3 hr blood draw.
(ND) Not determined.

The invention has been described with reference to various specific and preferred embodiments and techniques. It should be understood that many variations and modifications may be made while remaining within the spirit and scope of the invention.

The invention claimed is:

1. A composition comprising a nucleic acid sequence of one of SEQ ID NOs. 19, 39, and 55-59 linked to a polyethylene glycol molecule at a 5' terminus via a linker moiety, or a pharmaceutically acceptable salt thereof.

2. The composition of claim 1 of the formula:

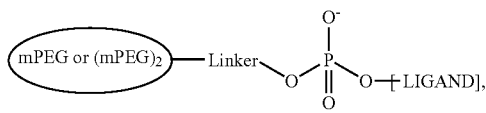

wherein ligand is selected from one of SEQ ID NO. 19, 39, or 55-59 or a pharmaceutically acceptable salt thereof.

3. The composition of claim 1 wherein the composition is produced by conjugating a linker precursor to a nucleic acid molecule to form a nucleic acid linker-composition and further, conjugating a polyethylene glycol precursor moiety to the linker of the nucleic acid-linker composition.

4. The composition of claim 3 in which the linker precursor is selected from the group consisting of:

6-(trifluoroacetamido)hexanol (2-cyanoethyl-N,N-diisopropyl)phosphoramidite of the structure:

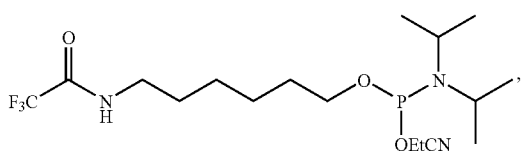

TFA-amino C4 CED phosphoramidite of the structure:

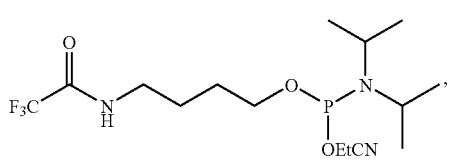

5'-amino modifier C3 TFA of the structure:

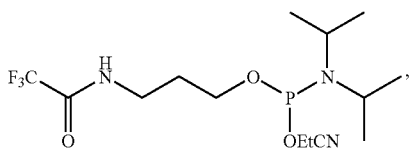

5'-Amino-Modifier C3-TFA

5'-amino modifier 5 of the structure:

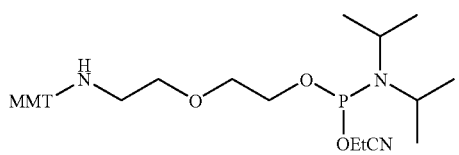

MMT:4-Monomethoxytrityl
5'-Amino-Modifier 5,

5'-amino modifier C12 of the structure:

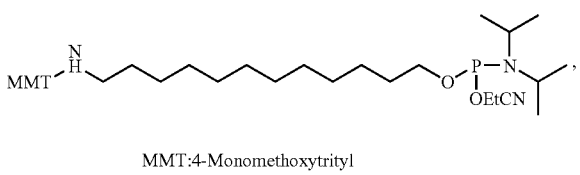

MMT:4-Monomethoxytrityl and 5'thiol-modifier C6 of the structure:

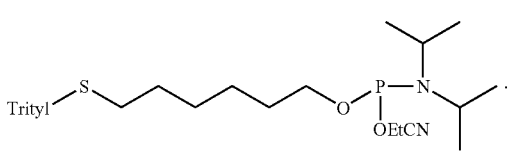

5. The composition of claim 3 wherein the polyethylene glycol precursor is selected from:
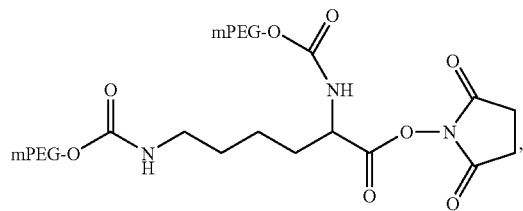
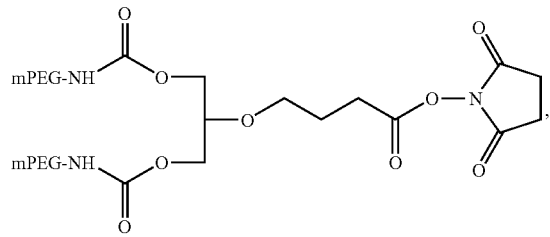
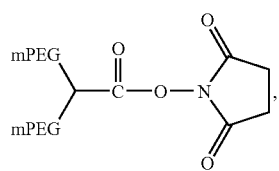
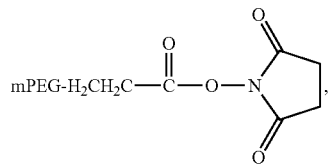
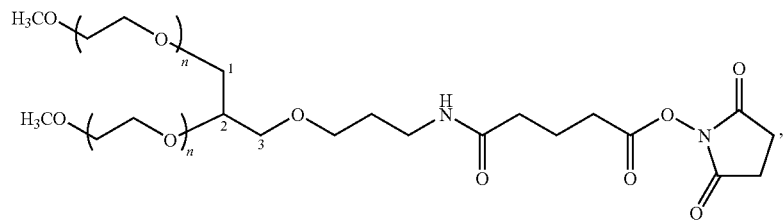
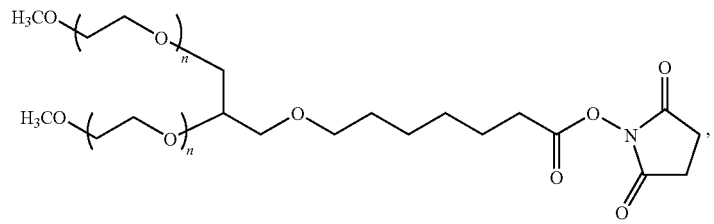
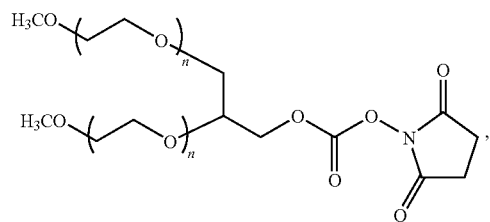
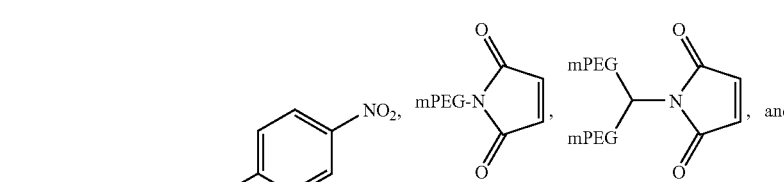
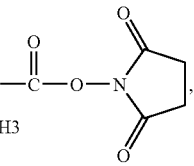
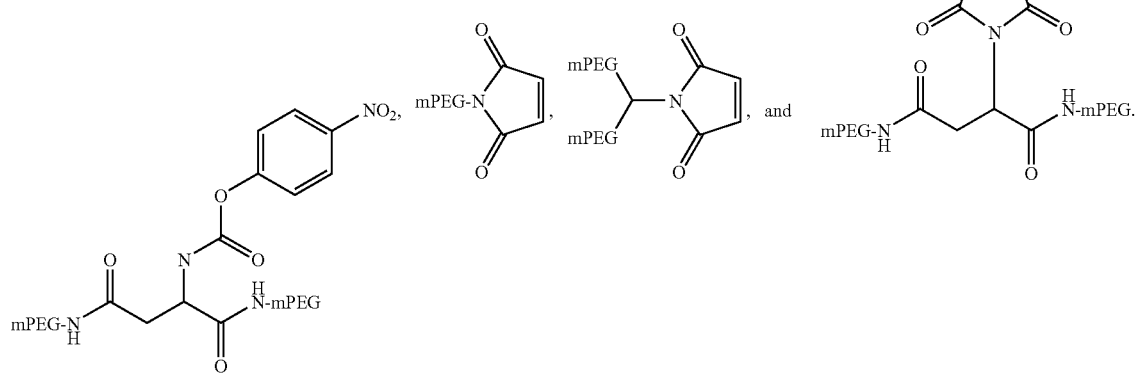

6. The composition of claim 1 wherein the polyethylene glycol has a total mass of about 40 kD.

7. The composition of claim 1 wherein the composition comprises two polyethylene glycol moieties.

8. The composition of claim 7 wherein each moiety has a total mass of about 20 kD.

9. The composition of claim 1 wherein the nucleic acid comprises SEQ ID NO: 19.

10. The composition of claim 1 wherein the nucleic acid comprises SEQ ID NO: 39.

11. The composition of claim 1 comprising the structure:
5'-O-[6-[N$^2$-(monomethoxy 20K polyethylene glycol carbamoyl)-N$^6$-(monomethoxy 20K polyethylene glycol carbamoyl)]-lysylamido]hexyl]-2'-methoxy-2'-deoxguanylyl-(3'-5')-2'-methoxy-2'-deoxyuridylyl-(3'-5')-2'-methoxy-2'-deoxyguanylyl-(3'-5')-2'-methoxy-2'-deoxyguanylyl-(3'-5')-2'-methoxy-2'-deoxyadenylyl-(3'-5')-2'-fluoro-2'-deoxycytidylyl-(3'-5')-2'-fluoro-2'-deoxyuridylyl-(3'-5')-2'-methoxy-2'-deoxyadenylyl-(3'-5')-2'-fluoro-2'-deoxyuridylyl-(3'-5')-2'-methoxy-2'-deoxyadenylyl-(3'-5')-2'-fluoro-2'-deoxycytidylyl-(3'-5')-2'-fluoro-2'-deoxcytidylyl-(3'-5')-2'-methoxy-2'-deoxyguanylyl-(3'-5')-2'-fluoro-2'-deoxycytidylyl-(3'-5')-2'-methoxy-2'-deoxyguanylyl-(3'-5')-2'-fluoro-2'-deoxyuridylyl-(3'-5')-2'-methoxy-2'-deoxyadenylyl-(3'-5')-2'-methoxy-2'-deoxyadenylyl-(3'-5')-2'-fluoro-2'-deoxyuridylyl-(3'-5')-2'-methoxy-2'-deoxyguanylyl-(3'-5')-2'-fluoro-2'-deoxycytidylyl-(3'-5')-2'-methoxy-2'-deoxyuridylyl-(3'-5')-riboguanylyl-(3'-5')-2'-methoxy-2'-deoxycytidylyl-(3'-5')-2'-fluoro-2'-deoxycytidylyl-(3'-5')-2'-fluoro-2'-deoxyuridylyl-(3'-5')-2'-methoxy-2'-deoxcytidylyl-(3'-5')-2'-methoxy-2'-deoxytidylyl-(3'-5')-2'-methoxy-2'-deoxyadenylyl-(3'-5')-2'-methoxy-2'-deoxycytidylyl-(3'-3')-thymidine.

12. The composition of claim 1 of the formula:

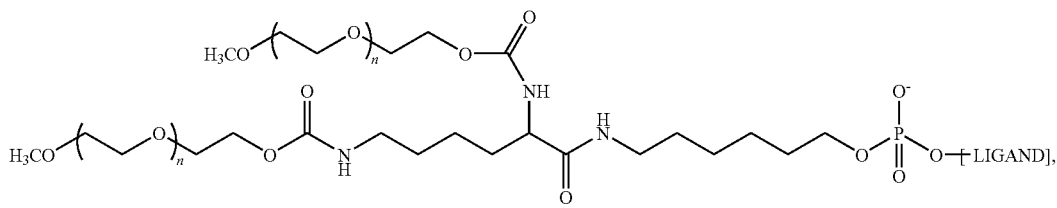

n = approximately 450 or a pharmaceutically acceptable salt thereof.

13. The composition of claim 1 of the formula:

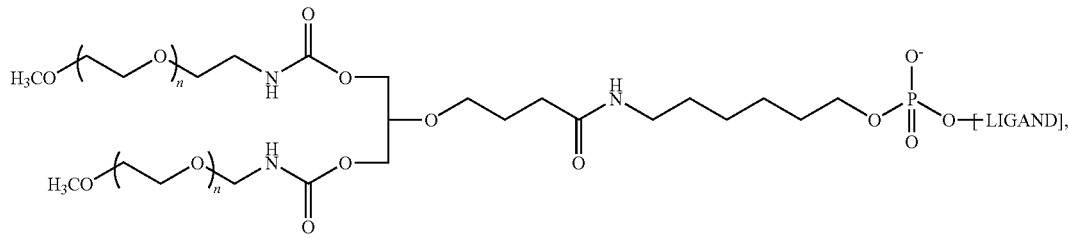

n = approximately 450 or a pharmaceutically acceptable salt thereof.

14. The composition of claim 1 of the formula:

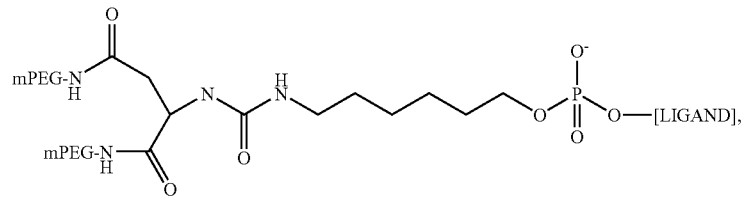

n = approximately 450 or a pharmaceutically acceptable salt thereof.

15. The composition of claim 1 of the formula:

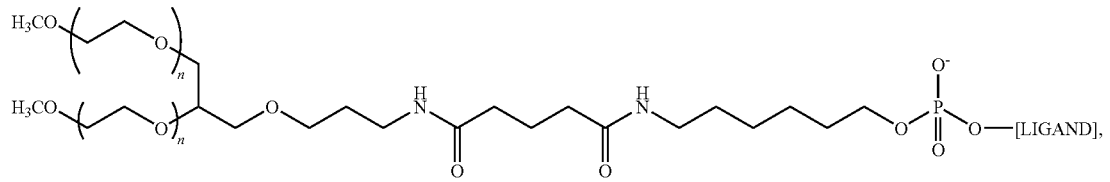

n = approximately 450 or a pharmaceutically acceptable salt thereof.

16. The composition of claim 1 of the formula:

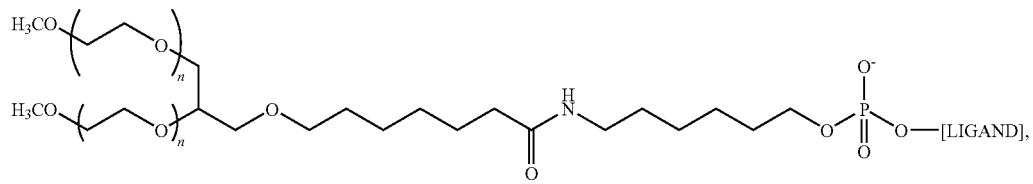

n = approximately 450 or a pharmaceutically acceptable salt thereof.

17. The composition of claim 1 of the formula:

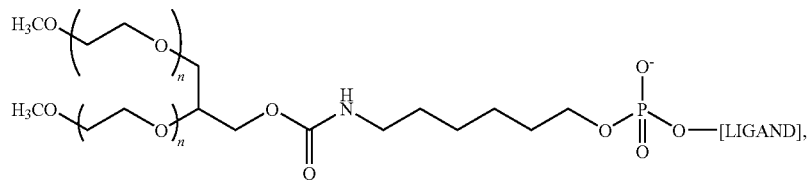

n = approximately 450 or a pharmaceutically acceptable salt thereof.

18. The composition of claim 1 of the formula:

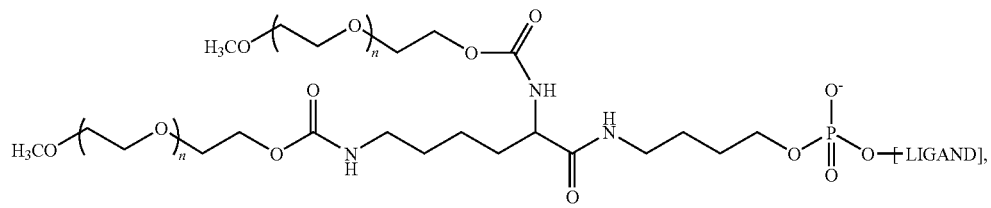

n = approximately 450 or a pharmaceutically acceptable salt thereof.

19. The composition of claim 1 of the formula:

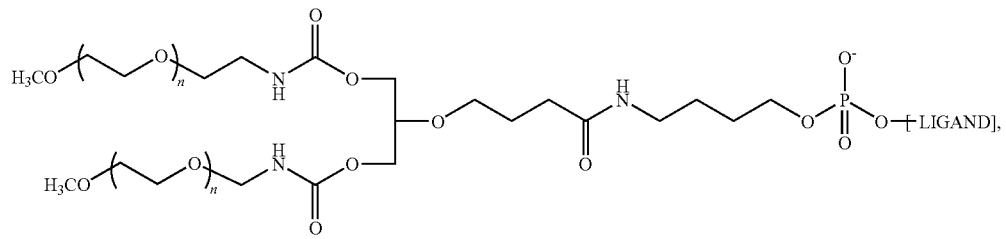

n = approximately 450 or a pharmaceutically acceptable salt thereof.

20. The composition of claim 1 of the formula:

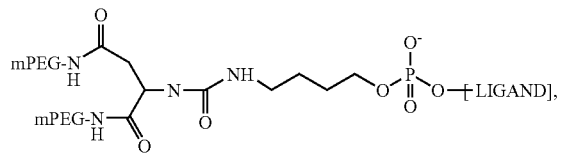

n = approximately 450 or a pharmaceutically acceptable salt thereof.

21. The composition of claim 1 of the formula:

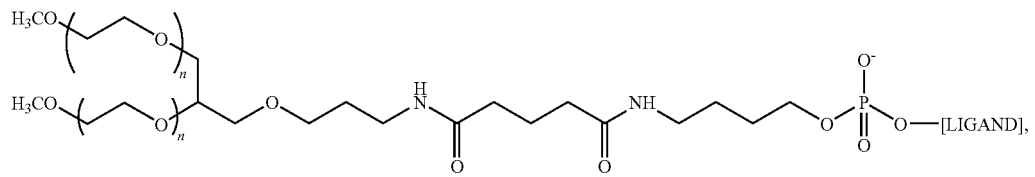

n = approximately 450 or a pharmaceutically acceptable salt thereof.

22. The composition of claim 1 of the formula:

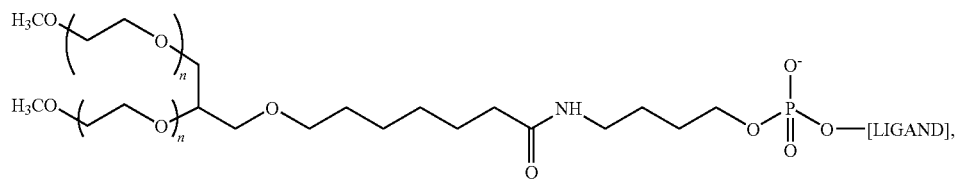

n = approximately 450 or a pharmaceutically acceptable salt thereof.

23. The composition of claim 1 of the formula:

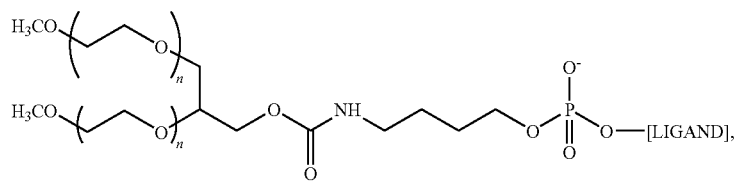

n = approximately 450 or a pharmaceutically acceptable salt thereof.

24. The composition of claim 1 of the formula:

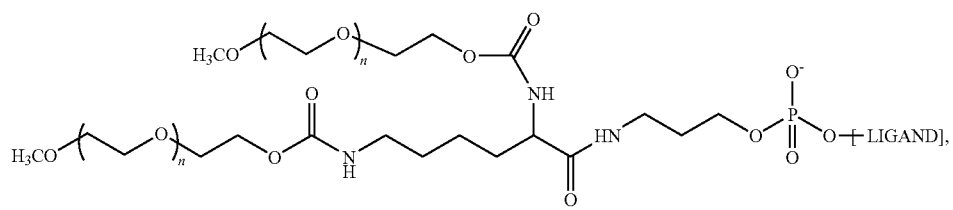

n = approximately 450 or a pharmaceutically acceptable salt thereof.

25. The composition of claim 1 of the formula:

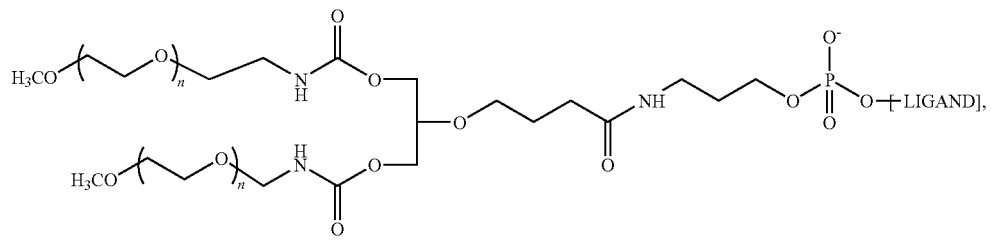

n = approximately 450 or a pharmaceutically acceptable salt thereof.

26. The composition of claim 1 of the formula:

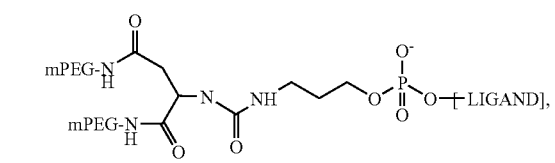

n = approximately 450 or a pharmaceutically acceptable salt thereof.

27. The composition of claim 1 of the formula:

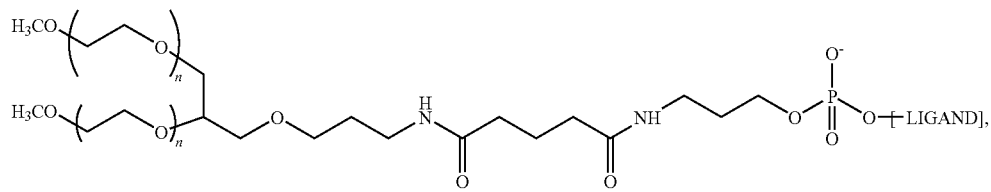

n = approximately 450 or a pharmaceutically acceptable salt thereof.

28. The composition of claim 1 of the formula:

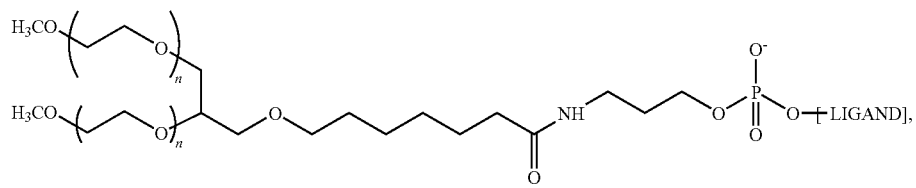

n = approximately 450 or a pharmaceutically acceptable salt thereof.

29. The composition of claim 1 of the formula:

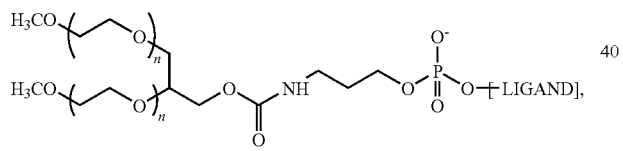

n = approximately 450 or a pharmaceutically acceptable salt thereof.

30. The composition of claim 1 of the formula:

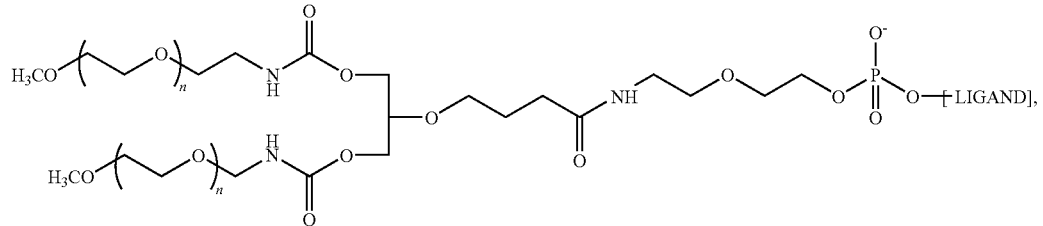

n = approximately 450 or a pharmaceutically acceptable salt thereof.

31. The composition of claim 1 of the formula:

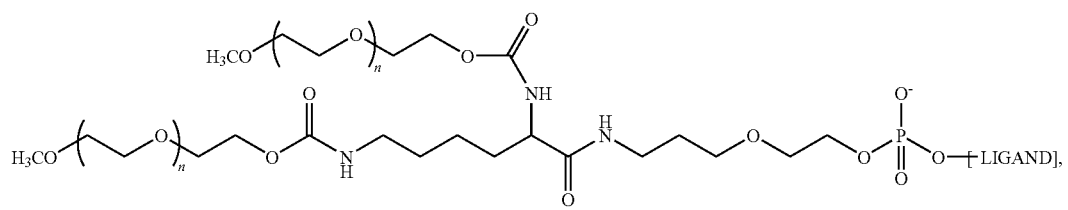

n = approximately 450 or a pharmaceutically acceptable salt thereof.

32. The composition of claim 1 of the formula:

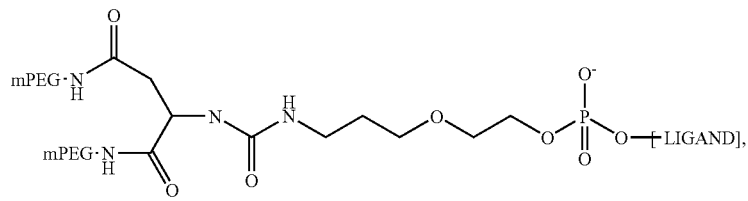

n = approximately 450 or a pharmaceutically acceptable salt thereof.

33. The composition of claim 1 of the formula:

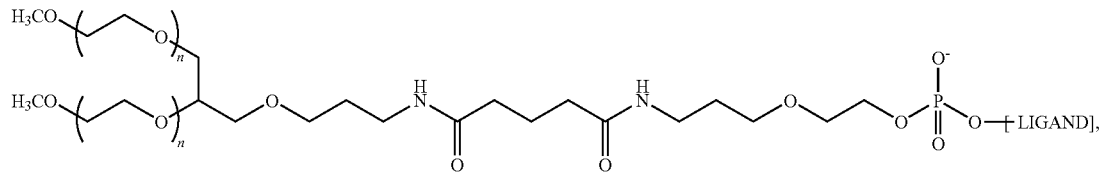

n = approximately 450 or a pharmaceutically acceptable salt thereof.

34. The composition of claim 1 of the formula:

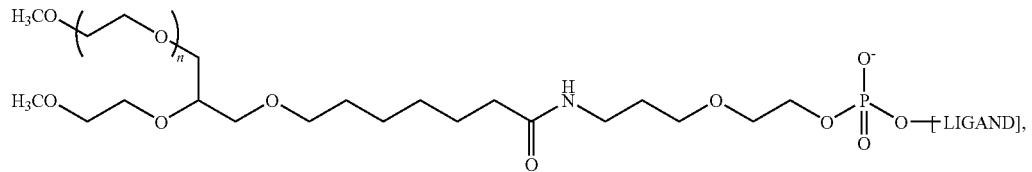

n = approximately 450 or a pharmaceutically acceptable salt thereof.

35. The composition of claim 1 of the formula:

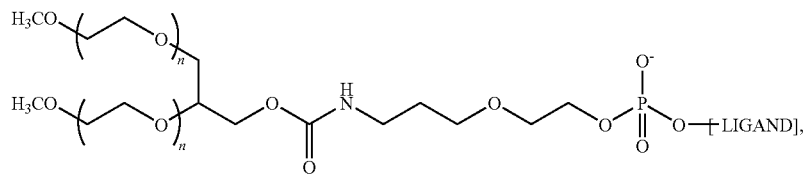

n = approximately 450 or a pharmaceutically acceptable salt thereof.

36. The composition of claim 1 of the formula:

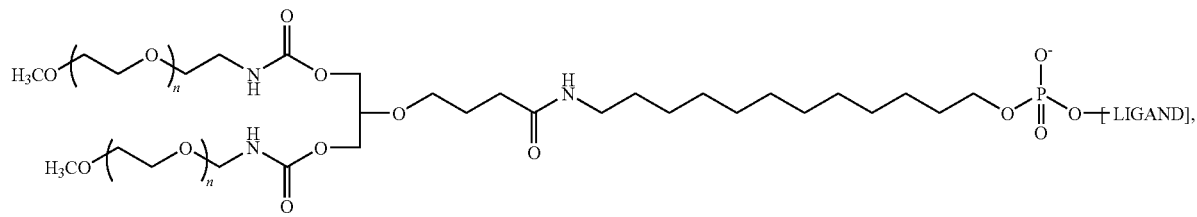

n = approximately 450 or a pharmaceutically acceptable salt thereof.

37. The composition of claim 1 of the formula:

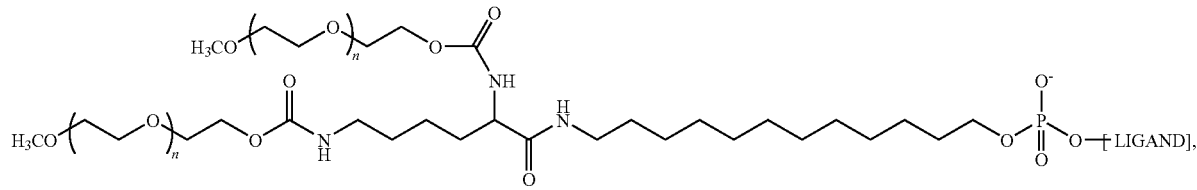

n = approximately 450 or a pharmaceutically acceptable salt thereof.

38. The composition of claim 1 of the formula:

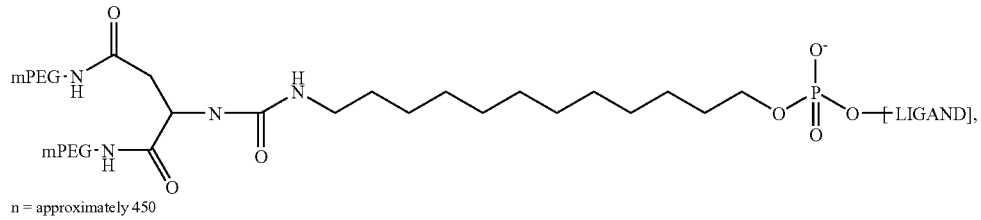

n = approximately 450 or a pharmaceutically acceptable salt thereof.

39. The composition of claim 1 of the formula:

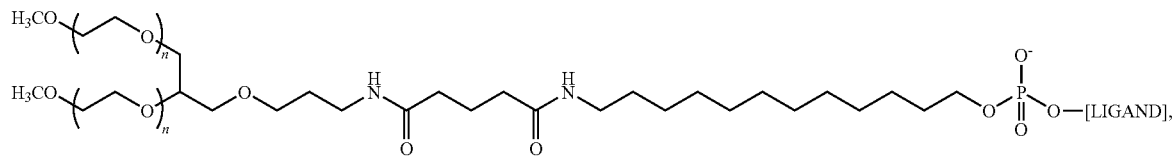

n = approximately 450 or a pharmaceutically acceptable salt thereof.

40. The composition of claim 1 of the formula:

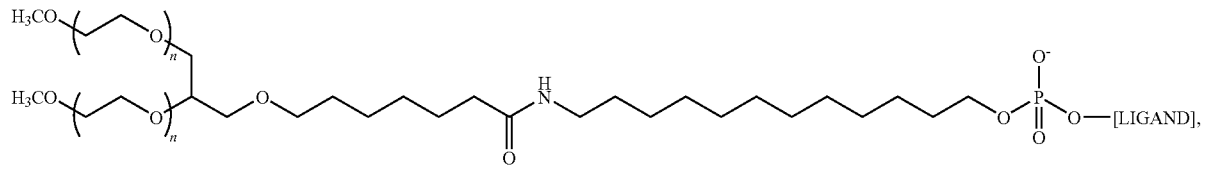

n = approximately 450 or a pharmaceutically acceptable salt thereof.

41. The composition of claim 1 of the formula:

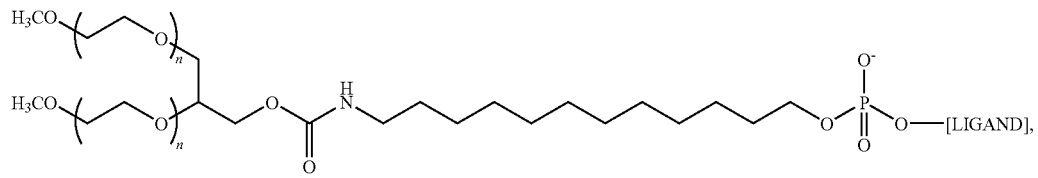

n = approximately 450 or a pharmaceutically acceptable salt thereof.

42. The composition of claim 1 of the formula:

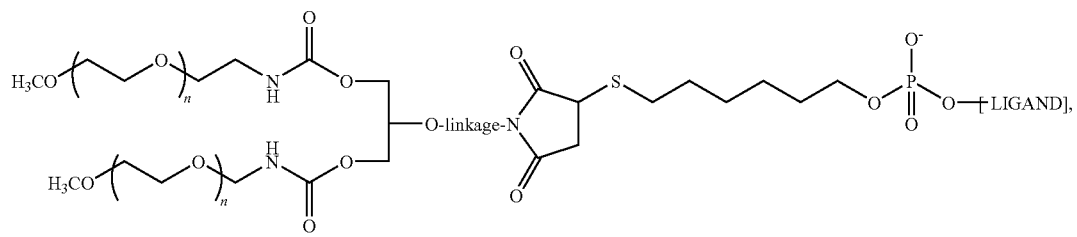

n = approximately 450 or a pharmaceutically acceptable salt thereof.

43. The composition of claim 1 of the formula:

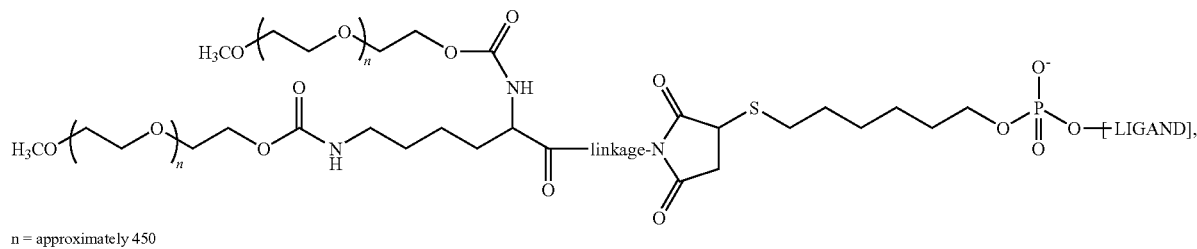

n = approximately 450 or a pharmaceutically acceptable salt thereof.

44. A method of regulating blood coagulation comprising contacting a Factor IXa molecule with a composition comprising a nucleic acid sequence of one of SEQ ID NOs. 19, 39, and 55-59 linked to a polyethylene glycol molecule at a 5' terminus via a linker moiety, or a pharmaceutically acceptable salt thereof.

45. The method of claim 44 wherein the nucleic acid sequence is an aptamer that comprises the structure:

5'-O-[6-[$N^2$-(monomethoxy 20K polyethylene glycol carbamoyl)-$N^6$-(monomethoxy 20K polyethylene glycol carbamoyl)]-lysylamido]hexyl]-2'-methoxy-2'-deoxguanylyl-(3'-5')-2'-methoxy-2'-deoxyuridylyl-(3'-5')-2'-methoxy-2'-deoxyguanylyl-(3'-5')-2'-methoxy-2'-deoxyguanylyl-(3'-5')-2'-methoxy-2'-deoxyadenylyl-(3'-5')-2'-fluoro-2'-deoxycytidylyl-(3'-5')-2'-fluoro-2'-deoxyuridylyl-(3'-5')-2'-methoxy-2'-deoxyadenylyl-(3'-5')-2'-fluoro-2'-deoxyuridylyl-(3'-5')-2'-methoxy-2'-deoxyadenylyl-(3'-5')-2'-fluoro-2'-deoxycytidylyl-(3'-5')-2'-fluoro-2'-deoxycytidylyl-(3'-5')-2'-methoxy-2'-deoxyguanylyl-(3'-5')-2'-fluoro-2'-deoxycytidylyl-(3'-5')-2'-methoxy-2'-deoxyguanylyl-(3'-5')-2'-fluoro-2'-deoxyuridylyl-(3'-5')-2'-methoxy-2'-deoxyadenylyl-(3'-5')-2'-methoxy-2'-deoxyadenylyl-(3'-5')-2'-fluoro-2'-deoxyuridylyl-(3'-5')-2'-methoxy-2'-deoxyguanylyl-(3'-5')-2'-fluoro-2'-deoxycytidylyl-(3'-5')-2'-methoxy-2'-deoxyuridylyl-(3'-5')-riboguanylyl-(3'-5')-2'-methoxy-2'-deoxycytidylyl-(3'-5')-2'-fluoro-2'-deoxycytidylyl-(3'-5')-2'-fluoro-2'-deoxyuridylyl-(3'-5')-2'-methoxy-2'-deoxcytidylyl-(3'-5')-2'-methoxy-2'-deoxytidylyl-(3'-5')-2'-methoxy-2'-deoxyadenylyl-(3'-5')-2'-methoxy-2'-deoxcytidylyl-(3'-3')-thymidine, or a pharmaceutically acceptable salt thereof.

46. The method of claim 44 further comprising contacting the composition with an antidote oligonucleotide.

* * * * *